(12) United States Patent
Mauro et al.

(10) Patent No.: US 10,335,063 B2
(45) Date of Patent: Jul. 2, 2019

(54) SYSTEMS AND METHODS FOR APPLYING OR RECEIVING SIGNALS TO OR FROM BIOLOGICAL TISSUES

(71) Applicant: COMBOBUTRONICS LLC, Glen Rock, NJ (US)

(72) Inventors: Kevin Mauro, Jersey City, NJ (US); Grace Taylor, Jersey City, NJ (US)

(73) Assignee: COMBOBUTRONICS LLC, Glen Rock, NJ (US)

( * ) Notice: Subject to any disclaimer, the term of this patent is extended or adjusted under 35 U.S.C. 154(b) by 0 days.

(21) Appl. No.: 15/918,382

(22) Filed: Mar. 12, 2018

(65) Prior Publication Data

US 2018/0303421 A1 Oct. 25, 2018

Related U.S. Application Data

(63) Continuation of application No. 15/885,353, filed on Jan. 31, 2018.

(Continued)

(51) Int. Cl.
*A61B 5/117* (2016.01)
*A61N 2/12* (2006.01)
(Continued)

(52) U.S. Cl.
CPC ............ *A61B 5/117* (2013.01); *A61B 5/0478* (2013.01); *A61B 5/05* (2013.01); *A61B 5/6815* (2013.01);
(Continued)

(58) Field of Classification Search
CPC ... A61B 5/04; A61B 5/04001; A61B 5/04008; A61B 5/0408; A61B 5/04085;
(Continued)

(56) References Cited

U.S. PATENT DOCUMENTS

| 5,215,088 A | 6/1993 | Normann et al. |
| 6,217,574 B1 | 4/2001 | Webster |

(Continued)

FOREIGN PATENT DOCUMENTS

| WO | 2016109851 A1 | 7/2016 |
| WO | 2017091705 A1 | 6/2017 |

OTHER PUBLICATIONS

International Search Report and Written Opinion issued in Application No. PCT/US2018/021355 dated May 17, 2018, 9 pages.
(Continued)

*Primary Examiner* — Eun Hwa Kim
(74) *Attorney, Agent, or Firm* — Rothwell, Figg, Ernst & Manbeck, P.C.

(57) ABSTRACT

Systems and methods for applying and/or receiving electrical, magnetic, magnetoelectric, vibratory, or electromagnetic signals to biological tissues are described. In some embodiments, one or more of a conductive tip and a base may be provided. The tip may include a channel and an outer surface that approximates a portion of a sphere or cone and may be sized to fit within a user's ear. The base may be configured to be coupled to the tip and may include a conductor in electrical contact with the tip such that an electrical signal may pass between the base and the tip.

15 Claims, 37 Drawing Sheets

Related U.S. Application Data

(60) Provisional application No. 62/488,501, filed on Apr. 21, 2017, provisional application No. 62/501,042, filed on May 3, 2017, provisional application No. 62/501,053, filed on May 3, 2017, provisional application No. 62/501,046, filed on May 3, 2017.

(51) Int. Cl.

| | |
|---|---|
| *A61N 2/00* | (2006.01) |
| *A61B 5/00* | (2006.01) |
| *A61B 5/0478* | (2006.01) |
| *A61B 5/05* | (2006.01) |
| *A61N 1/36* | (2006.01) |
| *A61N 1/04* | (2006.01) |
| *A61B 5/0476* | (2006.01) |
| *G16H 50/00* | (2018.01) |

(52) U.S. Cl.
CPC ......... *A61N 1/0456* (2013.01); *A61N 1/0472* (2013.01); *A61N 1/36014* (2013.01); *A61N 2/002* (2013.01); *A61N 2/12* (2013.01); *A61B 5/0476* (2013.01); *A61B 5/6814* (2013.01); *A61B 5/6824* (2013.01); *A61B 5/6828* (2013.01); *A61B 5/6839* (2013.01); *A61B 2562/028* (2013.01); *A61B 2562/0209* (2013.01); *A61B 2562/125* (2013.01); *A61B 2562/164* (2013.01); *A61N 1/0484* (2013.01); *A61N 1/3603* (2017.08); *A61N 1/36025* (2013.01); *A61N 1/36036* (2017.08); *G16H 50/00* (2018.01)

(58) Field of Classification Search
CPC ... A61B 5/0448; A61B 5/0476; A61B 5/6815; A61B 5/6816; A61B 5/6817; A61B 5/6868; A61B 2562/0209; A61B 2562/028; A61B 2562/135; A61B 2562/0476; A61B 5/117; A61N 1/0472; A61N 1/0456; A61N 1/36014; A61N 1/36036; A61N 1/3603; A61N 1/36025
See application file for complete search history.

(56) References Cited

U.S. PATENT DOCUMENTS

| | | |
|---|---|---|
| 8,774,937 B2 | 7/2014 | Mercanzini et al. |
| 8,903,494 B2 | 12/2014 | Goldwasser et al. |
| 2002/0123673 A1 | 9/2002 | Webb et al. |
| 2004/0133390 A1* | 7/2004 | Osorio ................. A61B 5/0006 702/178 |
| 2007/0106143 A1 | 5/2007 | Flaherty |
| 2007/0150027 A1 | 6/2007 | Rogers |
| 2007/0239230 A1* | 10/2007 | Giftakis ............... A61B 5/4094 607/62 |
| 2007/0288077 A1 | 12/2007 | Bulkes et al. |
| 2009/0004471 A1 | 1/2009 | Amthor |
| 2013/0216740 A1 | 8/2013 | Russell-Clarke et al. |
| 2013/0274583 A1 | 10/2013 | Heck |
| 2013/0345534 A1* | 12/2013 | Hoss .................. A61B 5/14532 600/345 |
| 2014/0140567 A1 | 5/2014 | Leboeuf et al. |
| 2015/0360030 A1* | 12/2015 | Cartledge .......... A61N 1/36036 607/60 |
| 2015/0367122 A1 | 12/2015 | Morshed et al. |
| 2016/0008632 A1* | 1/2016 | Wetmore ................ A61N 7/00 601/2 |
| 2016/0128588 A1 | 5/2016 | Melosh et al. |
| 2016/0346541 A1 | 12/2016 | Bennett |
| 2017/0215753 A1 | 8/2017 | Lee |
| 2017/0368348 A1* | 12/2017 | Le Van Quyen .... A61N 1/0408 |

OTHER PUBLICATIONS

Mauro, Kevin, "Combobutronics for Useful Work", retrieved from Internet on Jan. 19, 2018, 7 pages.
Karpathy, Andrej, "The Unreasonable Effectiveness of Recurrent Neural Networks", Andrej Karpathy blog, May 21, 2015, 33 pages.
Notice of Allowance issued in related U.S. Appl. No. 15/885,353 dated Nov. 28, 2018, 26 pages.
Non-Final Office Action issued in related U.S. Appl. No. 15/918,465 dated Oct. 26, 2018, 43 pages.
Non-Final Office Action issued in related U.S. Appl. No. 15/918,428 dated Oct. 11, 2018, 44 pages.
U.S. Non-Final Office Action issued in U.S. Appl. No. 15/885,353 dated Jul. 13, 2018. (27 pages).

\* cited by examiner

SYSTEMS AND METHODS FOR APPLYING OR RECEIVING SIGNALS TO OR FROM BIOLOGICAL TISSUES

RELATED APPLICATIONS

This application is a continuation of U.S. application Ser. No. 15/885,353 filed Jan. 31, 2018, which claims the benefit of U.S. Provisional App. No. 62/488,501 filed Apr. 21, 2017, U.S. Provisional App. No. 62/501,042 filed May 3, 2017, U.S. Provisional App. No. 62/501,053 filed May 3, 2017, and U.S. Provisional App. No. 62/501,046 filed May 3, 2017.

BACKGROUND

Field of Invention

The present invention relates to systems and methods for applying and/or receiving electrical, magnetic, magnetoelectric, vibratory, or electromagnetic signals to and/or from biological tissues.

Discussion of the Background

There are a number of applications in which it is desirable to apply and/or receive electrical, magnetic, magnetoelectric, or electromagnetic signals to biological tissues. In some applications, for example, it may be desirable to monitor and record electrical activity of the brain (e.g., electroencephalography). Such monitoring may be used for diagnostic purposes. In other cases, electrical signals received from the brain may be used to facilitate a brain-machine interface. For example, individuals who have lost use of certain motor functions may benefit from using measurements of brain activity to direct the actions of prosthetics or other machines.

In still other cases, an individual may wish to apply an electrical, magnetic, magnetoelectric, vibratory or electromagnetic stimulus or current to a portion of their body. Studies have found that such stimulus, when applied to the brain, may promote cognitive and memory function. It has been found that such stimulus may increase blood flow, improve or trigger muscle function, and promote general health and wellness. A major challenge in transferring signals to and from the human body comes from the skin. Skin—and in particular the first layer of skin—contains a substantial percentage of the impedance when performing bioelectric recording and stimulating. When recording across this the skin, the internal bioelectric signals are made weaker relative to external noise by the increased electromotive force needed to drive current across the electrode-skin interface, resulting in smearing of the input signal and a higher signal-to-noise ratio. When stimulating across this interface, the signals entering the skin are not only made weaker, but also tend to focally pinpoint into a single point on the skin, resulting in pain and sometimes permanent burns.

Solutions to the high skin impedance problem generally have a number of trade-offs in clinical, laboratory, and consumer products. Invasive electrodes, which are implanted inside the body, easily subvert the problem of having to go through any layers of skin, but they are expensive, require surgery to implant, and have long-term compatibility issues. Non-invasive electrodes, which stay outside of the inner body tissue, are cheaper, easily-removable, and have fewer long-term compatibility problems. When using non-invasive electrodes, one manner to reduce skin impedance is to have a trained professional first "scratch off" the first layer of skin prior to electrode application. Subverting the first layer of skin in this manner can lower skin impedance by 60 to 90%. Another option with similar results is to wet the skin with an appropriate ionic or saline solution. This lowers impedances to similar levels by carrying the current more effectively across the skin layers, as the solution is able to penetrate deeper skin layers and create a conductive path towards the signal, but requires constantly wetting the electrodes for longer duration use. A third technique used today is the forceful "pin-electrode" technique which uses tiny metal pins to penetrate the skin layers, resulting in discomfort that is unsuitable for long-term recordings.

In all of these techniques, there is an undesirable level of discomfort, inconvenience, and delay. There is a need, therefore, for techniques to reduce impedance while maximizing comfort and ease of use.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

In some embodiments, a system for applying and/or receiving an electrical signal may be provided. The system may include a body and a conductor, which may be configured to be electrically coupled to at least one of a power source and a detector. The system may further include a first filament, which may include a base portion and a first tip end. In some embodiments, the base portion may be electrically coupled to the conductor, and the first filament may be electrically conductive such that the first filament is configured to carry an electrical signal between the base portion and the first tip end. In some embodiments, at least a portion of the first filament may be arranged to contact a biological tissue portion.

In some embodiments, a method of applying and/or receiving an electrical signal via a biological tissue portion may be provided. The method may include positioning a system proximate a biological tissue portion. In some embodiments, the system may include a body and a conductor, which may be configured to be electrically coupled to at least one of a power source and a detector. In some embodiments, the system may include a first filament, which may include a base portion and a first tip end. In some embodiments, the base portion may be electrically coupled to the conductor, and the first filament may be electrically conductive such that the first filament is configured to carry an electrical signal between the base portion and the first tip end. In some embodiments, the method may include advancing the first filament toward the biological tissue portion such that the first tip end contacts the biological tissue portion. In some embodiments, the method may include using the first filament to apply and/or receive an electrical signal via the biological tissue portion.

In some embodiments, a system for applying and/or receiving an electrical signal may be provided. The system may include a conductive tip, which may in turn include a channel and an outer surface having a shape that approximates a portion of a sphere or cone. In some embodiments, the tip may be sized to fit within a user's ear. In some embodiments, the system may include a base configured to be coupled to the tip. In some embodiments, the base may include a conductor in electrical contact with the tip such that an electrical signal may pass between the base and the tip.

In some embodiments, a method for applying and/or receiving an electrical signal may be provided. The method may include placing a conductive tip within a user's ear such that the tip contacts a portion of the user's skin within the ear. In some embodiments, the tip may include a channel and may be coupled to a base. In some embodiments, the base may include a conductor in electrical contact with the tip such that an electrical signal may pass between the base and the tip. In some embodiments, the method may include applying and/or receiving an electrical signal via the portion of the user's skin.

In some embodiments, a method for applying and/or receiving an electrical signal may be provided. The method may include placing a system including a body and an electrode in contact with a biological tissue portion. In some embodiments, the body may have a deformation characteristic such that when a proximal end of the body is fixed and a first torque is applied to a distal end of the body such that the body exhibits 30 degrees of flexion relative to an original state, the body retains at least 10 degrees of deformation after the first torque is removed. In some embodiments, the body may have a flexibility characteristic such that a second torque less than or equal to 2.5 Newton-meters produces at least 30 degrees of flexion when the second torque is applied to a distal end of the body while a proximal end of the body is fixed. In some embodiments, the method may include applying a force to the body such that the body plastically deforms to adapt to a shape of the biological tissue portion. In some embodiments, the method may include using the electrode to apply and/or receive an electrical signal via the biological tissue portion.

In some embodiments, a system for applying and/or receiving an electrical signal may be provided. The system may include a body and a conductor, which may be configured to be electrically coupled to at least one of a power source and a detector. In some embodiments, the system may include an electrode, which may include a surface configured to contact a biological tissue portion and apply and/or receive an electrical signal to and/or from the biological tissue portion. The system may further include a magnetic element, which may be selected from a group consisting of: a magnet, a toroid, a conductive coil, a magnetic powder, and a magnetic fluid.

In some embodiments, a method of applying and/or receiving an electrical signal via a biological tissue portion may be provided. The method may include positioning a first system proximate a biological tissue portion. In some embodiments, the system may include a first body and a first conductor, which may be configured to be electrically coupled to at least one of a power source and a detector. In some embodiments, the first system may include a first electrode, which may include a surface configured to contact a first biological tissue portion and apply and/or receive an electrical signal to and/or from the first biological tissue portion. In some embodiments, the first system may include a first magnetic element, which may be selected from a group consisting of: a magnet, a toroid, a conductive coil, a magnetic powder, and a magnetic fluid. In some embodiments, the method may include placing the first magnetic element proximate the first biological tissue portion. In some embodiments, the method may include using the first electrode to apply and/or receive an electrical signal via the first biological tissue portion. In some embodiments, a first energy field applied by the first electrode may be distributed in a different pattern than the first energy field would have been distributed if the first magnetic element were not present.

In some embodiments, a device for sending a stimulus or challenge based on decentralized network parameters is communicated, while said device also records the user's modulated response, where the response is a function of both the time-dependent stimulus and the biological make-up of a person.

In some embodiments, a decentralized network for communicating and reaching consensus on the features within biological data may be constructed. In some embodiments, a step for anonymizing the biological data may be implemented. In some embodiments, the biological data is modulated based on a person's biometricity and current network parameters. In some embodiments, an algorithm for determining the identity or other general feature of biological data is performed by a hashing protocol spread over multiple decentralized nodes. This hashing protocol rewards the first node to correctly classify the data in a decentralized way, while penalizing those who make incorrect suggestions based on the biological data. In some embodiments, consensus is achieved through a voting protocol that may weight some well-trusted nodes more than others, where these well-trusted nodes may also test the network by submitting slight modulations of previously-seen data.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

Figure 1:
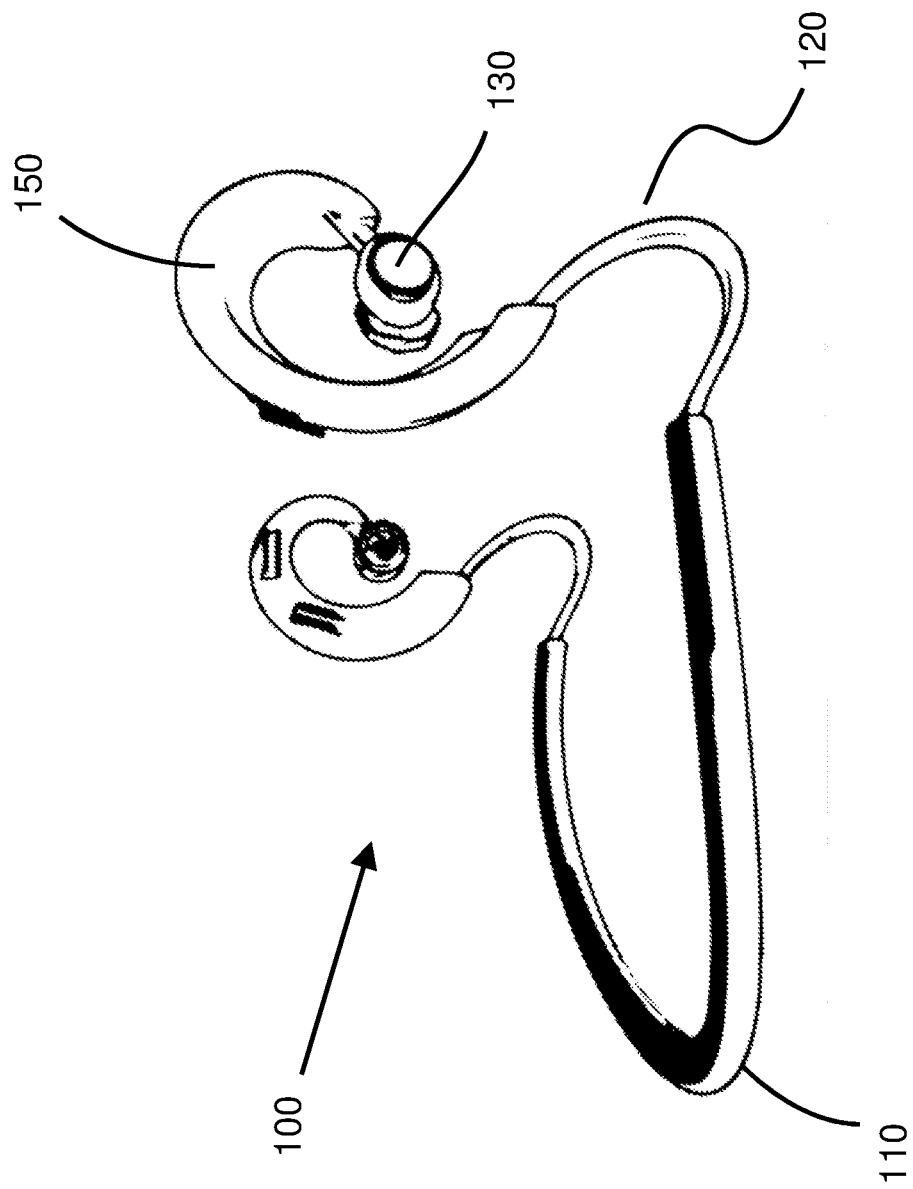
FIG. 1 illustrates an exemplary system 100 for applying and/or receiving signals according to some embodiments.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

As used herein, the terms "optional" and "optionally" mean that the subsequently described, component, structure, element, event, circumstance, characteristic, property, etc. may or may not be included or occur and that the description includes instances where the component, structure, element, event, circumstance, characteristic, property, etc. is included or occurs and instances in which it is not or does not.

A magnetoelectric effect may occur where a substantial magnetic field emanating from a dedicated magnetic device (such as a strong polarized magnet, toroid, or other structure) is used to alter or reduce the impedance of a structure prior to the application of a signal. A magnetoelectric signal may differ from an electrical signal by the altered paths it takes through a structure due to the presence of one or more magnetic devices. Magnetoelectric signals may be particularly advantageous when a magnetic device is applied to magnetically-diverse media such as biological materials, as these materials can have a number of dispersed magnetic materials that may have impedance affects due to the application of a dedicated magnetic field. Magnetoelectric signals may change internal impedances to direct magnetoelectric signals along different pathways through the biological structure, affecting particular internal structures. In this manner, magnetoelectric signals may offer superior targeting relative to purely electrical signals.

FIG. 1 illustrates an exemplary embodiment of a system 100 for applying and/or receiving signals. As illustrated in FIG. 1, the system may in some embodiments be arranged to be wrapped around a user's head in a manner similar to a pair of headphones. For example, the system may include a lateral member 110 which may be configured to be wrapped around a rear of a user's head. On each side of the lateral member 110 may be an earpiece 130, an arcuate member 150, and an elbow member 120. The lateral member 110 may be substantially resilient, and may be shaped and sized such that the lateral member 110 is resiliently expanded when the system 100 is placed on a user's head. In this manner, the lateral member 110 may provide a biasing spring force to assist in maintaining engagement between inward facing surfaces of the system 100 and the user's skin. Likewise, the elbow members may be made from a resilient material to maintain this biasing force. Using resilient materials in the lateral member and/or elbow members 120 may additionally promote user comfort by allowing a mechanism to readily adjust the size and fit of the system.

In some embodiments, the arcuate members 150 may be sized and shaped to wrap around a rear of a user's ear. In some embodiments, the earpieces 130 may be sized and shaped to be place within a user's ear. In some embodiments, one or more of the earpieces 130 may include speakers to convey media or other auditory information to a user. Exemplary embodiments of the earpiece 130 and arcuate member 150 are discussed in greater detail below.

Figure 2:
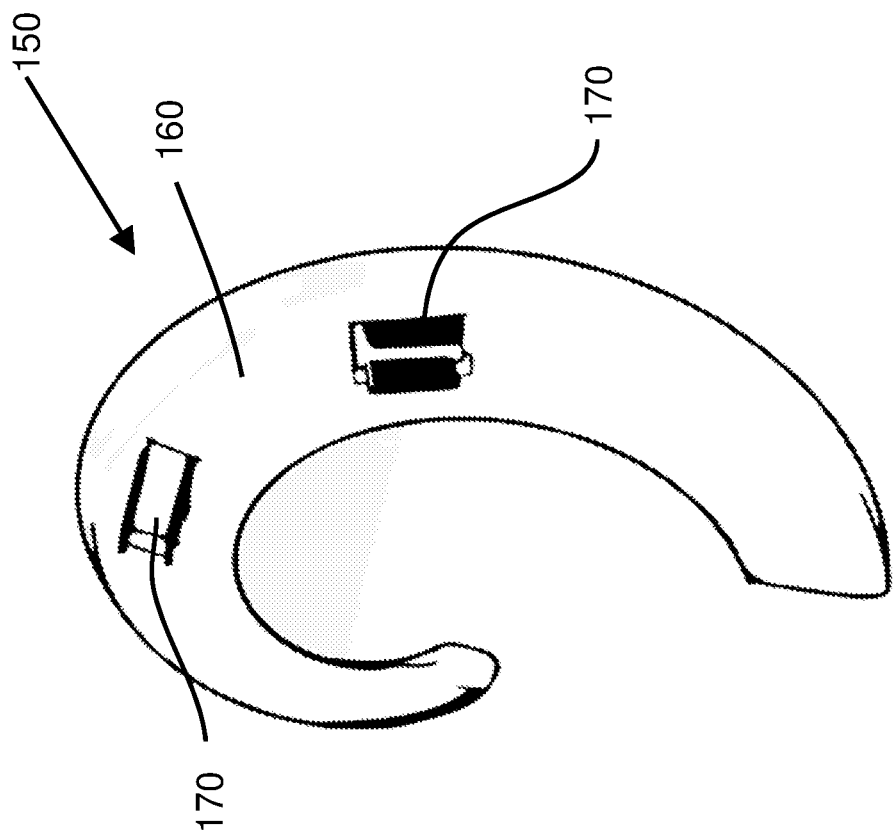
FIGS. 2 and 2A illustrate exemplary systems according to some embodiments.

FIG. 2 illustrates an exemplary embodiment of an arcuate member 150. In some embodiments, the arcuate members (of left over-ear and right over-ear pieces), may constitute the only structure of the device, without a wire or other structure connecting them. As illustrated in FIG. 2, the arcuate member may include a body 160 and one or more filament groups 170. Each filament group 170 may include one or more filaments. The filaments may be electrically conductive. In some embodiments, the filaments may be carbon fibers. The filaments may extend outwardly relative to a surface 162 of the body 160 such that the filaments may contact a biological tissue portion (e.g., a user's skin) when the surface 162 abuts the biological tissue portion. In some embodiments, the filaments may extend outwardly relative to the body in substantially the same direction such that a tip end of each filament may contact a substantially flat tissue portion without changing an orientation of the body. In some embodiments, for example, the arcuate member 150 may be placed around the rear of a user's ear such that one or more of the filaments of the filament groups 170 may contact the user's skin behind the user's ear and below the user's hair line.

In some embodiments, one, two, three, four, five, six, or more filament groups may extend from a single body 160. In some embodiments, the filaments of each group may be arranged substantially linearly or as one or more continuous groupings. In other embodiments, the filaments of each group may be substantially curvilinear, and the curvature of the filaments may optionally substantially match a curvature of the body 160. For example, the curvature of a filament group may be selected to substantially match the curvature of an arcuate member to which the filament group is coupled.

Figure 2A:
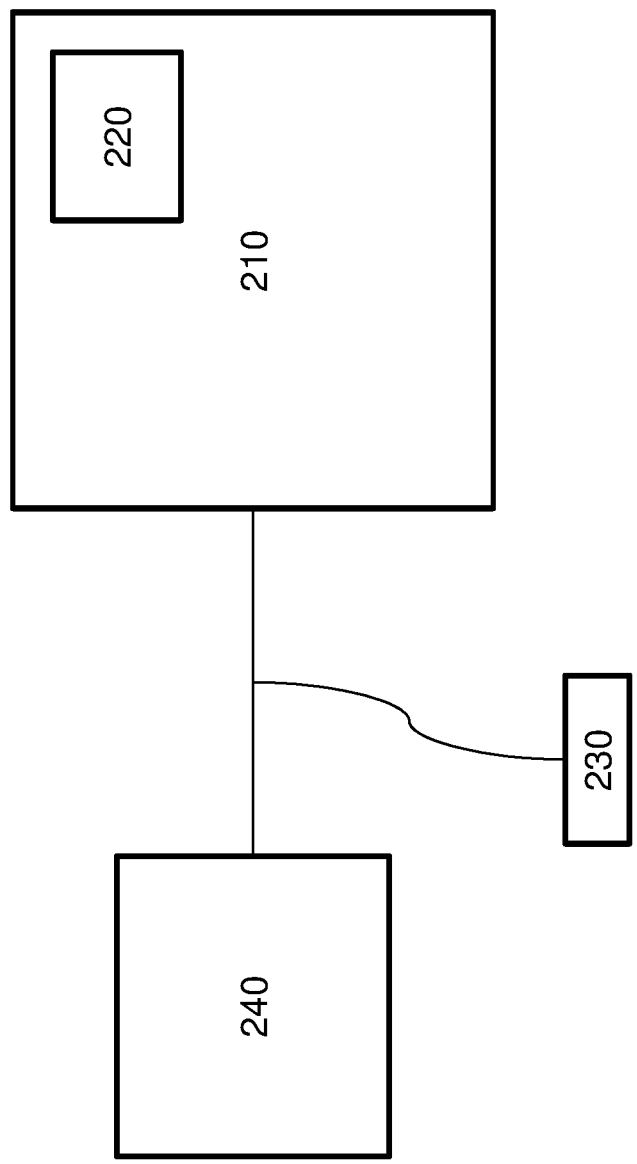

FIG. 2A illustrates an exemplary embodiment of a system such as those described above and below. The system may include a body 210, an electrode 220, a conductor 240, and a power source/detector 240. The body 210, electrode 220, conductor 240, and power source/detector 240 may be as described with respect to the other embodiments described herein. For example, the body 210 may optionally be shaped to be disposed around or within a user's ear, or alternatively, may be configured to be deformable to be wrapped around a portion of a user's body. Likewise, the electrode 220 may optionally be embodied as one or more conductive filaments or any other suitable arrangement.

Figure 3:
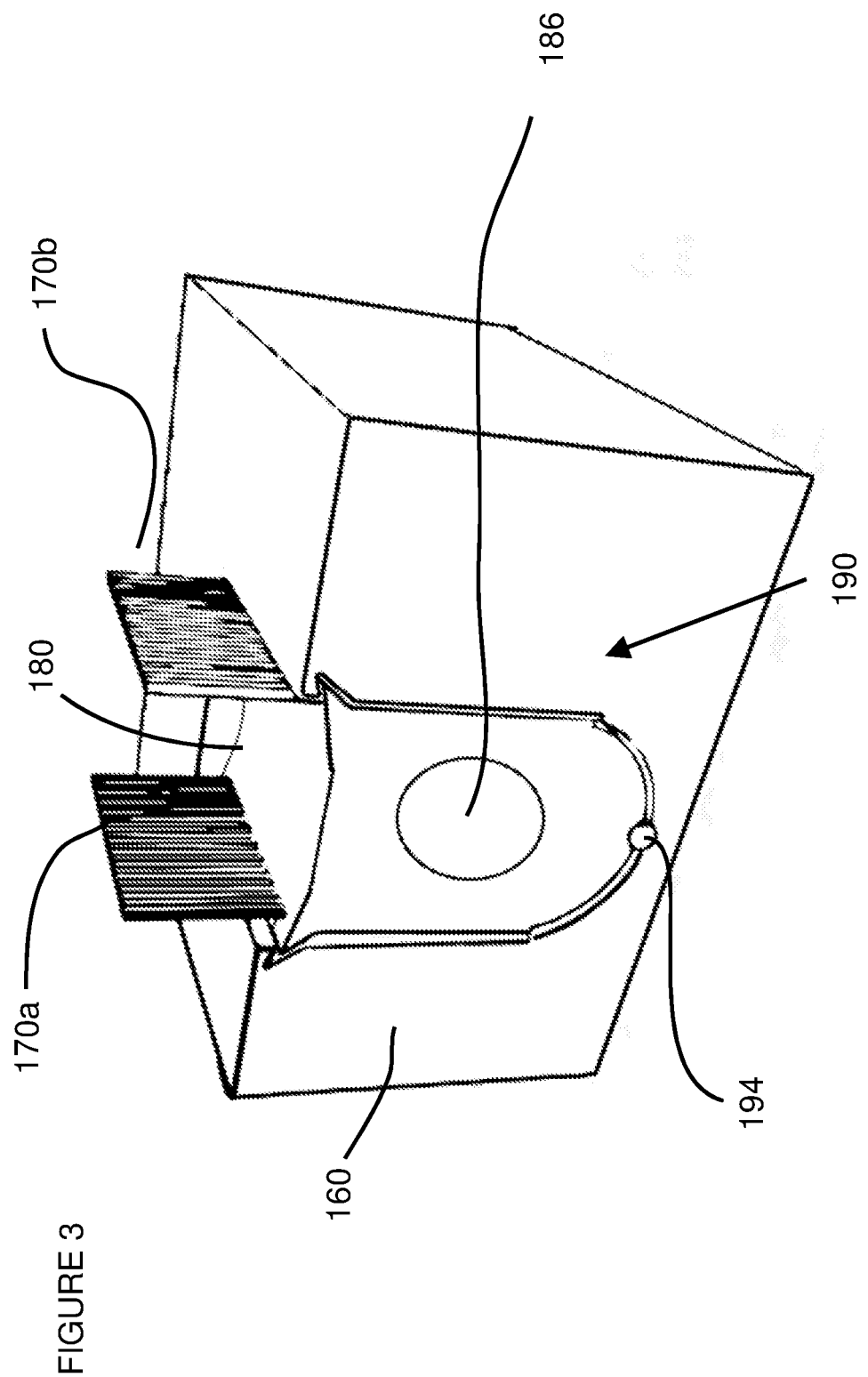
FIGS. 3-5 illustrate exemplary arrangements for securing filaments to a body according to some embodiments.

FIG. 3 illustrates an exemplary embodiment in which filament groups 170a, 170b may be retained in a body 160 via use of anchor 180. Although FIG. 3 depicts this technique being used in a body 160 such as that illustrated in the embodiment of FIG. 2, this is purely for simplicity of explanation and should not be construed as limiting in any way. Rather, this anchoring technique can be used in any suitable system as will be apparent to those of skill in the art upon reviewing the present disclosure. As illustrated in FIG. 3, one or more filaments may be disposed around an anchor 180, which may be inserted and retained within a cavity 190 in the body 160. In some embodiments, a portion of a conductor 194 (e.g., a wire, circuitry, or other conductive member) may be disposed within the cavity 190 in a position such that the conductor 194 may contact a portion of the filaments or anchor. In this manner, signals may be transmitted from the conductor to the filament and then to the tissue, and/or from the tissue to the filament and then to the conductor. The conductor 194 may be partially enclosed within the body 160 and may extend through the length of the body 160 to couple the filament groups 170 to a power source or detector (see, e.g., FIG. 2A).

In some embodiments, a magnetic element 186 may optionally be disposed within the anchor 180. In some embodiments, the magnetic element include a magnet, a toroid, a conductive coil, a magnetic powder, a magnetic fluid, or any other suitable arrangement for generating magnetic fields. In some embodiments, a magnetic element 186 may be placed within the body 160. For example, one or more magnetic elements 186 may be placed adjacent to one or more cavities 190. In some embodiments, the magnetic element 186 may be arranged such that it will be proximate the biological tissue portion when a filament contacts the biological tissue portion such that an energy field applied by the filament is distributed in a different pattern than the energy field would have been distributed if the magnetic element were not present. In this manner, energy may be directed along different pathways through the biological structure, thereby targeting desired internal structures.

In some embodiments, the conductor may be coupled (directly or indirectly) to a power source or other source of electrical/magnetoelectric/vibratory/electromagnetic stimulus. In this manner, a stimulus may be applied to the conductor, which may be transmitted to the filament groups 170 (optionally via one or more additional elements such as circuitry within a body 160 and/or an anchor 180 as discussed below), and then to a biological tissue portion. In some embodiments, the conductor may be coupled to a detector or measurement circuit. In this manner, electrical activity within the user's body (e.g., within a central nervous system, peripheral nervous system, or musculature) may be transmitted from a biological tissue portion to the filament groups 170, to the conductor (optionally via one or more additional elements such as circuitry within a body 160 and/or an anchor 180 as discussed below), and then to the detector. Thus, the system may be used for stimulation, measurement, or both.

Figure 4A:
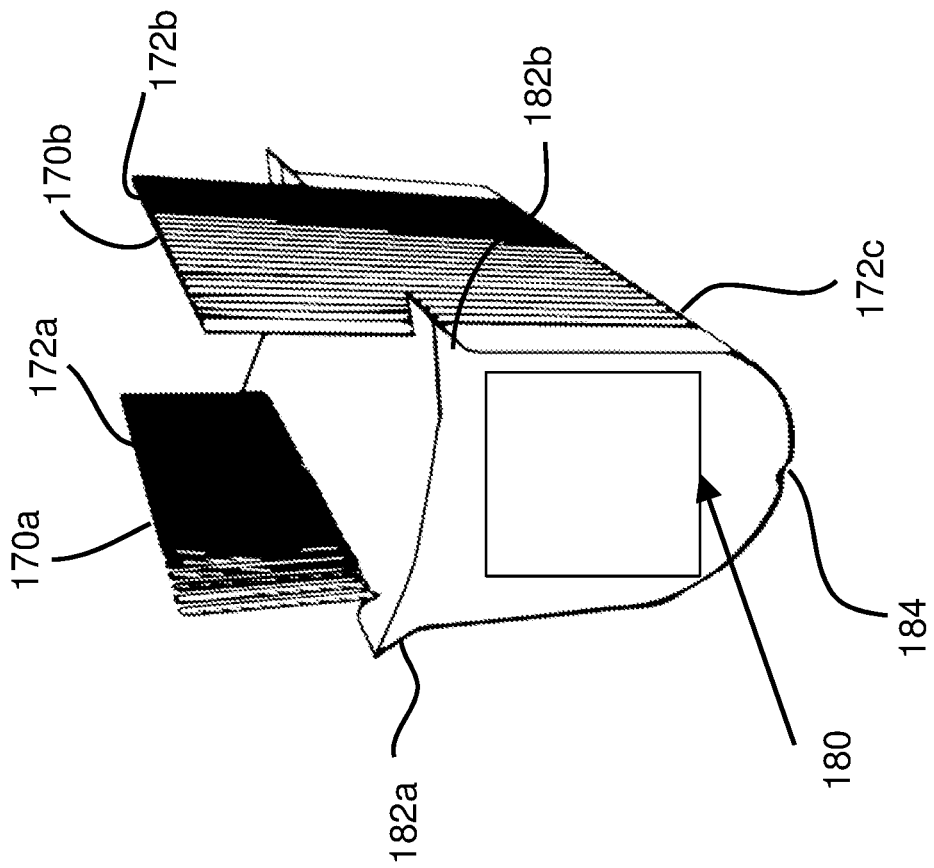

FIG. 4A illustrates an exemplary embodiment of an anchor 180. Here, the filament groups 170a, 170b are shown including a plurality of individual filaments 172. In some embodiments, a given filament may include a first tip end 172a and a base portion 172c. In some embodiments, the filament may further include a second tip end 172b. The tip ends 172a, 172b may extend outwardly from the anchor 180 (and the body 160 when the anchor 180 is retained within the body) such that the tip ends 172a, 172b are arranged to contact a biological tissue portion when the system is in contact with a user's body. In some embodiments, the base portion 172c may be arranged between the first tip end 172a and the second tip end 172b. In some embodiments, the base portion 172c may be disposed around a portion of the anchor 180. For example, the base portion 172c may wrap around a lower portion of the anchor between the two tip ends 172a, 172b. In some embodiments, the base portion may be arranged to contact a conductor, such as the conductor 194 illustrated in FIG. 3. In some embodiments, the anchor 180 may include a recess 184 which may be shaped to receive a portion of the conductor 194.

Figure 4B:
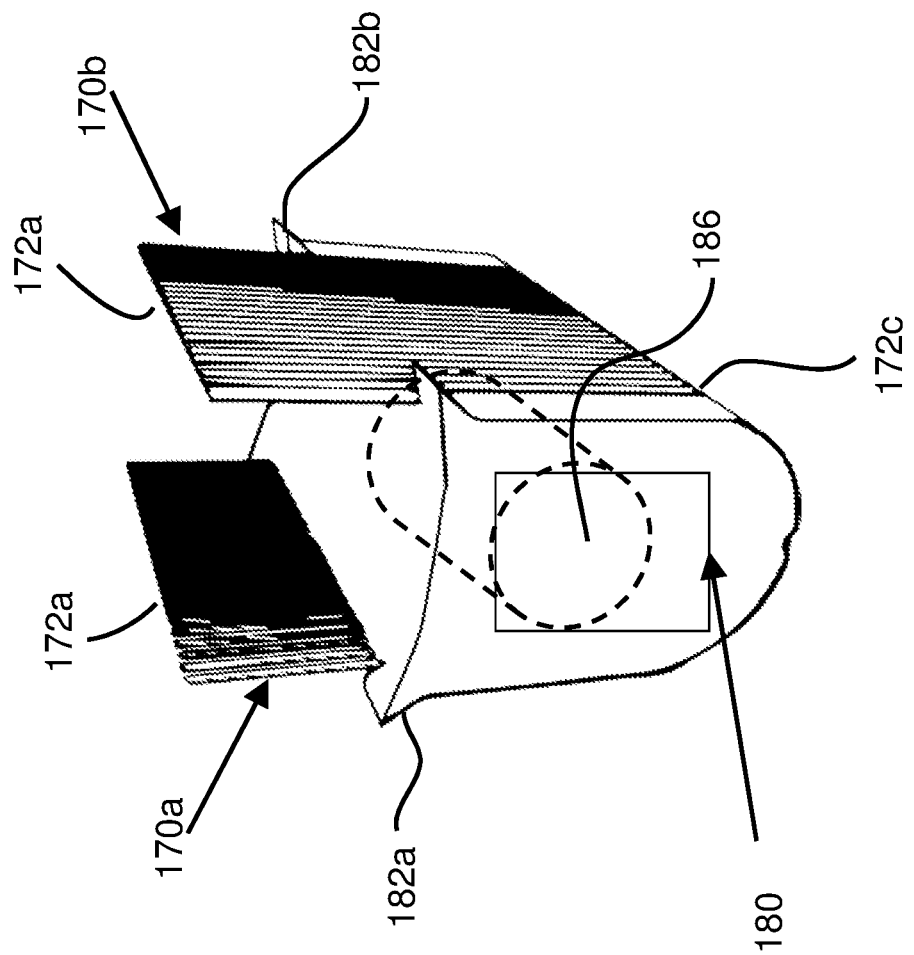

As illustrated in FIGS. 4A and 4B (and also with reference to FIGS. 3 and 5), in some embodiments, the anchor 180 may be configured to be snap-fit into a cavity 190 in the body 160. For example, the anchor 180 may include one or more projections 182a, 182b. The projections 182a, 182b may be resilient members. Moreover, the projections 182a, 182b may be sized and shaped to be placed within recesses 192a, 192b in the cavity 190 (see, e.g., FIG. 5). In some embodiments, the projections 182 and recesses 192 may have complementary shapes. In some embodiments, the arrangement of projections and recesses may be inverted relative to the arrangement shown in FIGS. 3-5, such that recesses are instead provided on the anchor 180 and projections are provided in the cavity 190. This arrangement similarly permits a resilient snap-fitting function.

FIG. 4B illustrates another exemplary embodiment of an anchor 180. This embodiment includes features similar to that illustrated in FIG. 4A, including filament groups 170, filaments having first tip ends 172a, second tip ends 172b, and base portions 172c, and projections 182a, 182b. As illustrated in FIG. 4B, a magnetic element 186 may be disposed within the anchor 180. In some embodiments, the magnetic element include a magnet, a toroid, a conductive coil, a magnetic powder, a magnetic fluid, or any other suitable arrangement for generating magnetic fields. FIGS. 4A and 4B also illustrate embodiments in which the projections 182 may be provided at an end of an anchor 180, such that the projections may be disposed beyond the portion of the anchor upon which the filaments extend. In this manner, interference between the snap-fitting mechanism and the filaments may be avoided.

In some embodiments, the anchor 180 may be formed from a conductive material. One exemplary material that has been found to perform well is conductive plastics, such as conductive PLA, and conductive silicone made from chopped conductive microfibers, but other materials may also be used. By forming the anchor from conductive material, the need to directly contact a conductor in the body 160 to the filaments may be obviated. For example, a conductor may instead contact a portion of the conductive anchor 180, which may in turn contact the filaments. In this manner, the filaments may be electrically coupled to the conductor via the anchor 180. In some embodiments, a circuit board may be arranged within the body such that electrical contacts extend to each cavity 190 at a position where the anchor 180 may be electrically coupled with the circuit board upon placement into the cavity 190. In some embodiments, permitting electrical current to flow through the anchor may additionally permit manipulation of a magnetic field generated back the magnetic element 186.

Figure 5:
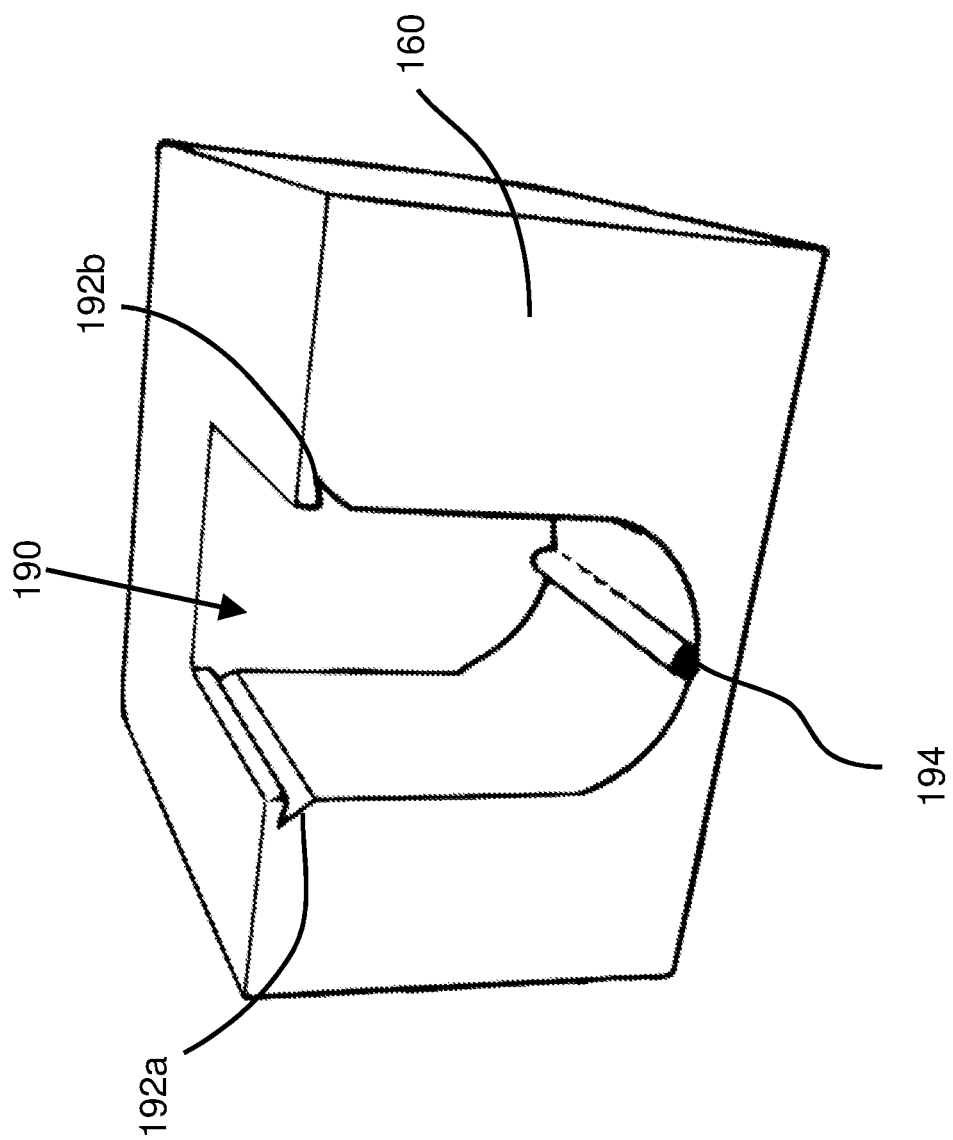

FIG. 5 illustrates an exemplary embodiment of a cavity 190. As explained above, the cavity 190 may be shaped to receive an anchor 180. For example, the anchor 180 and cavity 190 may have complementary shapes and sizes. In some embodiments, the cavity may include recesses 192a, 192b, which may be sized and shaped to receive projections on the anchor 180. In some embodiments, the cavity 190 may include a conductor 194. The conductor 194 may be arranged within the cavity 190 such that it may contact filaments 170 and/or the anchor 180.

As will be apparent from FIGS. 2-5 and the accompanying disclosure, any number of anchors may be coupled to any number of recesses on a given body. For example, the arcuate portion 150 shown in FIG. 2 depicts two anchors operatively attached to two recesses, with the result that four filament groups 170 are provided. Any desired number and arrangement of filament groups and/or snap-fitting arrangements may be used.

Figure 6:
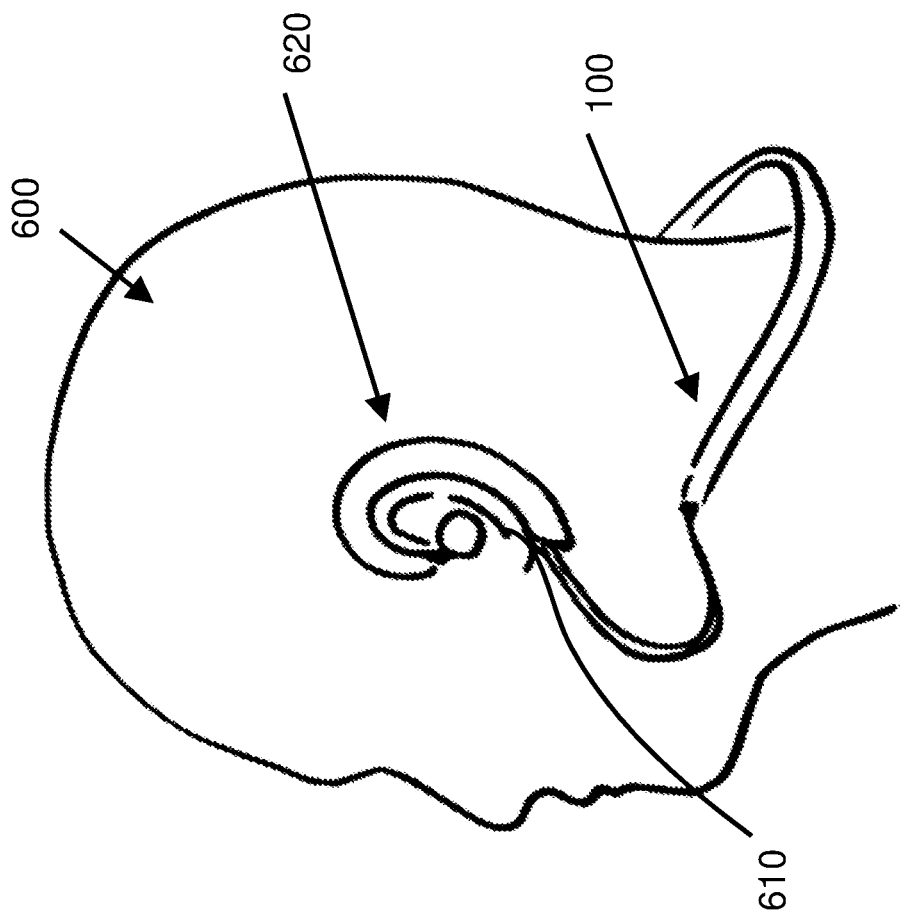
FIG. 6 illustrates an exemplary headphone-type system being worn on a user's head according to some embodiments.

FIG. 6 illustrates an exemplary embodiment of a headphone-type system 100 being worn on a user's head 600. In the illustrated embodiment, an arcuate portion 150 is disposed behind a user's ear 610. One or more groups of filaments 170 may be in contact with a biological tissue portion 620. In the illustrated example, this biological tissue portion 620 may be a portion of the user's skin behind the user's ear 610. As shown in FIG. 6, the earpiece 130 may be disposed within the user's ear 610 at the same time that the filaments 170 are in contact with the biological tissue portion 620. In this manner, the system may play media and provide stimulus and/or measure electrical activity in the user's body simultaneously.

Figure 7:
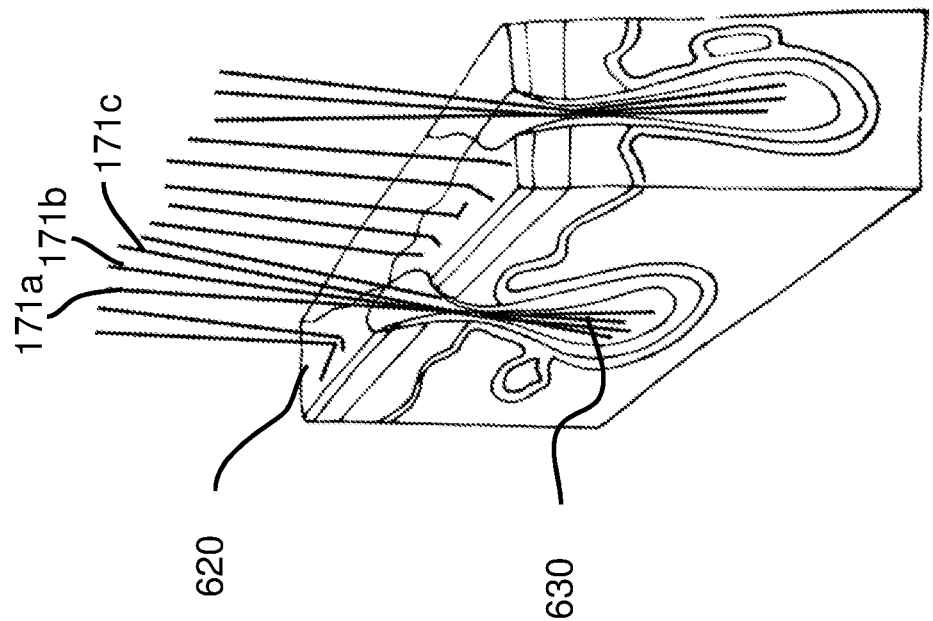
FIG. 7 illustrates an exemplary biological tissue portion according to some embodiments.

FIG. 7 illustrates an exemplary biological tissue portion 620. As shown, the biological tissue portion 620 may be a portion of a user's skin. In other embodiments, the system may be placed in contact with other portions of a user's body, such as underneath the skin or in contact with organs or muscles. Where the biological tissue portion 620 is a portion of the user's skin, it may be a skin portion behind a user's ear. In other embodiments, skin elsewhere on a user's body may be selected (see, e.g., FIGS. 12-17).

As shown in FIG. 7, a biological tissue portion may include one or more pores 630. Skin pores, for example, typically have a diameter on the order of 10-50 microns. The tip ends of the filaments (or the entire length of the filaments) may have a width of less than 50 microns. In some embodiments, the filaments may have a width less than 15 microns, less than 10 microns, or less than 5 microns. Thus, one or more filaments 171a, 171b, 171c, may be partially disposed within a pore 630. In some embodiments, the tip ends of one or more filaments may be disposed within the pore 630 when the system 100 is placed on a user's head as illustrated in FIG. 6. In some embodiments, two, three, four, five, six, or more filaments may be partially disposed within a single pore 630 at a time. Still other filaments may contact an external surface of the user's skin. By contacting the user's skin and/or by extending within a pore, excellent electrical contact may be established between the filaments and the user's body. Often, the first layer of skin represents a substantial portion of the impedance between an external electrode and a portion of a user's body to be measured or stimulated. By improving contact and/or bypassing this first layer of skin, impedance may be substantially reduced. This provides an improvement to signal-to-noise ratio and improves safety by permitting stimulation to be applied at lower voltages.

Figure 8:
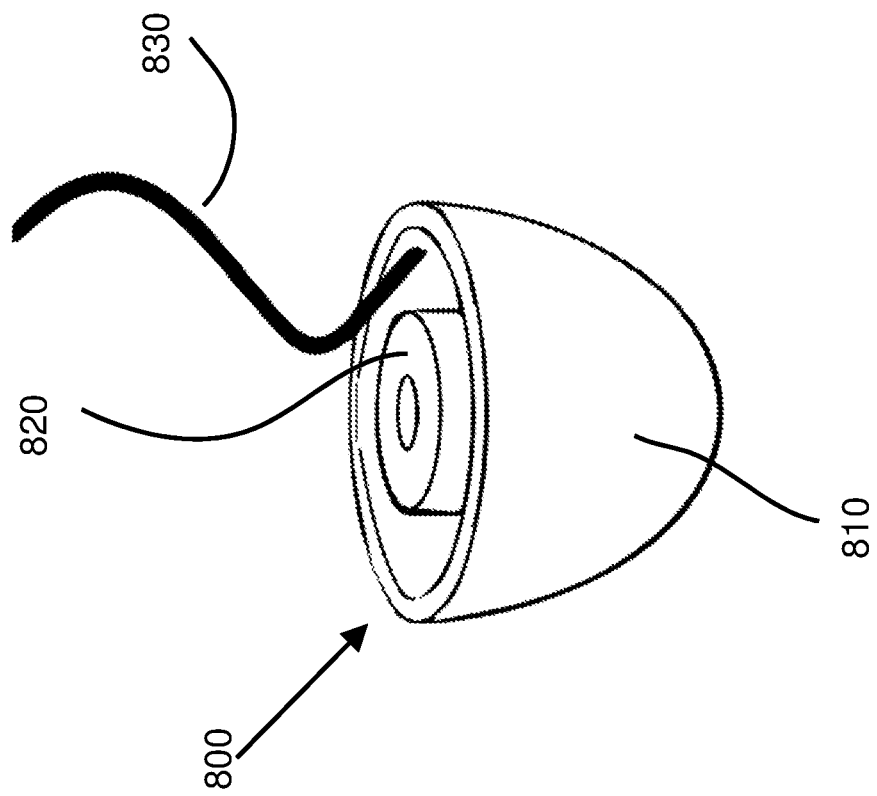
FIGS. 8 and 9 illustrate exemplary systems for applying and/or receiving signals within a user's ear according to some embodiments.

FIG. 8 depicts an exemplary embodiment of a conductive tip 800 that may be used, for example, to apply or receive signals within a user's ear. The conductive tip 800 may be made from a conductive material, including but not limited to conductive plastics. In some embodiments, the conductive material may have a modulus of elasticity less than 3.5 GPa. By employing a material having a modulus of elasticity in this range, elastic flexibility may be provided, which may advantageously promote comfort and better retain the tip 800 in the user's ear. In some embodiments, the tip 800 may include an outer surface 810. The outer surface may be shaped to engage an inner portion of a user's ear. For example the outer surface 810 may approximate a portion of a sphere or cone. In some embodiments, the conductive tip 800 may include a channel 820. The channel may be substantially centered within the outer surface and may define a hollow interior through which air and/or sound waves may pass. In some embodiments, an optional conductor 830 may be arranged to contact a portion of the conductive tip 800, such as the outer surface 810 and/or channel 820.

Figure 9:
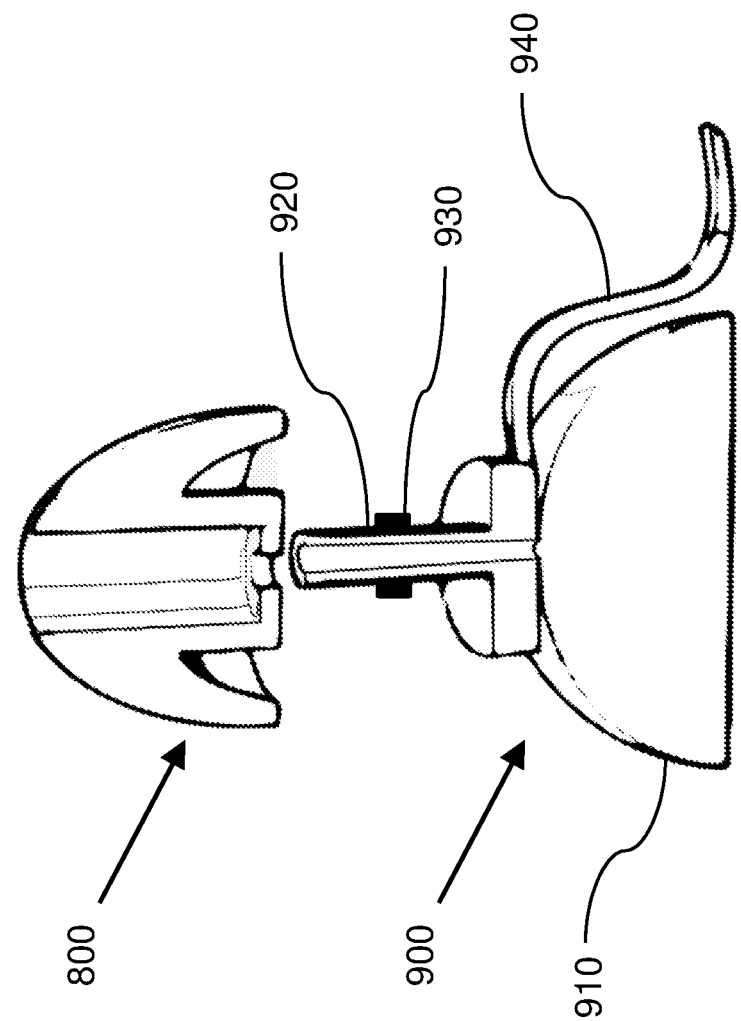

FIG. 9 depicts an exemplary embodiment of a system for applying and/or receiving a signal within a user's ear. The system may include a conductive tip 800, as generally described with respect to FIG. 8, and a base 900. The base 900 may include a body 910, which may house a speaker and/or other circuitry. The base 900 may also include a magnetic element, which may be as described in any of the embodiments discussed herein. The base 900 may further include a projection 920 which may be sized and shaped to engage a portion of the channel 820. A speaker may be arranged within the base 900 such that the speaker may transmit sound waves through the hollow interior of the channel 820 when the projection 920 is engaged to the channel 820. An electrical contact 930 may be electrically coupled, directly or indirectly, to a conductor 940 (e.g., a wire). The electrical contact 930 may be placed along a portion of the projection 920 such that the electrical contact 920 engages a wall of the channel 820 when the channel is placed over the projection 920. The conductor, 940, may extend along the internal cavity of the body, 910.

To facilitate this engagement, the channel 820 (and optionally the entire conductive tip 800) may be formed from a resilient material and slightly undersized relative to the projection 920 and/or electrical contact 930. For example, an inner diameter of the channel may be less than an outer diameter of the projection 920 and/or electrical contact 930. In this manner, when the channel 820 is engaged to the projection 920, the channel 820 may expand slightly, presenting a biasing force to promote engagement between the channel 820, the projection 920, and the electrical contact 930. This biasing force may advantageously facilitate mechanical coupling between the base 900 and the conductive tip 800. Additionally, this biasing force may promote a reliable, low-impedance electrical coupling between the contact 930 and the conductive tip 800.

The conductive tip 800 may be a disposable unit. In the event that the tip 800 becomes damaged or otherwise exceeds its useful life, the tip 800 may be removed from the base 800 and replaced by another tip 800. In some embodiments, conductive filaments 840 such as those described above may optionally be embedded within the outer surface 810 of the tip 800. Permitting replacement of the tip 800 may also be advantageous in cases where the filaments become damaged, lose efficacy, or where the user otherwise desires to replace the tip or filaments.

Figure 10:
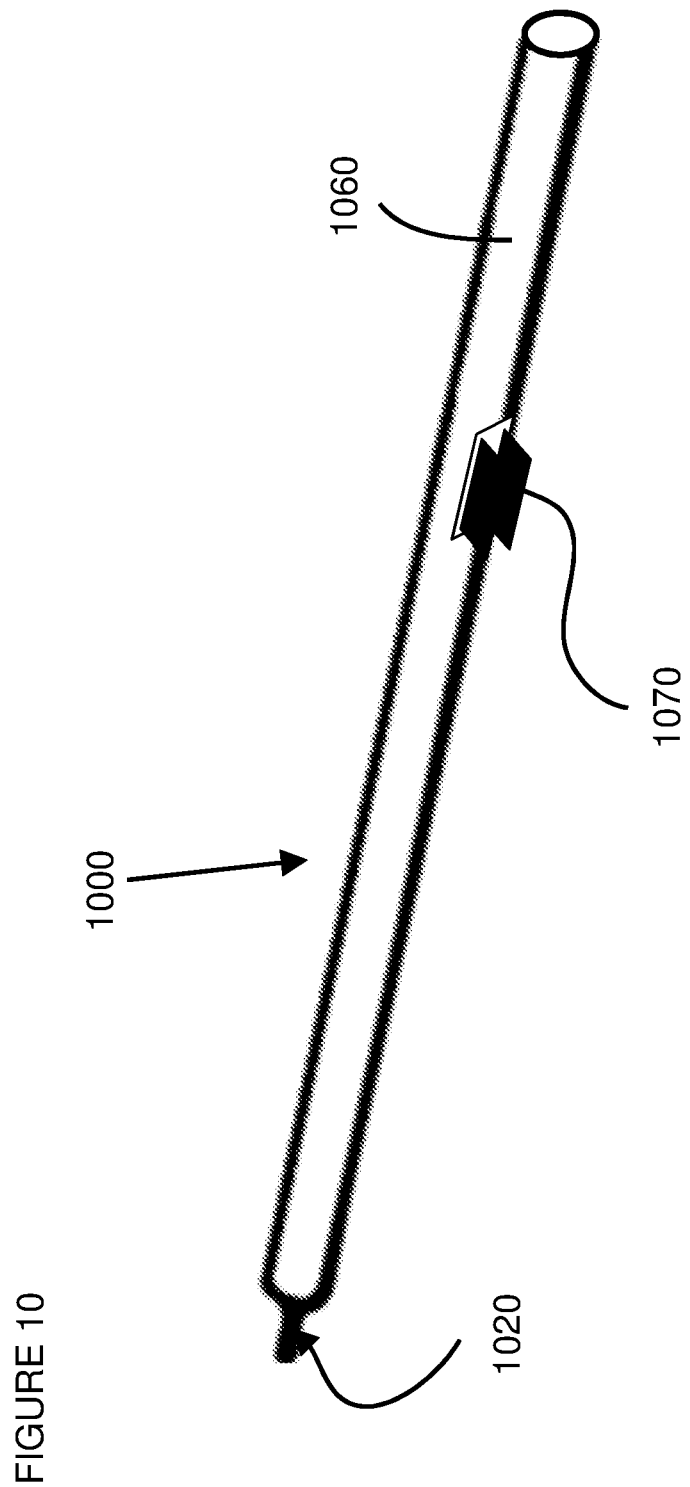
FIG. 10 illustrates exemplary systems for providing plastic deformation according to some embodiments.

FIG. 10 illustrates an exemplary embodiment of a deformable system 1000. In some embodiments, the system may include a body 1060 and a deformable member 1020. The deformable member 1020 may extend through all or a portion of the length of the body 1060, thereby providing a desired deformation characteristic along a selected portion of the body 1060. In some embodiments, the system may further include one or more electrodes 1070, which may optionally be embodied as filament groups 1070 or any other suitable conductive interface. In some embodiments, a conductor may couple to or be placed within the body 1060. In some embodiments, the conductor may be electrically coupled to the electrodes 1070. In some embodiments, the body may be made from a conductive material such as conductive plastics. In this manner, the entire body may act as an electrode through which signals may be applied or received. In other embodiments, one or more selected portions, such as optional filament groups 1070, may act as electrodes. In such embodiments, the remaining surface of the body 1060 may optionally be non-conductive. In some embodiments, the deformable member 1020 may provide improved plastic deformation and shape-retention characteristics. In some embodiments, the material of the body 1060 may be selected to provide the desired plastic deformation characteristics. In such embodiments, the deformable member 1020 may be optionally omitted.

In some embodiments, the deformation characteristic of the body may be such that when a proximal end of the body is fixed and a torque is applied to a distal end of the body such that the body exhibits 30 degrees of flexion relative to an original state, the body retains at least 10 degrees of deformation after the torque is removed. In some embodiments, the body 1060 may have a flexibility characteristic such that a torque less than or equal to 2.5 Newton-meters applied to a distal end of the body when a proximal end of the body is fixed produces at least 30 degrees of flexion. Permanent deformation and flexibility may also be desired in any of the embodiments discussed herein, and the selection of such a permanent deformation characteristic may also be applied to, e.g., the body 160 discussed above.

Figure 11:
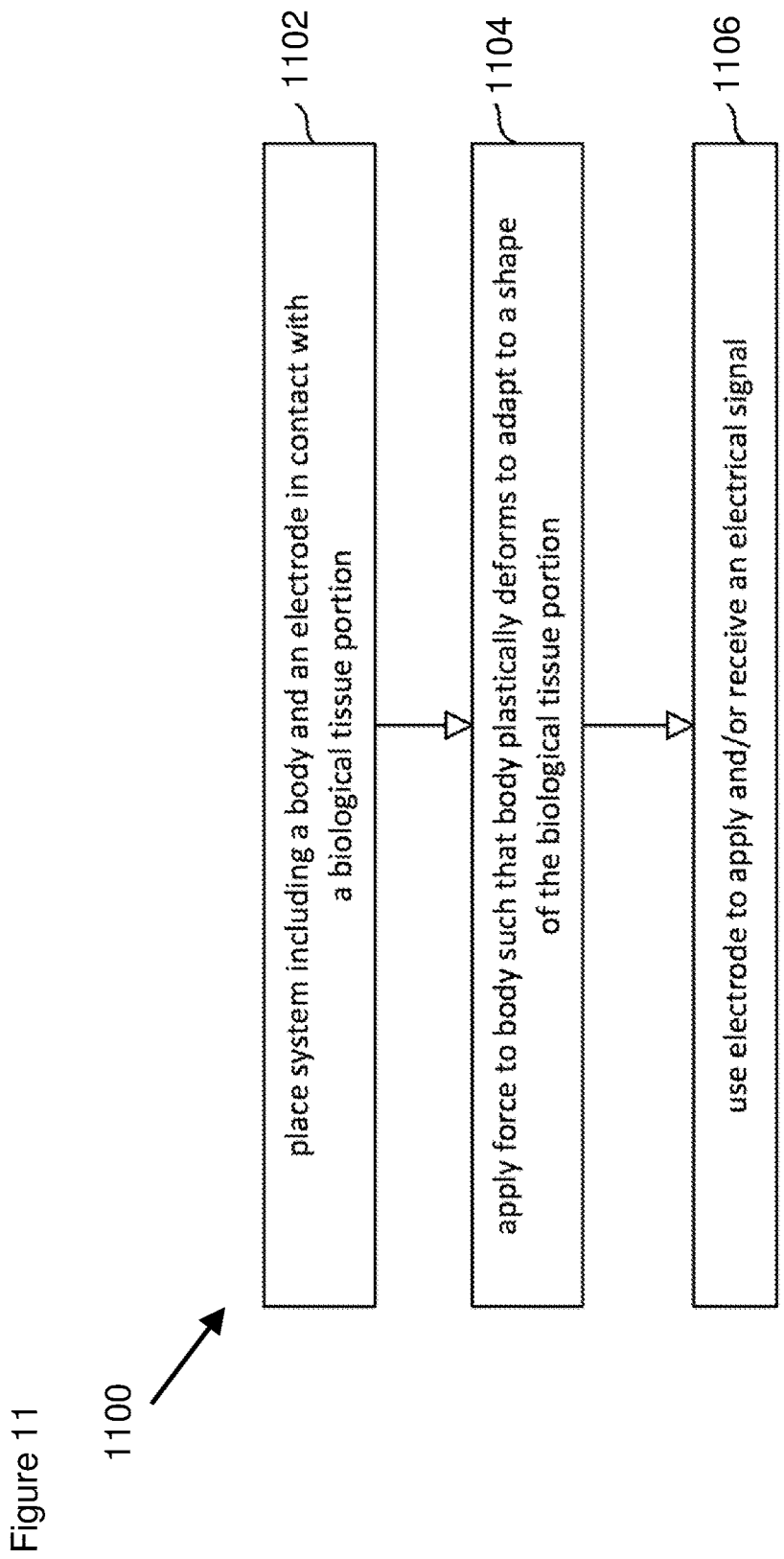
FIG. 11 illustrates an exemplary method for using a plastically deformable system according to some embodiments.

FIG. 11 illustrates an exemplary method 1100 for applying and/or receiving an electrical signal. Method 1100 may be used with any of the system embodiments described herein, including, for example, the deformable system embodiments described above with respect to FIG. 10. In step 1102, a system including a body and electrode may be placed in contact with a biological tissue portion. In some embodiments, the body may have a deformation characteristic such that when a proximal end of the body is fixed and a first torque is applied to a distal end of the body such that the body exhibits 30 degrees of flexion relative to an original state, the body retains at least 10 degrees of deformation after the first torque is removed. In some embodiments, the body may have a flexibility characteristic such that a second torque less than or equal to 1.3 Newton-meters produces at least 30 degrees of flexion when the second torque is applied. In step 1104, a force may be applied to the body such that the body may plastically deform to adapt to a shape of the biological tissue portion. For example, the force may result in the body being deformed from a first substantially straight configuration and a second substantially bent configuration. In some embodiments, the applying the force in step 1104 may include at least partially wrapping the body around a portion of the user's body. In some embodiments, the body may be wrapped around a user's ear, arm, hand, finger, leg, foot, toe, head, neck, back (e.g., lower back), pelvic floor, or penis.

In step 1106, the electrode may be used to apply and/or receive an electrical signal via the biological tissue portion. In some embodiments, for example, a stimulus may be transmitted from a conductor, to the electrode, and then to the biological tissue portion. In some embodiments, electrical activity within the user's body may be received at the electrode and transmitted through the conductor to a detector for measuring and analyzing the received signal. In some embodiments, stimulus and measurement may be performed simultaneously or in alternation.

Figure 12:
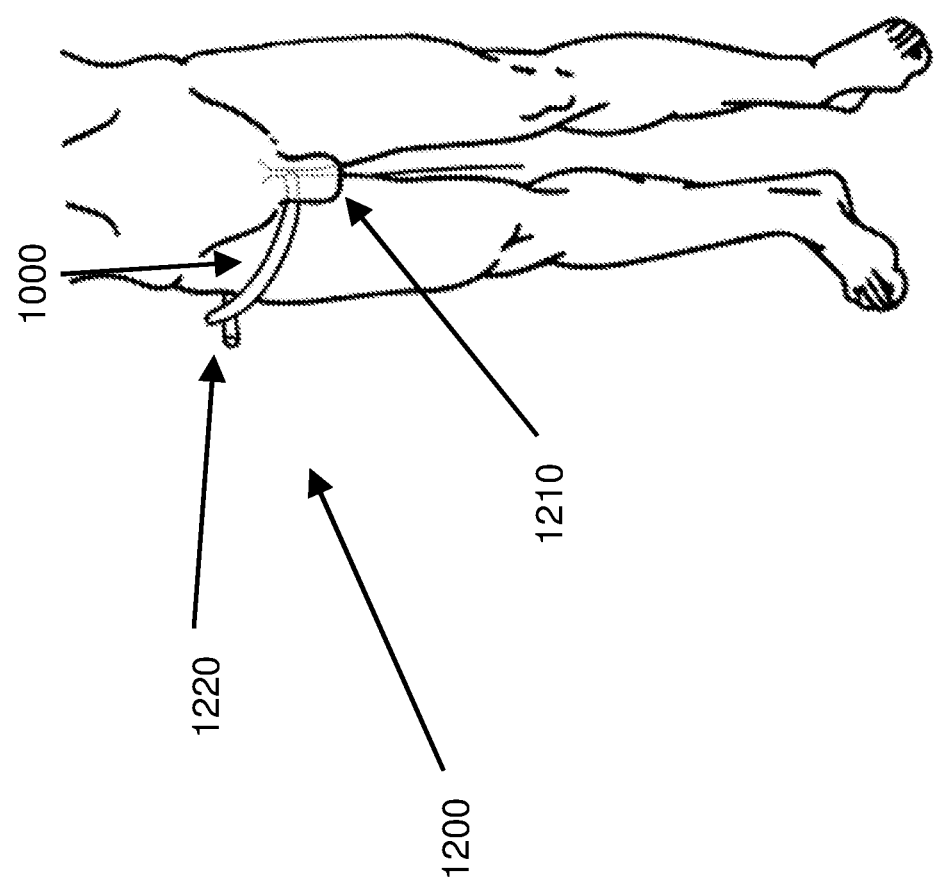
FIGS. 12-17 illustrate exemplary methods for using plastically deformable systems according to some embodiments.

FIG. 12 illustrates an exemplary aspect 1200 of the method 1100 described above with respect to FIG. 11. In some embodiments, the body 1060 may be aligned along a user's pelvic floor 1210 with the body 1060 wrapped around one of the legs. Any number of electrodes 1070 may be aligned along the deformable body 1060. The body 1060 may be applied in such a way that, after wrapping around a body part, the body is intertwined with itself in a tie or knot 1220.

Figure 13:
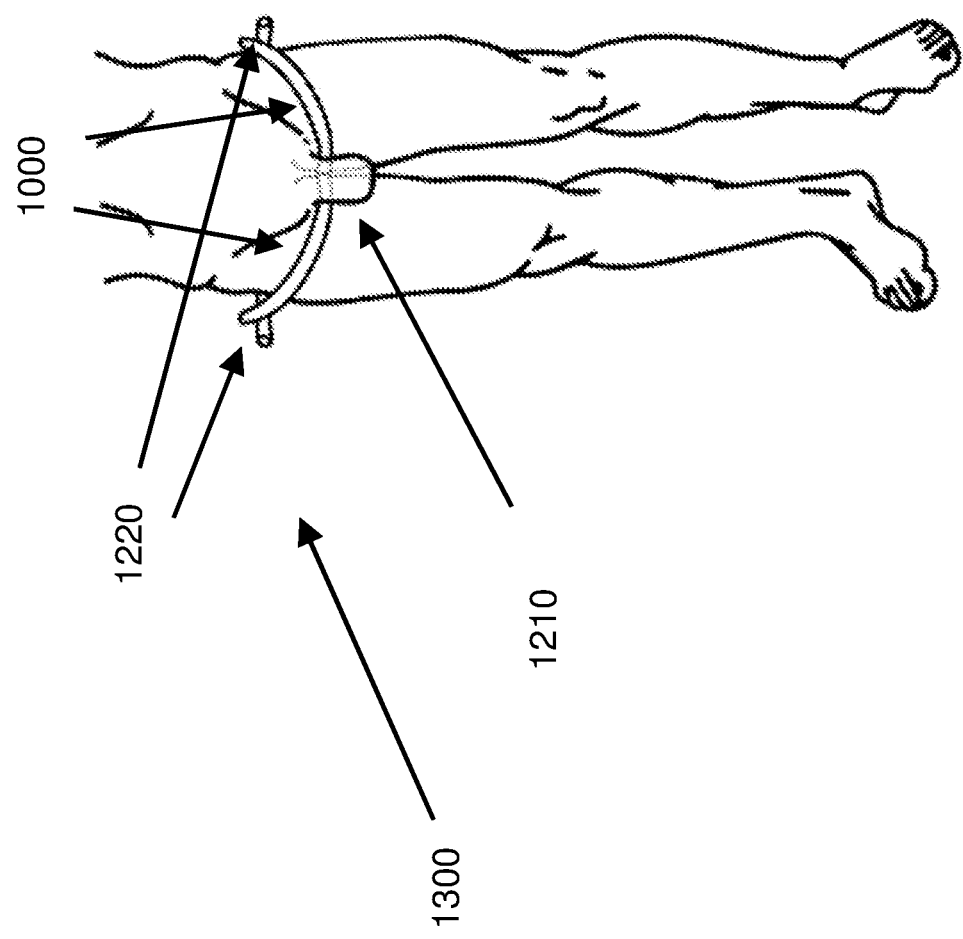

FIG. 13 illustrates an exemplary aspect 1300 of the methods described above with respect to FIGS. 11 and 12. In some embodiments, the system may include more than one of the systems 1000, the bodies of which may be aligned in two loops around the upper thighs. The deformable systems 1000 may be applied in such a way that, after wrapping around a body part, the body is intertwined with itself in a tie or knot 1120. The location one of the electrodes in the body systems 1000 may be aligned on the pelvic floor 1210, optionally with one or more than one electrode at this location to ensure functional connectivity. However, any number of electrodes may be aligned along the deformable bodies 1060.

Figure 14:
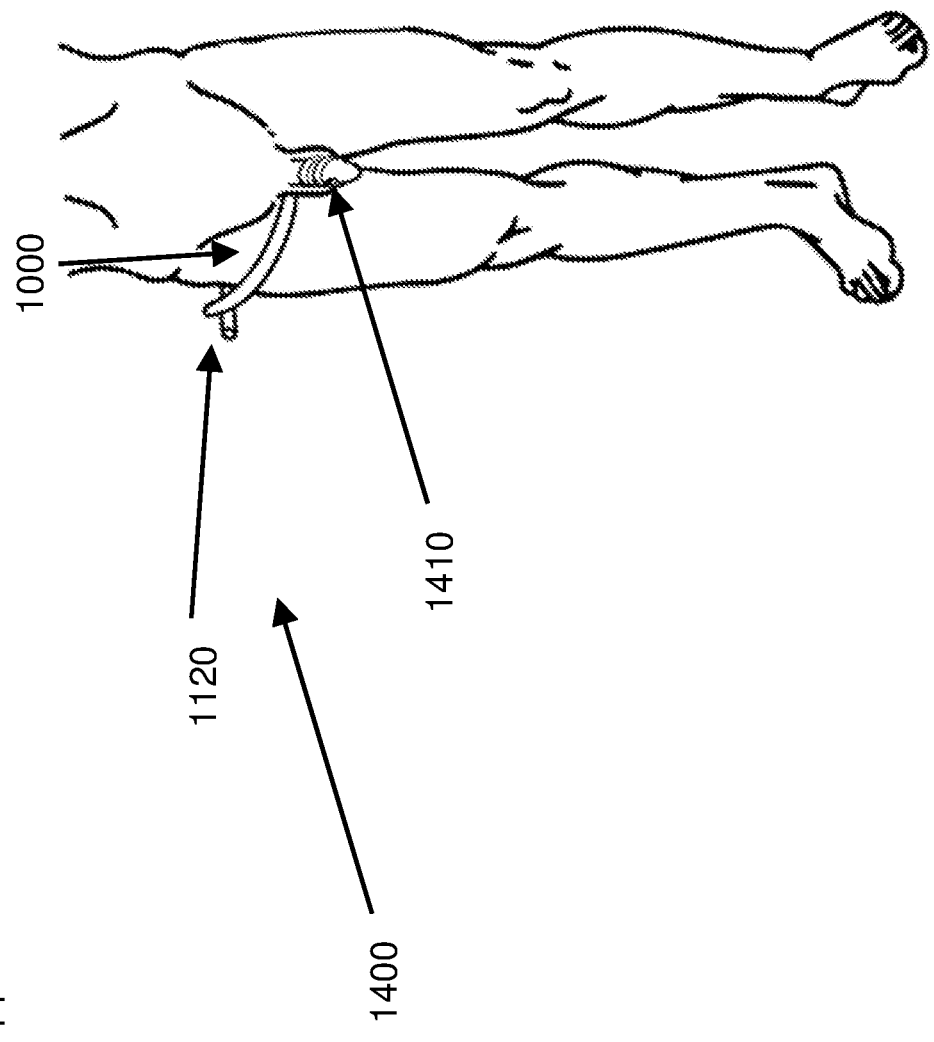

FIG. 14 illustrates an exemplary aspect 1400 of the method described above with respect to FIG. 11. In some embodiments, deformable system 1000 may be wrapped around a user's penis 1410 with one of the electrodes optionally aligned at this location.

Figure 15A:
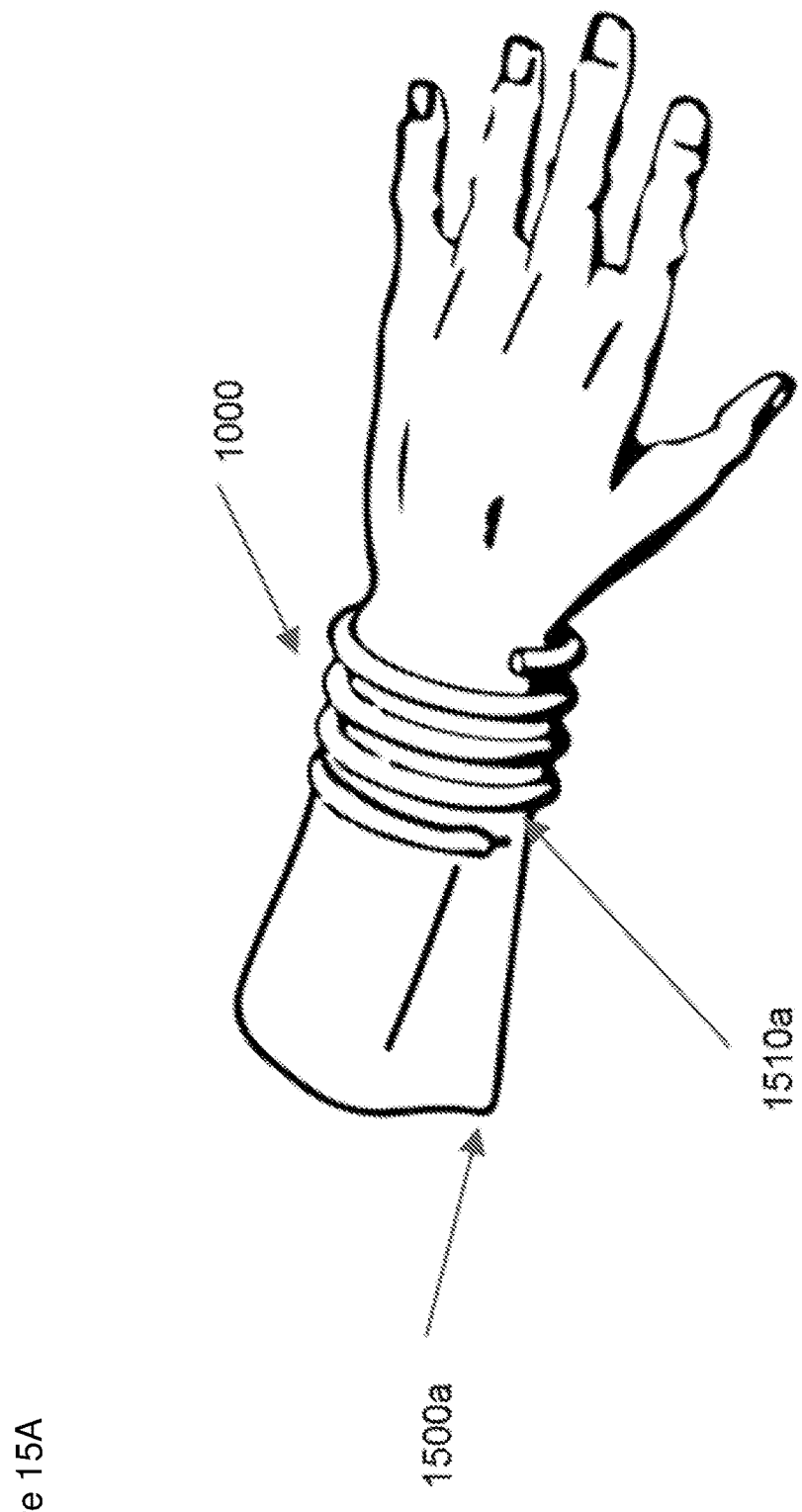
Figure 15B:
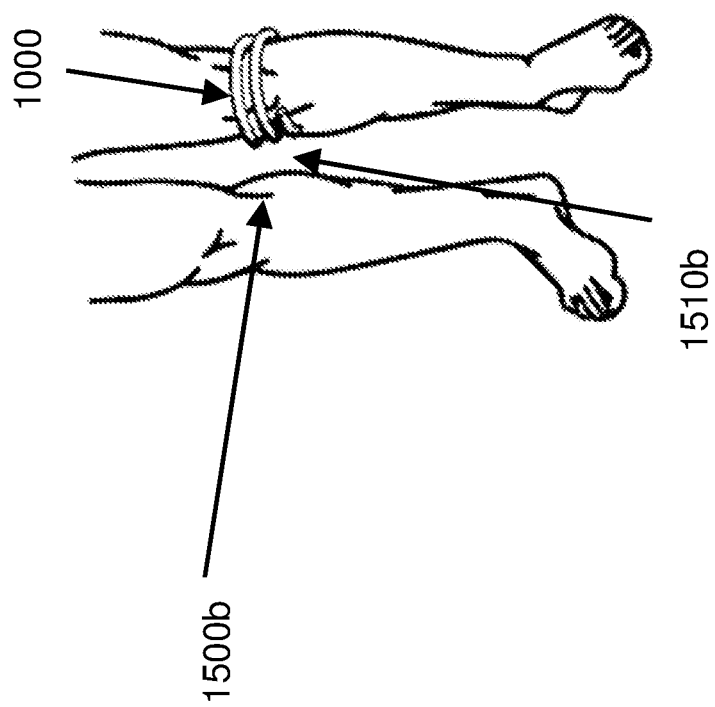
Figure 15C:
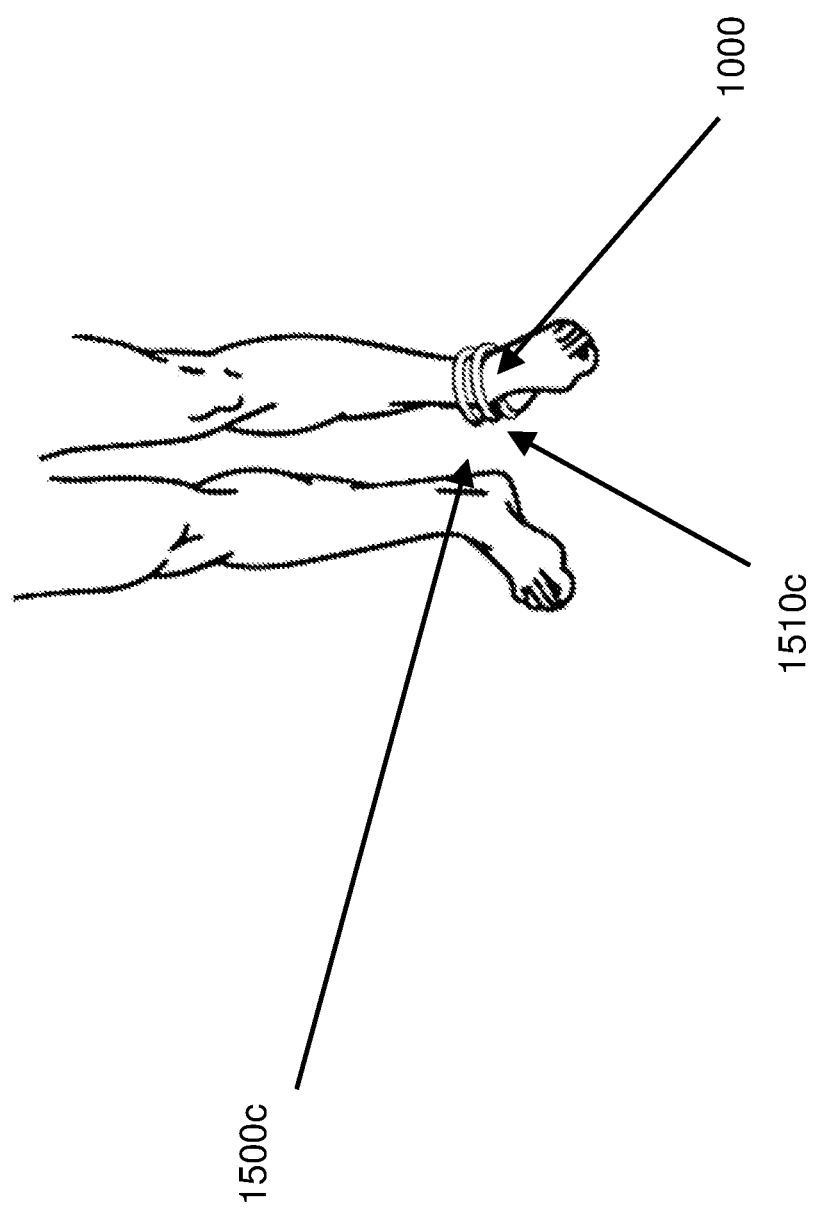

FIGS. 15A-15C illustrates exemplary aspects 1500a, 1500b, 1500c of the method described above with respect to FIG. 11. In some embodiments, the body 1060 may be wrapped around a user's hand, wrist, or arm 1510a, leg 1500b, or ankle 1510c. In some embodiments, multiple coils may be used around the member (also applicable to the other methods described herein), to ensure greater stability against the desired body region. The body 1000 may be applied with any number of electrodes aligned around any region surrounding the wrist. In some embodiments, a deformable system 1000 may be applied in a coil-like arrangement with one or more electrodes arranged along the vagus nerve. In some embodiments, a deformable system may be applied in a coil-like arrangement with one or more electrodes arranged along or other desired vascular and/or nervous entities.

Figure 16:
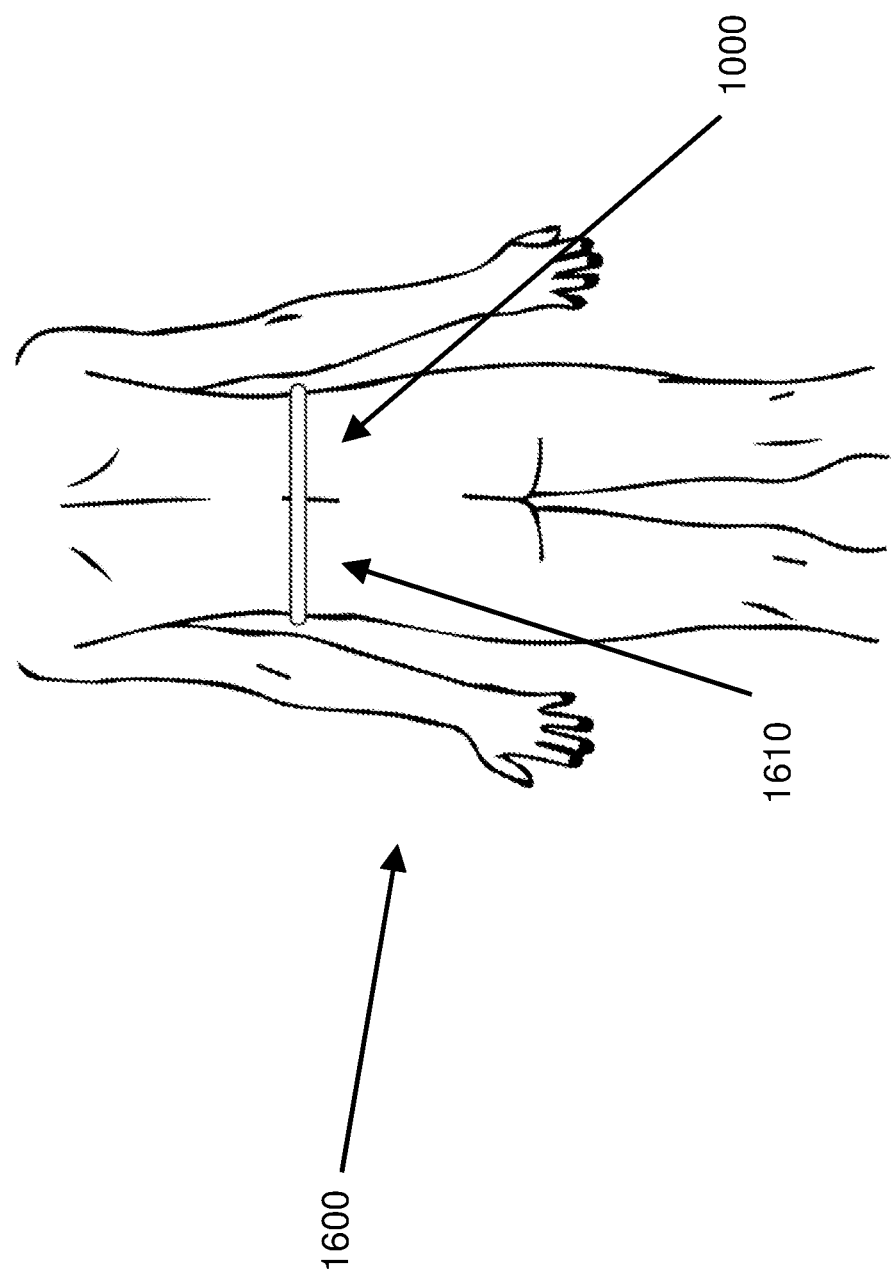

FIG. 16 illustrates an exemplary aspect 1600 of the method described above with respect to FIG. 11. In some embodiments, the deformable system 1000 may be applied to regions known to increase the likelihood of orgasm. For example, the system may be applied between the thoracic and sacral spinal regions, including the lumbar region 1610. An electrode may be applied within regions T8-L1. The system 1000 may be applied with the twist arrangement described above.

Figure 17:
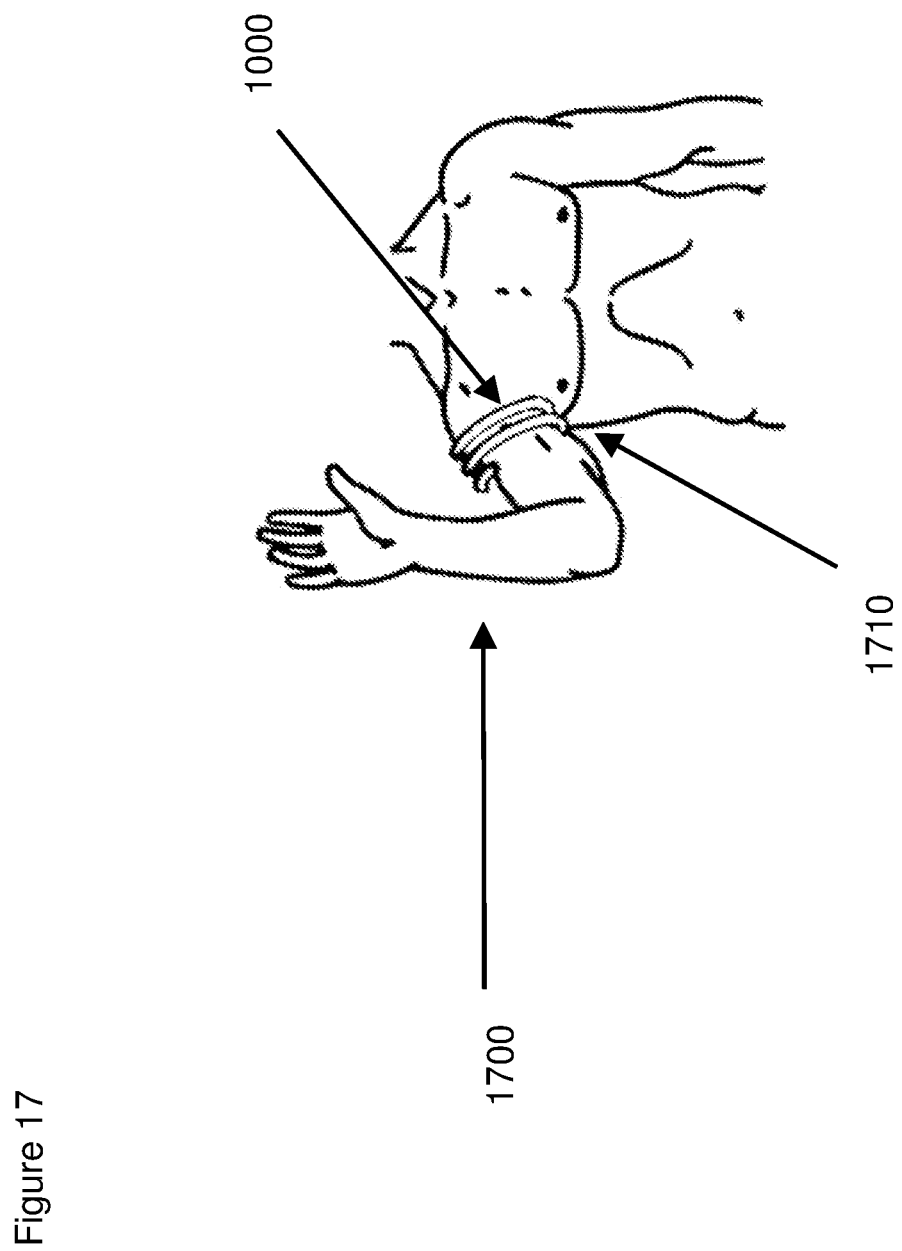

FIG. 17 illustrates an exemplary aspect 1700 of the method described above with respect to FIG. 11. In some embodiments, the deformable system 1000 may be applied around a bicep in a coil-like arrangement. One or more electrodes may be arranged closer to the shoulder 1710.

Figure 18A:
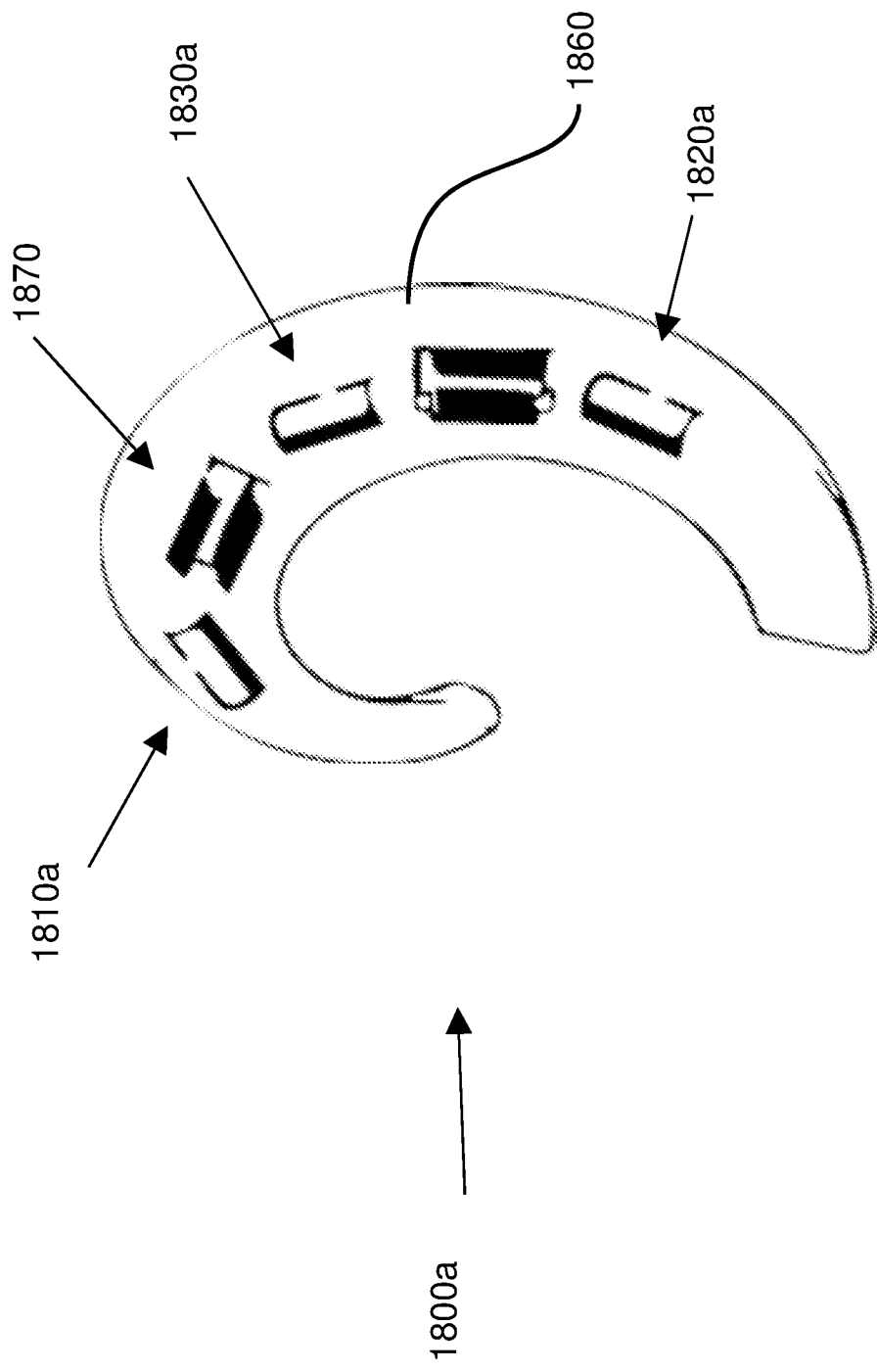
FIGS. 18A and 18B illustrate an exemplary system in which magnetic elements may be used to alter energy fields according to some embodiments.
Figure 18B:
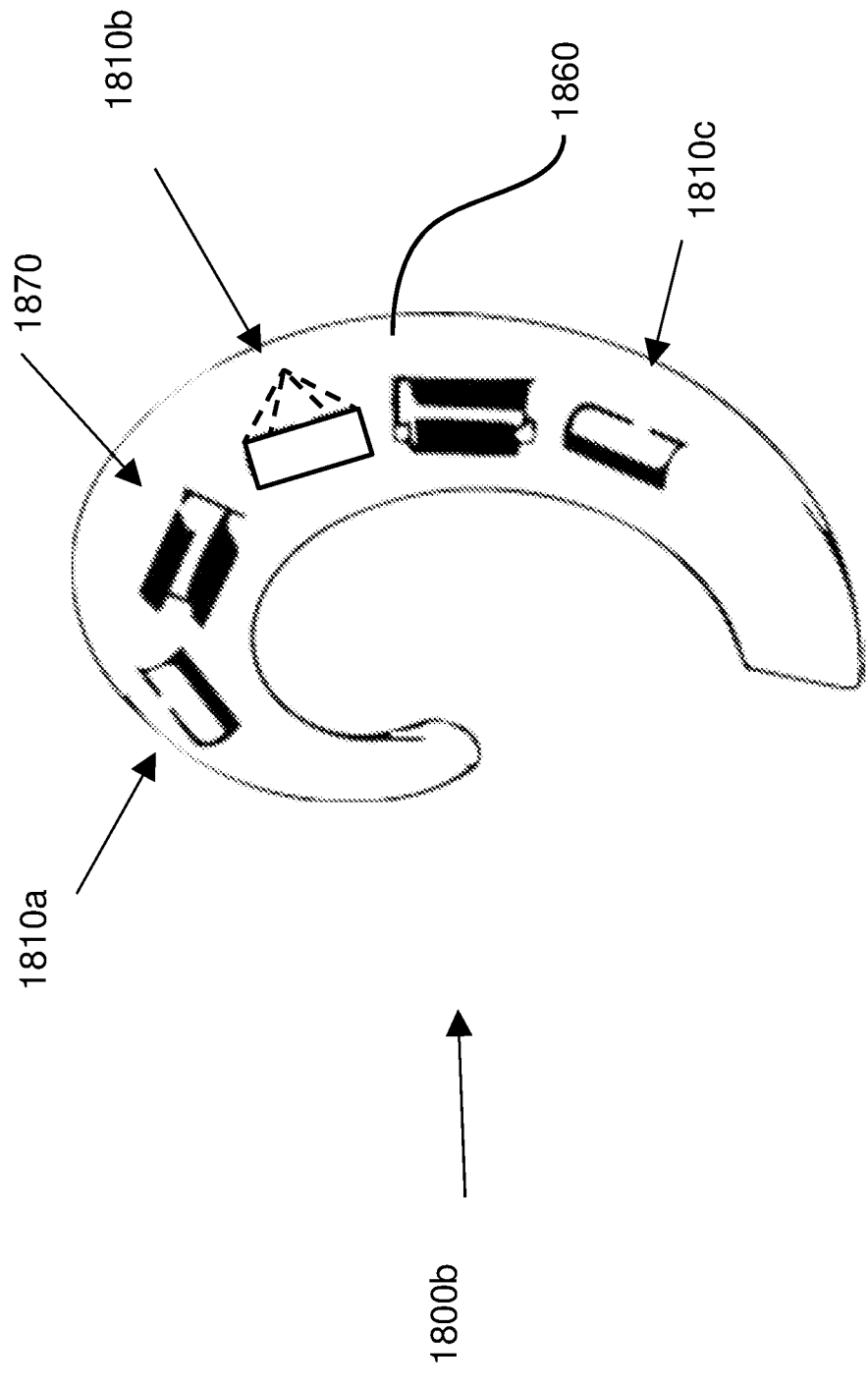

FIGS. 18A and 18B illustrate an exemplary system 1800 in which magnetic elements may be arranged according to various preferred embodiments. In the embodiment depicted in FIG. 18A, a body 1860 may include one or more electrodes 1870, which may optionally be embodied as filament groups. The electrodes 1870 may optionally be coupled to the body 1860 using a snap-fit anchoring arrangement as described above, and the anchors may optionally include magnetic elements. In some embodiments, magnetic elements 1810a-c (e.g., toroids, magnets, magnetic fluids, vibratory magnetic systems) may be positioned along the length of the body 1860. For example, the magnetic elements may be static magnetic structures. Each magnetic element may have a polarity, and the polarities of the magnetic elements may be arranged in particular arrangements beneficial to manipulating any biological tissue it is arranged upon. Although three magnetic elements 1810a, 1810b, 1810c are depicted, any suitable number of magnetic elements may be used. Further, the magnetic elements may be similar or dissimilar in shape. For example, as illustrated in FIG. 18A, each of the magnetic elements 1810a-c may be cylindrical. In another embodiment illustrated in FIG. 18B, magnetic elements 1810a and 1810c may be cylindrical, and magnetic element 1810b may be pyramidal. The choice of arrangements and shapes may be selected to alter the flux through the biological tissue in between.

Because the exemplary system 1800 may have a corresponding pair (e.g., one system may be applied around the left ear, while a second system may be applied over the right ear), these two systems may have their magnets arranged in a way that compounds their effect in shaping the distribution of applied and/or received energy. For example, on the left ear, magnetic elements 1810a, 1810b may have their north sides directed into the skin, while 1810c may have its south side directed toward the skin. On the right ear, magnetic elements 1810a, 1810b may have their south sides directed into the skin, while magnetic element 1810c may have its north side directed toward the skin. These polarities may also be reversed (i.e. each north in the previous description being made south, and each south in the previous description being made north). A different system may have all the north sides directed toward the skin over the left side with all the south sides directed toward the skin on the right side, or vice versa.

Figure 19:
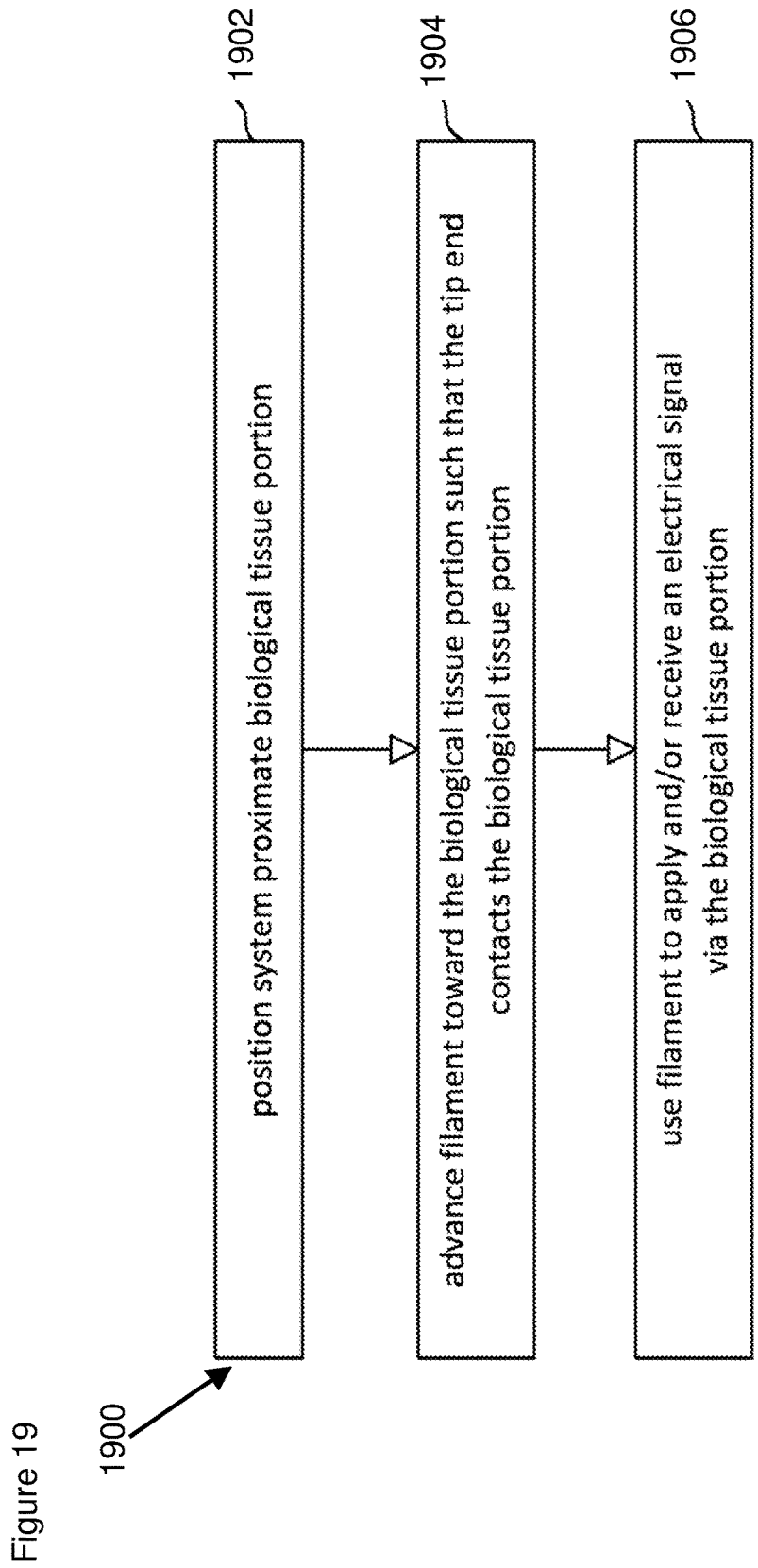
FIGS. 19-22 illustrate exemplary methods for applying and/or receiving signals according to some embodiments.

FIG. 19 illustrates an exemplary method 1900 for applying and or receiving an electrical signal via a biological tissue portion. In step 1902, a system (such as any of the systems described in any of the embodiments herein) may be placed proximate a biological tissue portion. Taking a headphone-type system as an example, the system may be placed around a user's head. In step 1904, a filament on the system may be advanced toward the biological tissue portion such that a tip end of the filament contacts the biological tissue portion. In the headphone-type system, for example, the arcuate members may be placed around a user's ears and situated such that the filaments contact the user's skin behind the user's ears. Where multiple filaments are provided, step 1904 may result in two or more filament tip ends being placed in contact with the biological tissue portion. In some embodiments, multiple filaments may extend in substantially the same direction such that the tip ends may be placed in contact with a flat surface without changing an orientation of the system body.

In step 1906, the filament may be used to apply and/or receive an electrical signal via the biological tissue portion. In some embodiments, for example, an electrical stimulus may be applied to the biological tissue portion via the filament. In some embodiments, electrical activity within the body may be received by the filament and relayed to a detector for performing measurements and analysis. In some embodiments, stimulus and measurements may be performed simultaneously or in alternation.

In some embodiments, the step of advancing the first filament toward the biological tissue portion may include disposing at least a portion of a tip end of the filament within a pore of the user's skin. In embodiments where multiple filaments are provided, a first filament may be at least partially disposed within a first pore and a second filament may be at least partially disposed within a second pore. Additionally, more than one filament may be at least partially disposed within a single pore. In some embodiments, the method 1900 may include an optional step of applying a force to the body such that the body plastically deforms to adapt to a shape of the biological tissue portion. For example, where the body is shaped as an arcuate member, a force could be applied to better adapt the shape of the arcuate member to the contours of the user's ear. In some examples, applying the force may include at least partially wrapping the body around a portion of the user's body. For example, the body could be wrapped around a user's ear, arm, hand, finger, leg, foot, toe, head, neck, lower back, pelvic floor, or penis. In some embodiments, applying the force may result in the body deforming from a first configuration that is substantially straight to a second configuration that is substantially bent.

In some embodiments, a first magnetic element may be placed proximate the biological tissue portion such that an energy field applied by the filament(s) is distributed in a different pattern than the energy field would have been distributed if the first magnetic element were not present. In some embodiments, a second system may be provided proximate a second biological tissue portion. In the headphone-type example, a first system may be placed on one ear, and a second system may be placed on the other ear. The systems may be but need not be mechanically or electrically coupled. In some embodiments, a first magnetic element of the first system may be placed proximate a first biological tissue portion, and a second magnetic element of the second system may be placed proximate a second biological tissue portion. In some embodiments, the north-south poles of the magnetic elements may be placed such that opposite poles are directed toward one another (e.g., the north pole of the first magnetic element is directed toward the south pole of the second magnetic element, or vice versa). Arranging the magnetic elements in this manner may generate a magnetic force which may assist in retaining the systems in the desired position on the user's body. In other embodiments, the like poles may be directed toward one-another.

Figure 20:
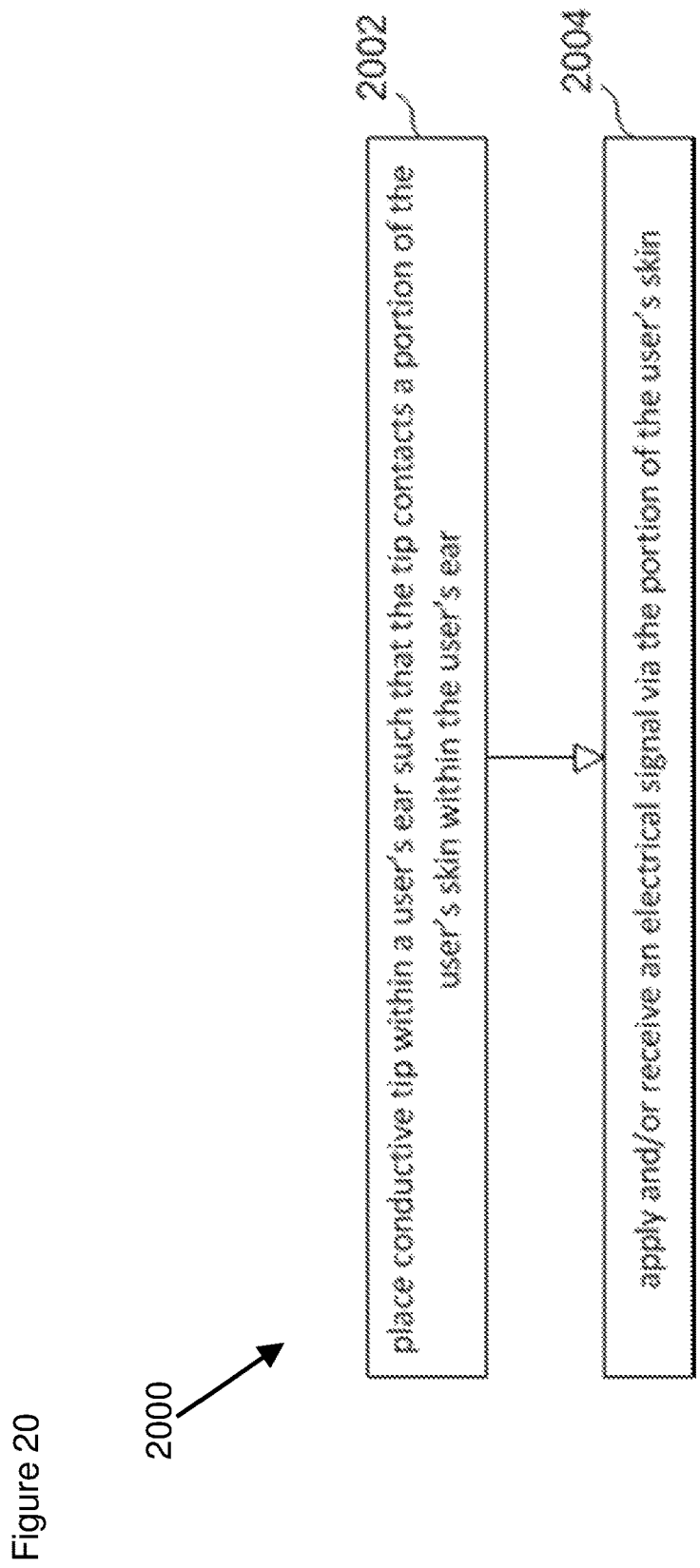

FIG. 20 illustrates an exemplary method 2000 for applying and/or receiving an electrical signal. Method 2000 may be performed using a system substantially as described with respect to FIGS. 8 and 9. In step 2002, a conductive tip may be placed within a user's ear such that the tip contacts a portion of the user's skin. In some embodiments, the tip may include a channel and may be coupled to a base. In some embodiments, the base may include a conductor in electrical contact with the tip such that an electrical signal may pass between the base and the tip. Placing the conductive tip within the user's ear may result in an outer surface of the conductive tip resiliently deforming to adapt to a shape of the user's ear in which the conductive tip is placed.

In step 2004, an electrical signal may be applied and/or received via the portion of the user's skin. In some embodiments, for example, a stimulus may be transmitted from a conductor, to the conductive tip, and then to the user's skin. In some embodiments, electrical activity within the user's body may be received at the conductive tip and transmitted through the conductor to a detector for measuring and analyzing the received signal. In some embodiments, a dedicated magnetic device may affect the impedance of biological tissues and the electromagnetic pathways through them by means of the magnetoelectric effect. In some embodiments, stimulus and measurement may be performed simultaneously or in alternation. In some embodiments, a speaker may be arranged in the base, and sound may be transmitted through a hollow interior of the channel to the user's ear at the same time that stimulus and/or measurement are performed.

In some embodiments, the base may have a projection and the conductive tip may have a channel as generally described above with respect to FIGS. 8 and 9. In some embodiments, the method 2000 may include advancing the channel over a portion of the projection to engage the conductive tip to the base. In some embodiments, the channel may be resiliently deformed as the channel is advanced over the projection, and/or an elastic force may bias the channel into engagement with the projection and/or an electrical contact on the projection. In some embodiments, the method 1200 may include replacing the conductive tip. For example, the method 2000 may include removing the conductive tip from the base. The method 2000 may further include placing a second conductive tip on the base.

Figure 21:
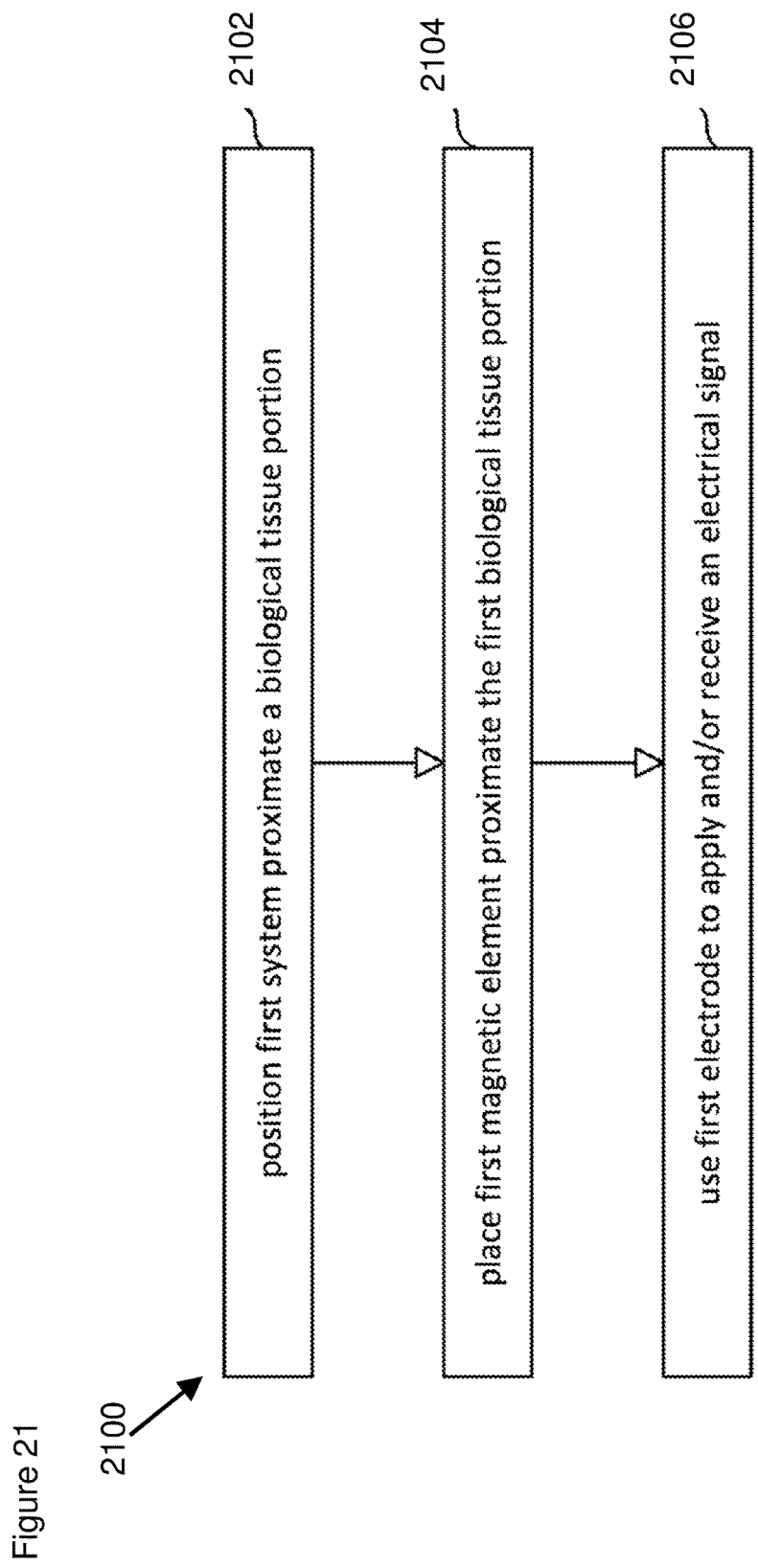

FIG. 21 illustrates an exemplary method 2100 for applying and/or receiving an electrical signal. Method 2100 may be used in combination with any of the system embodiments discussed herein. In step 2102, a first system may be placed proximate a biological tissue portion. In some embodiments, the first system may include one or more of a first body, a first conductor, a first electrode, and a first magnetic element. In some embodiments, the first magnetic element may be one or more of a magnet, a toroid, a conductive coil, a magnetic powder, and a magnetic fluid. In step 2104, the first magnetic element may be placed proximate the first biological tissue portion. Step 2104 can be but need not be a separate step from 2102. For example, where the magnetic element is rigidly affixed to a portion of the first system, placing the portion of the first system proximate the biological tissue portion may naturally result in the magnetic element being placed proximate the biological tissue portion. That steps 2102 and 2104 are illustrated as two steps therefore should not be interpreted to exclude embodiments where performing one of the steps naturally results in the other being performed—rather, the instant disclosure is intended to expressly include such embodiments.

In step 2106, the first electrode may be used to apply and/or receive an electrical signal via the biological tissue portion. In some embodiments, for example, a stimulus may be transmitted from a conductor, to the first electrode, and then to the biological tissue portion. In some embodiments, electrical activity within the user's body may be received at the first electrode and transmitted through the conductor to a detector for measuring and analyzing the received signal. In some embodiments, stimulus and measurement may be performed simultaneously or in alternation. In some embodiments, a first energy field applied and/or received by the first electrode may be distributed in a different pattern than the first energy field would have been distributed if the first magnetic element were not present.

In some embodiments, a second system may be placed a second biological tissue portion. In some embodiments, the second system may include one or more of a second body, a second conductor, a second electrode, and a second magnetic element. The second magnetic element may be one or more of a magnet, a toroid, a conductive coil, a magnetic powder, and a magnetic fluid. In some embodiments, the second magnetic element may be placed proximate the second biological tissue portion. In some embodiments, the second electrode may be used to apply and/or receive an electrical signal via the second biological tissue portion. In some embodiments, a second energy field applied and/or received by the second electrode may be distributed in a different pattern than the second energy field would have been distributed if the second magnetic element were not present. In some embodiments, the north-south poles of the magnetic elements may be placed such that opposite poles are directed toward one another (e.g., the north pole of the first magnetic element is directed toward the south pole of the second magnetic element, or vice versa). Arranging the magnetic elements in this manner may generate a magnetic force which may assist in retaining the systems in the desired position on the user's body. In other embodiments, the like poles may be directed toward one-another.

Figure 22:
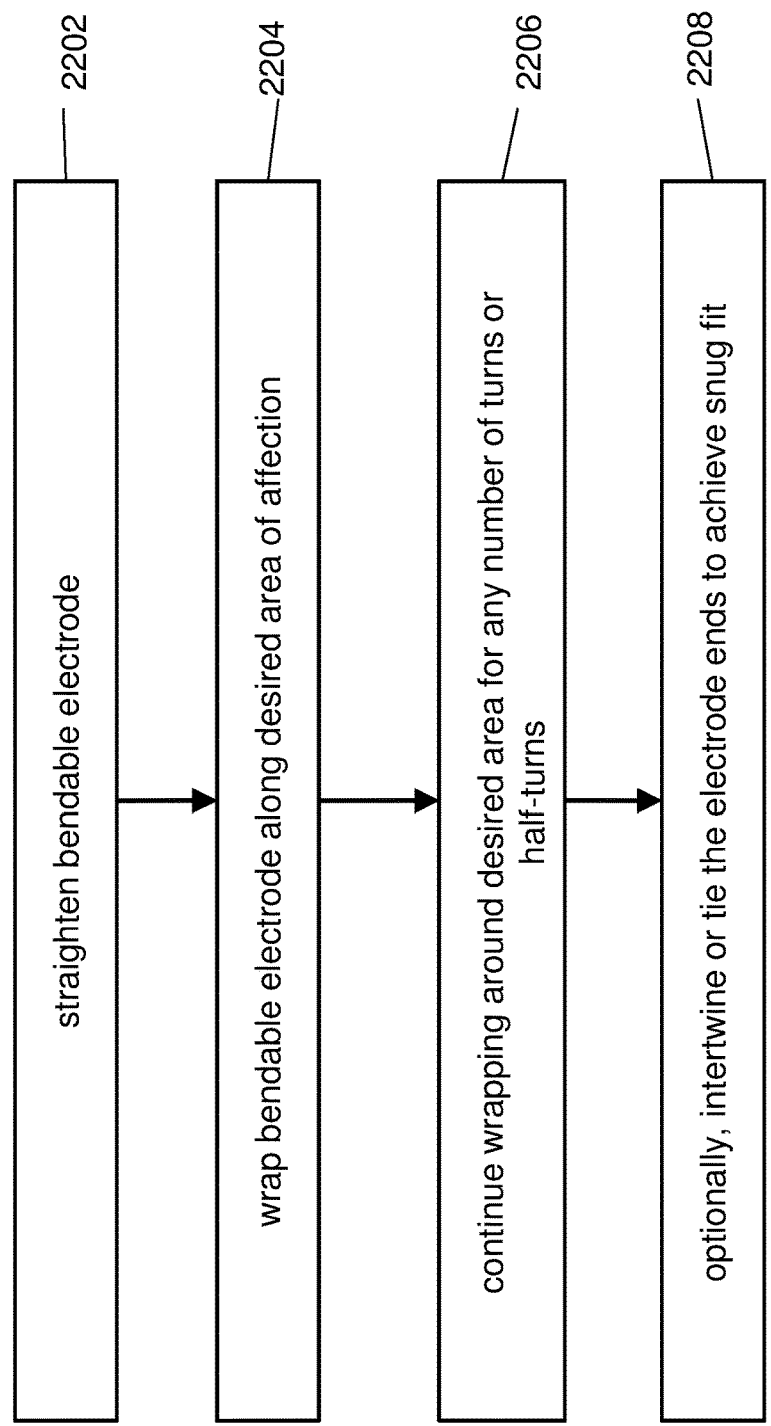

FIG. 22 illustrates an exemplary method 2200 for applying and/or receiving an electrical signal. Method 2200 may be used in combination with any of the system embodiments discussed herein. In step 2202, a system 1000 as described above with respect to FIG. 10 is first straightened to a standard position if it has been set beforehand. Then, in step 2204, the system 1000 is wrapped around the desired area where it may be applied. In step 2206, this wrapping may continue for n number of turns, where n may be fractional turns some value greater than 1. After the wire has been pressed adjacent to the skin, it may be tied to ensure greater stability in 2208.

One application for enhanced electrode performance comes in the form of a decentralized biometric internet. Since its inception the internet has been based around a one-CPU-one-user protocol, meaning a single person can program multiple machines to simulate multiple active users. Such a phenomenon is the reason elections are administered in-person, why Twitter followers, Amazon reviews, and Facebook likes are for sale, and why political and economic discussions on the internet are not to be trusted. If there was an area of the internet associated with a "live biometric," the phenomenon of fake or purchased accounts would be severely debilitated. To date, the usual inconvenience of wetting the skin has made electrodes unsuitable for an average consumer. Having improved electrodes allows us to add an additionally secure element of biometricity to cybersecurity, that has not yet been tapped by tech companies and the government.

Google's "I'm not a robot" task, also known as reCAPTCHA, is the current standard for liveness detection or human detection in modern cyber security. Liveness detection, which can also be interpreted as human detection, is a method for to test whether a person is a user is a live person or a bot. Unlike the reCAPTCHA system, signals over a biometric internet may exhibit an element of biometricity. Thus, these signals may human-detect or liveness-detect a person, and they may also identify that person. This enables stronger security through a combined identification and human detection protocol.

Biometrics that exhibit both identification and human detectable attributes are rare. Voice data, video recordings of facial expressions, and skin potentials have shown a high degree of biometricity as well as a liveness detectability. These are special biometrics because they also exhibit liveness. Unlike DNA, a fingerprint, or iris snapshots, which are effectively static files that can be stolen or faked, "live" or "human-detectable" biometrics can be modulated based on an input stimulus or "challenge". If such a stimulus originates from a decentralized network's recent parameters, a high degree of confidence may be placed in a determination that the recorded signal originated as recently as the network's parameters that were used to generate it. This implies that, if the signal were faked, the attacker would only have X amount of time to have generated the signal, where X is the time since the signal was generated.

For example, a recent random number generated from a block's hash within a blockchain may be translated into a waveform with a specific pattern of noise based on the block hash. As every block is associated with a publicly verifiable timestamp, the resulting waveform of a block that occurred n blocks ago is a time-dependent signal. It is associated with an event that occurred X time ago. This waveform may then be injected over a person's skin, and recorded somewhere else on the body, using suitable electrodes. The recorded signal is then both a function of the original random number and the skin make-up of a person; or, a person's biometricity. As another example, same random number may be used to generate a video telling a person to blink or make a facial expression at a specific time point. If their eye-blinks or facial expression corresponds with the indicators given by the random number, then they were generated as recently as the random number was generated. Finally, a similar audio or audiovisual signal can be used to tell a person to speak a specific string of random words based on said random number. Assuming that the random number is large enough that constructing these signals in advance is unattainable, and that simulating the biometricity of these signals is too difficult for a motivated attacker, the security of a one-person-one-vote internet can be preserved.

Aside from live biometrics, other blockchain protocols such as uPort have attempted to solve the one-CPU-one-vote issue using purely digital and/or static biometric means. Both of these techniques are more easily faked than a liveness-detectable biometric internet. In the solely digital network, the network is duped by creating fake accounts across the given websites used to verify a particular person. In the static biometric system, a fingerprint submitted by a user can be duplicated or faked by a privileged party. The threat in these situations are not that the average user will perform these attacks against the network. Instead, it is that someone with a large amount of pre-existing power or wealth in a given decentralized network (or, in Google's case, a centralized network) will find this to be a more cheaper method of abusing or monetizing the network than more traditional means of attack or profiting.

Creating a one-person-one-vote network would increase the level of trust held by each node who is involved in the network. By increasing trust, less verification is needed across the decentralized network, resulting in more efficient computations. As such, although many decentralized networks such as blockchains may have trouble scaling computations within decentralized programs such as smart contracts, a one-person-one-vote internet would result in cheaper and more efficient computations for scaling to a global blockchain.

Figure 23:
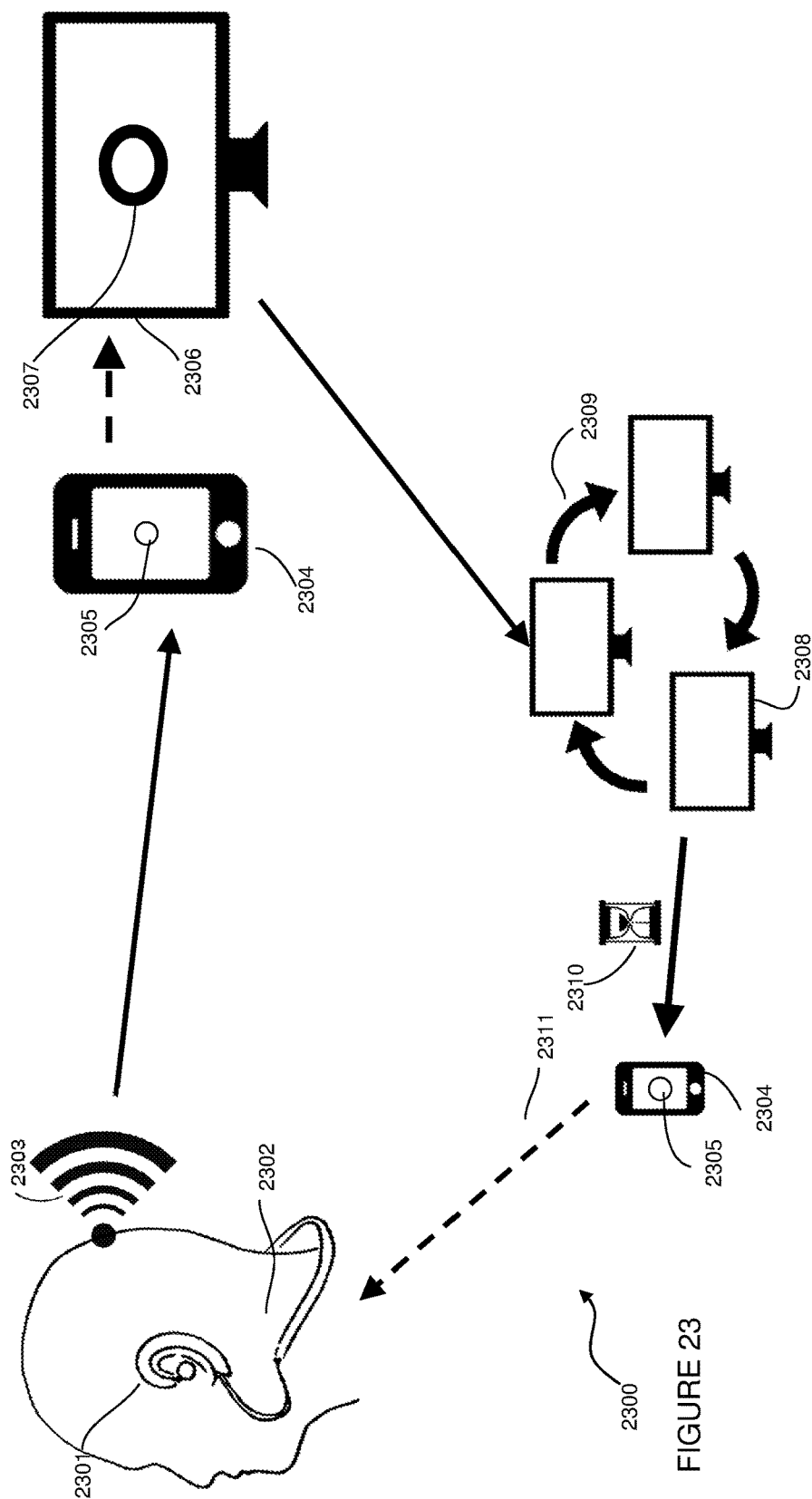
FIG. 23 illustrates an exemplary system for sharing biological information into and from a decentralized network.

FIG. 23 illustrates an exemplary embodiment of a system 2300 for sharing biological information into a network and receiving a response based on that data. In some embodiments, a user 2302 may employ a user device 2301 (which in some embodiments may be a headphone device or any of the other electrode devices described above) to record biological data. The biological data may be, for example, brainwave data, voice data, facial expression data, or any other suitable biological metric. The biological data may be transmitted wirelessly 2303 to a wireless device 2304, which may be, for example, a phone, computer, tablet, or any other suitable computing device. The user device 2301 may communicate with the wireless device 2304 via a short-range communication protocol, such as Bluetooth, RFID, or NFC. The wireless device 2304 may optionally be configured to run blockchain-compatible application software 2305 which may be stored in memory accessible by a processor of the wireless device 2304. In some embodiments, the user device 2301 may also include a processor and memory. In some embodiments, the user device 2301 and wireless device 2304 may together define a local user system within the possession of the user. Other devices, such as cameras, microphones, position detectors, virtual reality devices, etc. may also be included within the local user system.

The wireless device 2304 may transmit the biological data to a node 2306. The wireless device may communicate with the node 2306 via longer range radiofrequency transmissions and/or wired communication channels. The node 2306 may be a server, dedicated computer, or any other suitable computing device. The node 2306 may include a processor and a memory which may store network software 2307 which, when executed by the processor, allows the node to perform data processing and network functions as described below. In some embodiments, the node 2306 may be a server in a centralized network that collects and analyzes data from a plurality of user devices 2301. The analysis may be used for authentication, liveness detection, and/or identification as described herein.

In some embodiments, the node 2306 may transmit the biological data or a parameter derived therefrom to one or more nodes 2309 within a decentralized network, after which a decision may be made based on the biological data. After a certain length of time 2310, a communicator node 2308 may then transmit a decision message based on the data back to the original user's wireless device 2304. In some embodiments, the communicator node 2308 may be the node to which the user's biological data was initially uploaded. In some cases, the node to which the biological data was initially uploaded may have been selected due to proximity, available bandwidth, or present connection to the user's wireless device 2304. In such cases, it may be advantageous to relay the decision message back to the wireless device using the same node.

In response to receiving the decision message, the wireless device 2304 may present a visual, auditory, audiovisual or some sort of stimulatory signal 2311 to the user based on the input data. In some embodiments, the decision message may include an indication that the user's identity has or has not been verified. In some embodiments, successful verification may allow the user to access privileges associated with their account, such as conducting transactions using currency associated with the account, updating account settings, and/or performing privileged actions such as voting or transmitting and/or receiving restricted communications. In some embodiments, successful verification may allow a user to update the security settings to include a digital key associated with a new device. For example, after an initial successful log-in using biological data, a digital key associated with the wireless device used for the successful log-in may be associated with the user's account so that subsequent log-in attempts from that device do not require submission and verification of biological data. In the event that the user later wishes to log into their account from a new device, biological data could again be used to verify that the user of the new device is indeed the account owner. In this manner, the risk of losing access to an account, such as by misplacing a mobile device, may be substantially reduced. In some embodiments, certain types of account transactions may require two-factor authentication. For example, after a first successful identification transaction is complete, a user could be required to enter a passcode or submit additional specialized biological data, such as brainwaves collected while the user is thinking a predetermined passcode thought.

In some embodiments, a user may receive a reward for submitting biological data. For example, an entity may elect to pay users (using standard currency or cryptocurrency) for submitting data while receiving certain stimuli (such as an advertisement or political message). In some embodiments, the entity may upload the desired stimuli and a specified incentive structure to a network. The network may in turn transmit the desired stimulus information to the user, optionally along with an indication associated with a recent block hash. The user may then receive the stimulus and upload their biological data for verification on the network. Upon successful verification of the biological data, the user may receive a notification that the reward has been credited to their account. The verified biological data may be transmitted to the entity paying the incentive along with a notification that the incentive has been paid. Optionally, anonymity of the user and/or the entity may be preserved throughout this process.

Figure 24:
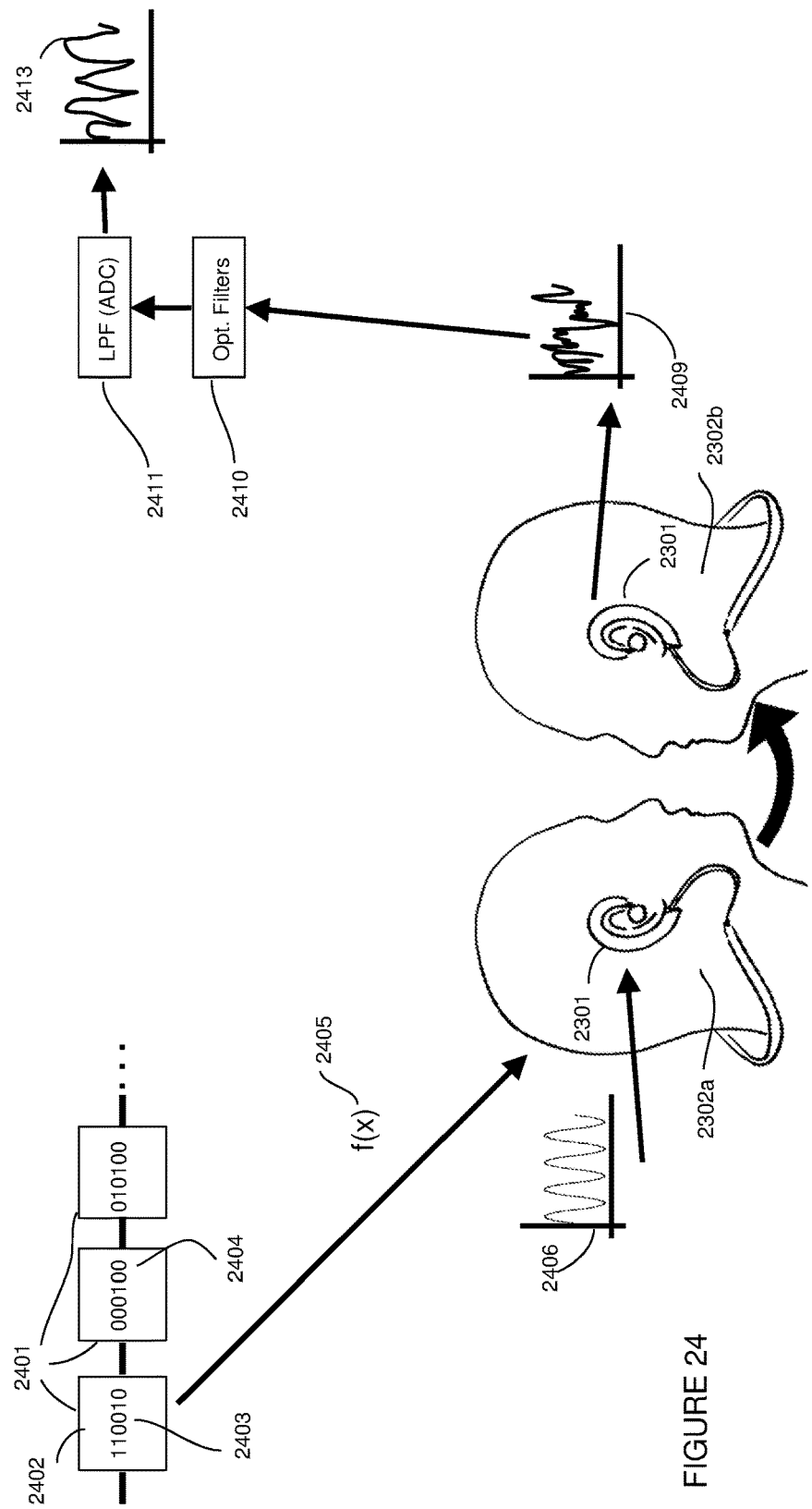
FIG. 24 illustrates an exemplary system for obtaining a biometric and human-detectable signal.

FIG. 24 illustrates an exemplary system 2400 for obtaining a biometric signal. As discussed below, exemplary biometric signals may include auditory, video, facial, and/or voice data, and/or stimulation/vibratory, and/or recording signals that may pass through an electrode in proximity to the skin. In some embodiments, a plurality of data blocks 2401 may each contain a mostly-random identifier known as a block-hash 2404. The block-hash may be a random number within a very large space, such as a random value from 1 to 2^256. Once a large number of blocks have been added to the end of the chain, the data stored in a block that occurred n blocks ago can be trusted with a high degree of confidence. A highly-trusted block which occurred n blocks ago 2402 may have a mostly-unique identifier or block-hash 2403, which can be input into a function 2405. The function 2405 may translate this random number into a brief stimulatory or "challenge" signal 2406. In some embodiments, the function 2405 may generate a single output for any given input within a range of possible input values. Further, the function 2405 may be consistent across all nodes and users, so that each node and user can obtain the same input signal 2406 for later verification of submitted data. In some embodiments where an audio signal is used, the function 2405 may specify parameters such as pitch, rhythm, duration, and instrumentation for the selected signal 2406, and one or more of these parameters may vary based on the values contained in the block has 2403. Similar parameters may be identified and varied for visual signals (e.g., pattern, brightness, position), electrical signals (e.g., waveform, frequency, amplitude), and other types of inputs.

The signal 2406 may then be applied to a user's head or other portion of the user's body. In some embodiments, the signal 2406 may be an auditory signal which may be transmitted through a speaker located near the ear canal. In some embodiments, the signal 2406 may be a video signal, which may be shown to a user on a display of the wireless device 2304 or the user device 2301. In some embodiments, an audio, visual, and/or audiovisual stimulus may be provided in a virtual reality environment via a virtual reality headset. In some embodiments, the signal 2406 may be an electric, magnetoelectric, and/or vibration stimulatory signal, which may sent through an electrode and/or vibration motor located near the head. On the other side of the head, the signal may be received as a modified signal 2409, which may include an indication of both the original signal 2406 and a biological characteristic of the user. Different mechanisms may be used where voice or facial data is instead recorded. For example, voice data may be recorded using a microphone, which may be located on the wireless device 2304 or user device 2301. Facial image data may be recorded through a camera, which may be located on the wireless device or user device 2301.

The modified signal 2409 may optionally be passed through a filtering circuit 2410, 2411. In some embodiments, the filtering circuit 2410, 2411 may include a low-pass filter 2410 and analog-to-digital converter 2411. Other circuit elements may also be used. The filtering circuit may be designed such that the modified signal 2409 is processed to comply with standardization requirements of an application for which the resulting signal will be used, thereby resulting in the generation of a standardized signal 2413. Such a signal is identifiable because it has been generated from movement across a user's skin. It is human or "liveness" detectable because it is also generated as a function of the most recent block hash.

Figure 25:
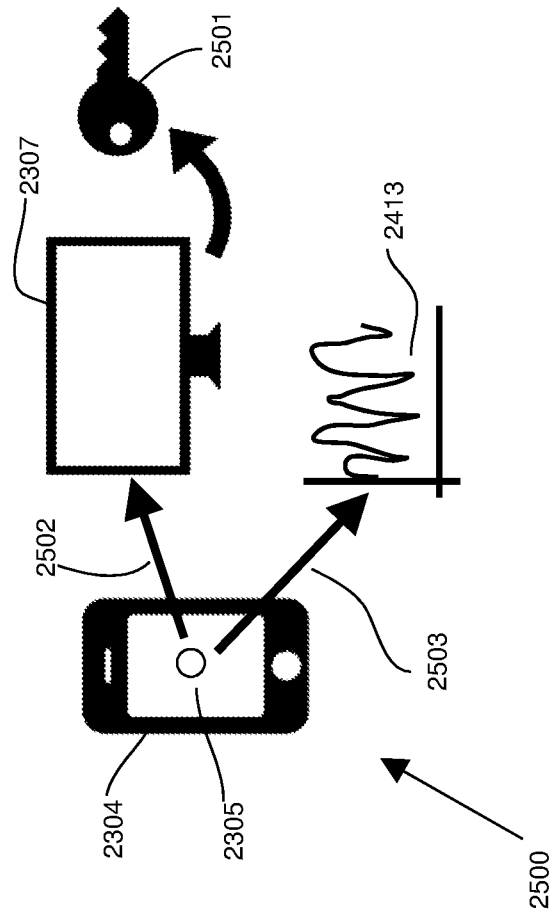
FIG. 25 illustrates an exemplary system for anonymizing biological data prior to communication over the network.

FIG. 25 illustrates an exemplary system 2500 for optionally anonymizing biological data prior to communication over the network. In some embodiments, a biological data signal 2413 may be anonymized using an encryption key 2501. In some embodiments, the key 2501 may be a homomorphic encryption key. In some embodiments, the key 2501 may be stored on or accessed by a user's wireless device, and the encryption technique may be used before transmitting the data signal from the wireless device to a network node. In some embodiments, the encryption key may be stored on or accessed by a first network node (which may optionally be a privileged node 2307), and the encryption technique may be used before the data is transmitted to one or more other nodes within the network. By using homomorphic encryption, data may be anonymized in a format that permits mathematical and/or analytical computations while retaining anonymity and encryption.

Figure 26B:
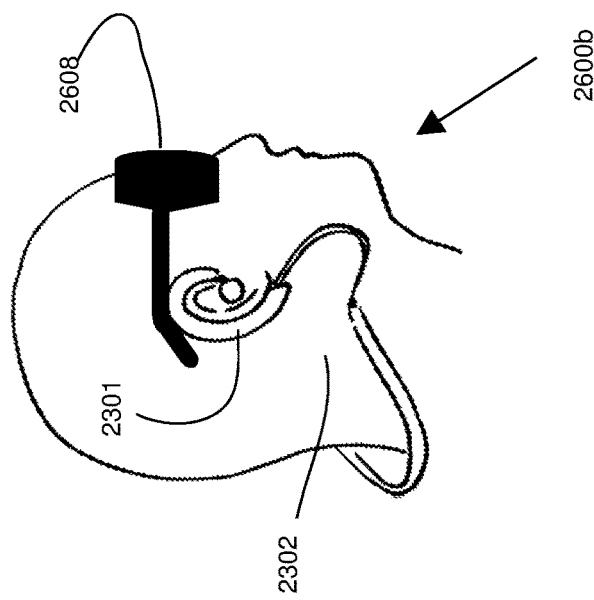
FIGS. 26A and 26B depict exemplary mechanisms for providing visual and/or auditory stimuli to a user which may modulate the type of biological data sent across the network, to the tune required by recent network parameters.
Figure 26A:
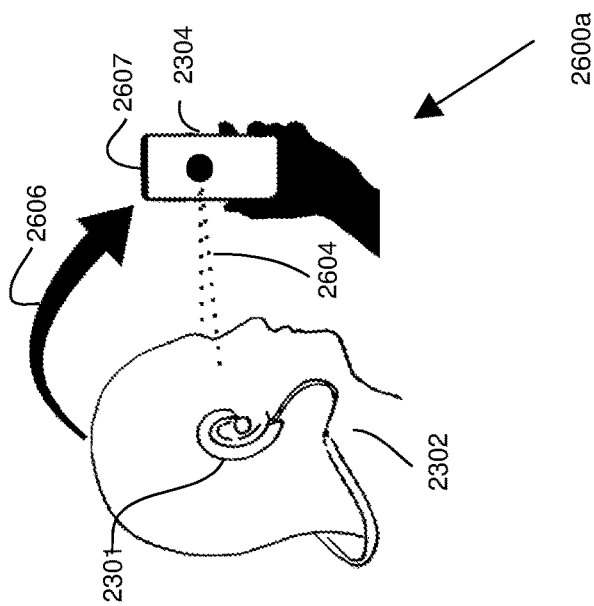

FIGS. 26A and 26B depict exemplary systems 2600a, 2600b for providing visual and/or auditory stimuli to a user. In an exemplary system 2600a, a user 2301 may wear a stimulation/recording device 2302 and may view a visual stimulus presented in the wireless device 2304. In some embodiments, a camera 2607 may be positioned on the wireless device 2304. In some embodiments, facial data such as eye-tracking data 2604 and/or facial expression data 2606 may be used to make sure the user is paying attention to the screen and/or is a live person. In some embodiments, the obtained data may be transmitted from the wireless device to a node as discussed above. FIG. 26B depicts a related embodiment in which a user receives visual and/or auditory stimuli or other stimuli through a headset 2608. Here, the obtained data may be transmitted from the headset 2608 to a wireless device, or in other embodiments, the headset 2608 may itself function as a wireless device. In some embodiments, the headset 2608 may process and transmit obtained data to a node. In other embodiments, the obtained data may be relayed to a wireless device, which may in turn relay the data to a node, optionally after processing and/or standardizing the data.

Figure 27:
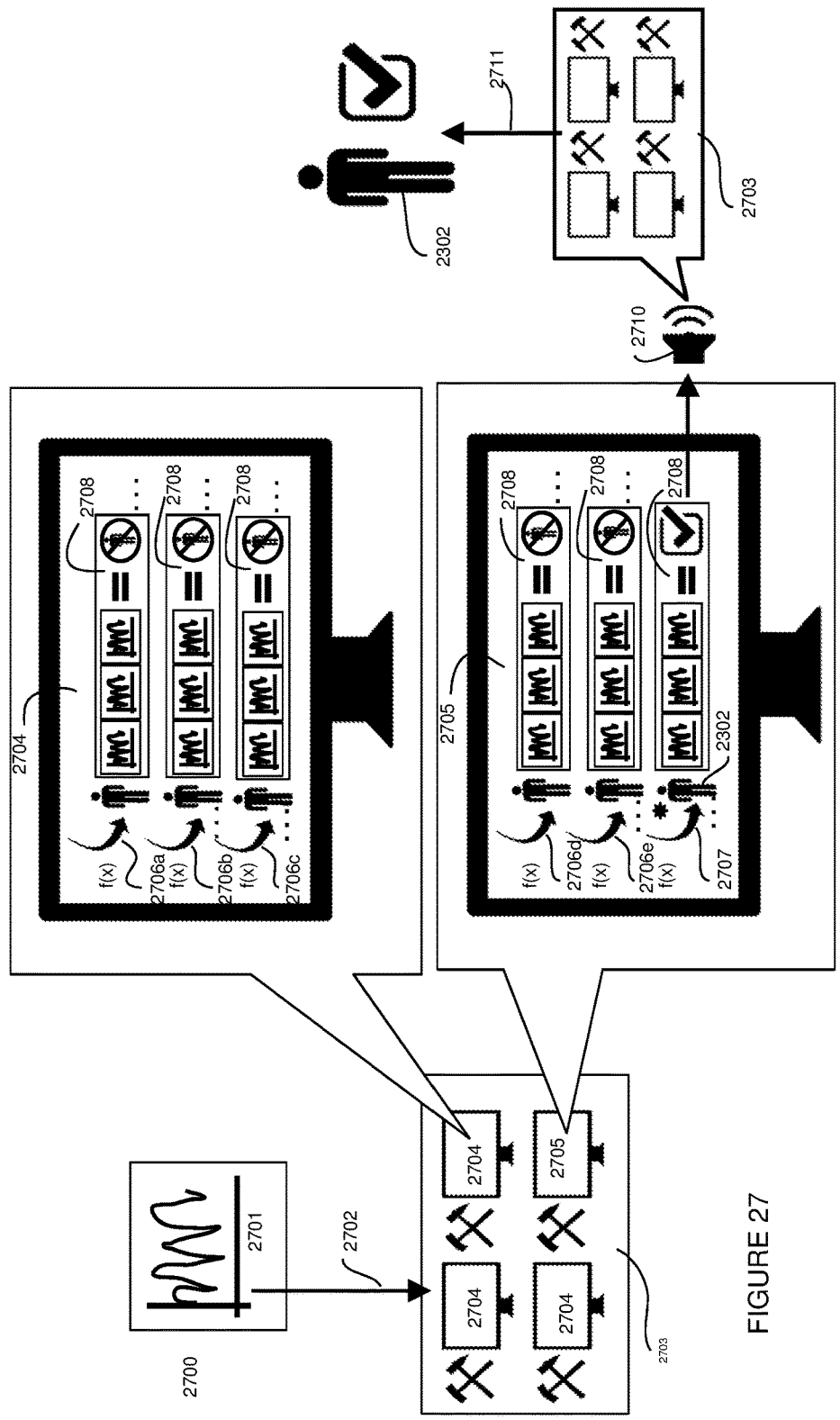
FIG. 27 illustrates an exemplary process for analyzing biological data over a blockchain.

FIG. 27 illustrates an exemplary process 2700 for analyzing biological data in a decentralized network. This exemplary process 2700 can be used for purposes such as identifying a person 2302 from whom the biological data was received. In some embodiments, data 2701 (which may be, for example, a biometric data signal such as those discussed above) may be transmitted among a plurality of nodes 2704, 2705 in a decentralized network 2703. In some embodiments, multiple nodes within the plurality may perform an analysis task simultaneously. In some embodiments, this task may include generating an identity estimate for the individual 2302 from whom the data 2701 was received. In some embodiments, an incentive may be awarded to the first node to successfully complete the analysis task, thereby creating a "race" among the nodes participating in the analysis task. In the illustrated embodiment, an "initiator" node 2705 successfully completes the task first, whereas other nodes 2704 are, for purposes of this task, considered "losing" nodes.

To generate an identity estimate, each participating node may select a candidate user 2706a-2706e from an account database accessible by that respective node. This account database may include data for a large number of users, and following each successful identification process, the account data for that user may be updated to include the newly validated biological data 2701 for that user. The candidate user 2706a may be selected by the node randomly or according to a function defined by the network or within the respective node. In some embodiments, each node may define its own method for performing identity determinations. For example, some nodes may select candidate users 2706a non-randomly based on recognized patterns for certain users or groups of users. By allowing nodes to define their own identification methods, nodes are incentivized to develop progressively more powerful algorithms, with a resulting improvement over time to the speed and accuracy of the network.

In some embodiments, after selecting the candidate user 2706a, the node may perform a comparison between the biological data 2701 and a set of historical data 2708 associated with the candidate user. In some embodiments, this comparison may be performed using a machine learning algorithm, optionally using a neural network architecture. For example, a recurrent neural network such as that described in "The Unreasonable Effectiveness of Recurrent Neural Networks" by Anrej Karapthy, which is incorporated by reference herein in its entirety, may be used as a framework for performing the types of comparisons described herein. In an exemplary machine learning embodiment, a node may compare the biological data 2701 against historical data 2708 for a candidate user and output a value between 0 and 1, with 0 representing perfect confidence that the two sets of data are not obtained from the same individual, and 1 representing perfect confidence that the two sets of data are obtained from the same individual. By training the machine learning algorithm on a large dataset with validated identifications, it is possible to obtain a high rate of prediction accuracy.

If a match is not found, the node may select a new candidate user 2706b, and repeat the above-described process using the same input biological data 2701. This process may continue within one or more nodes simultaneously until the initiator node 2705 determines a match between the candidate user historical data 2708 and the biological data 2701. The initiator node 2705 may then transmit a message 2710 including an identifier for the matching candidate user to one or more the other nodes. The losing nodes 2704 may then retrieve the historical data 2708 for the matching candidate, and compare this historical data against the input biological data 2701. If the losing nodes 2704 also verify that the data belongs to the candidate user 2706a, then candidate user 2706a is confirmed as being the person 2302 from whom the biological data 2701 was received.

Optionally, the winning node 2705 may receive a reward, such as units of a cryptocurrency, for first correctly determining the identity of the person 2302. Offering a reward for such an analysis task may incentivize a large number of nodes to participate in the task. In this manner, a large amount of computing power may be cost-effectively allocated to the incentivized task. In the identification example discussed above, this may allow a large amount of biological data to be accumulated and processed relatively quickly and inexpensively. This in turn may allow more accurate identity determinations based on larger and, in some cases, continuously updated databases.

Figure 28:
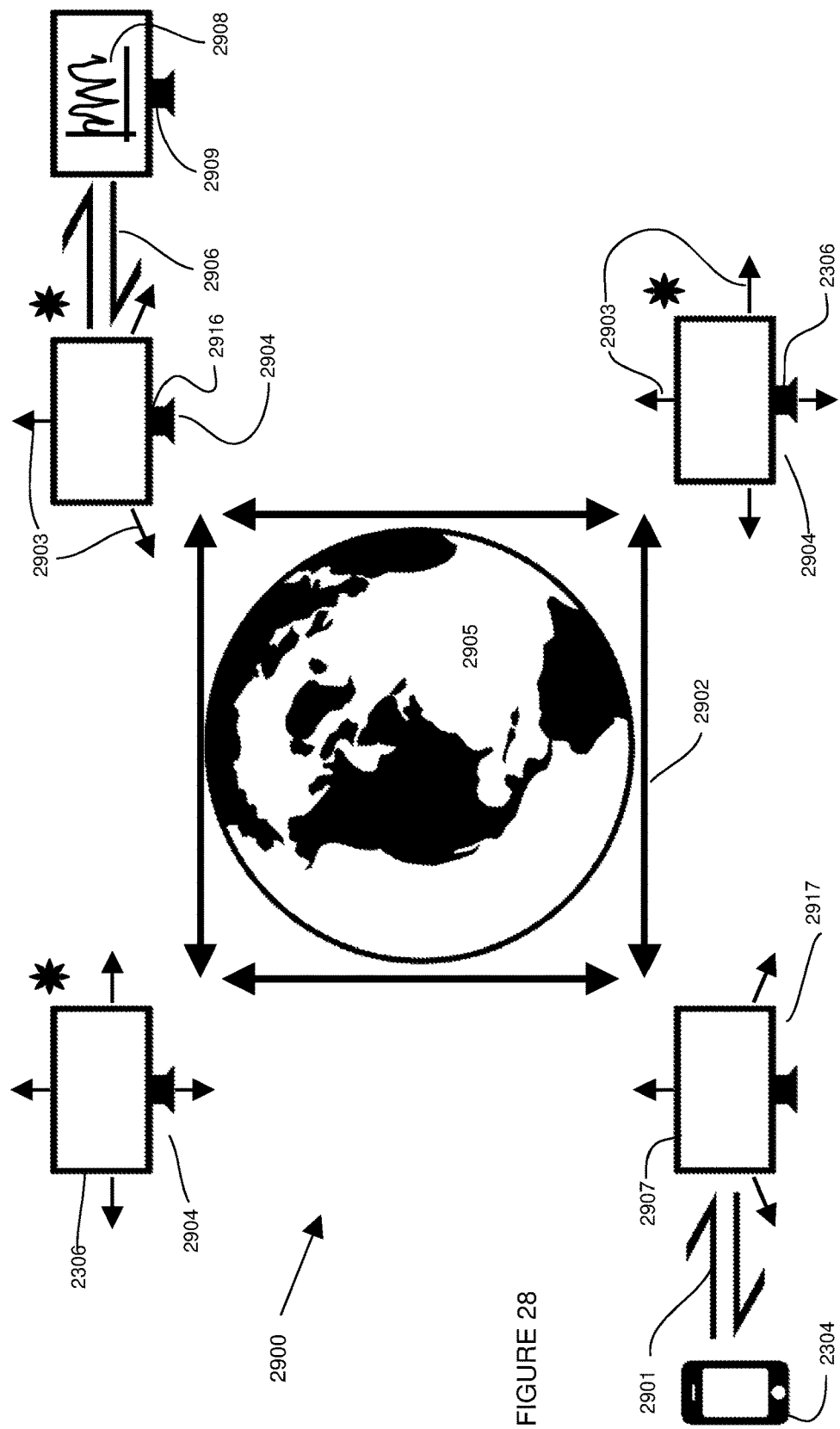
FIG. 28 illustrates an exemplary method for achieving consensus regarding a sample of biological data.

FIG. 28 illustrates an exemplary embodiment of a method 2900 for a computer network wherein consensus over a biological data's properties is achieved by a voting process among a plurality of nodes 2306. In some embodiments, nodes may be assigned vote weightings 2904, 2907. For example, a first node may have a relatively high weighting 2904 while a second node may have a lower weighting 2907. By allocating greater weight to more trustworthy nodes and/or nodes with greater processing power, it may be possible to improve both accuracy and processing speed of the network.

FIG. 28 also illustrates a test method 2906 for keeping the network honest by means of submitting past data for verification across said network. In some embodiments, an originating node 2917 may transmit to nodes within the network previously verified data 2908, which may be stored on a database 2909. The previously verified data 2908 may be "faked" as new data, meaning that the data may be transmitted in such a way that a test node 2916 will treat the data 2908 as though it were new data. The test node 2916 may then analyze the data according to its usual process, and circulate its result to the other nodes 2903 on the system. When the result is received by the originating node 2917, the originating node may compare the result received from the test node 2916 to the previously verified result to determine whether the test node 2916 is trustworthy. If the result is the same as what had been previously verified, a reputation score, which may be stored on a local hard drive of the originating node 2917 or may be shared across a plurality of nodes within the network, may be increased. If the result differs from what had been previously verified, the reputation score may be decreased. In some embodiments, lower-weighted voting nodes may use test method 2906 to evaluate whether higher-weighted voting nodes may be trusted. In some embodiments, a node's vote weighting may be based in part or in whole on that node's reputation score.

Figure 29:
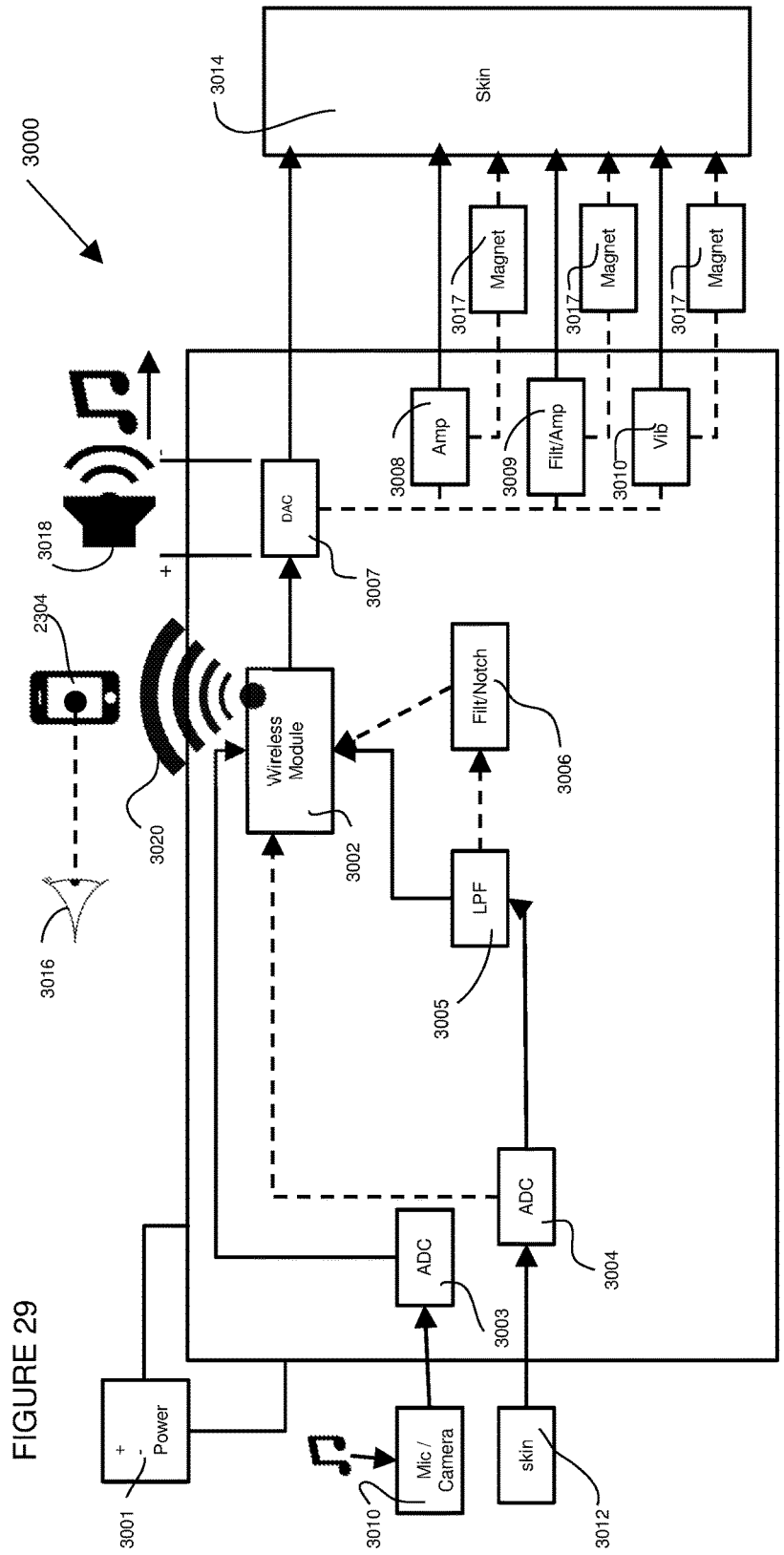
FIG. 29 illustrates an exemplary circuit for applying a stimulus and/or obtaining biological data.

FIG. 29 illustrates an exemplary embodiment of a device circuit 3000. In some embodiments, the circuit may be used for receiving data derived from a blockchain, modulating that data based on a being's biological properties and current network states, and/or returning the modulated signal back to the network as evidence of liveness or humanness. In some embodiments, a power source 3001 may provide power to the circuit. A wireless module 3002 may contain elements including an analog-to-digital converter, a digital-to-analog converter, a filter, and/or an amplifier. An analog-to-digital converter 3003 may receive audio, visual, or audiovisual data from a microphone and/or camera 3010 and output the resulting digital data to a wireless module 3002. Similarly, skin data 3012 (e.g., electrical data received from an electrode in contact with the skin) may also pass through an analog-to-digital converter 3004 and may optionally output the resulting data to filtering components such as a low-pass filter 3005 and/or a notch filter 3006. The wireless module 3002 may transmit and receive data to a wireless device 2304 via a wireless communication technology 3020 such as Bluetooth. The wireless module may also send data (such as data received from the wireless device 2304) through a digital-to-analog converter 3007, which may in turn feed data to a speaker 3018. Optionally, the data may be amplified by an amplifier 3008, filtered then amplified by a filtering and amplifying circuit 3009, or sent to a vibratory element 3010 (e.g., a vibration motor). A stimulus derived from the data received from the wireless device 2304 may then be applied to the user, such as to the user's skin 3014 or other suitable portion of the user's body (e.g., to the user's ears where an audio stimulus is applied). The applied signals may also contain elements of magnetoelectricity through use of a magnetic element 3017. The circuit or a wireless device may also collect facial data such as eye-tracking or facial expression data 3016. This data may be captured using a camera connected to the circuit or using a camera on the wireless device 2304.

Figure 30:
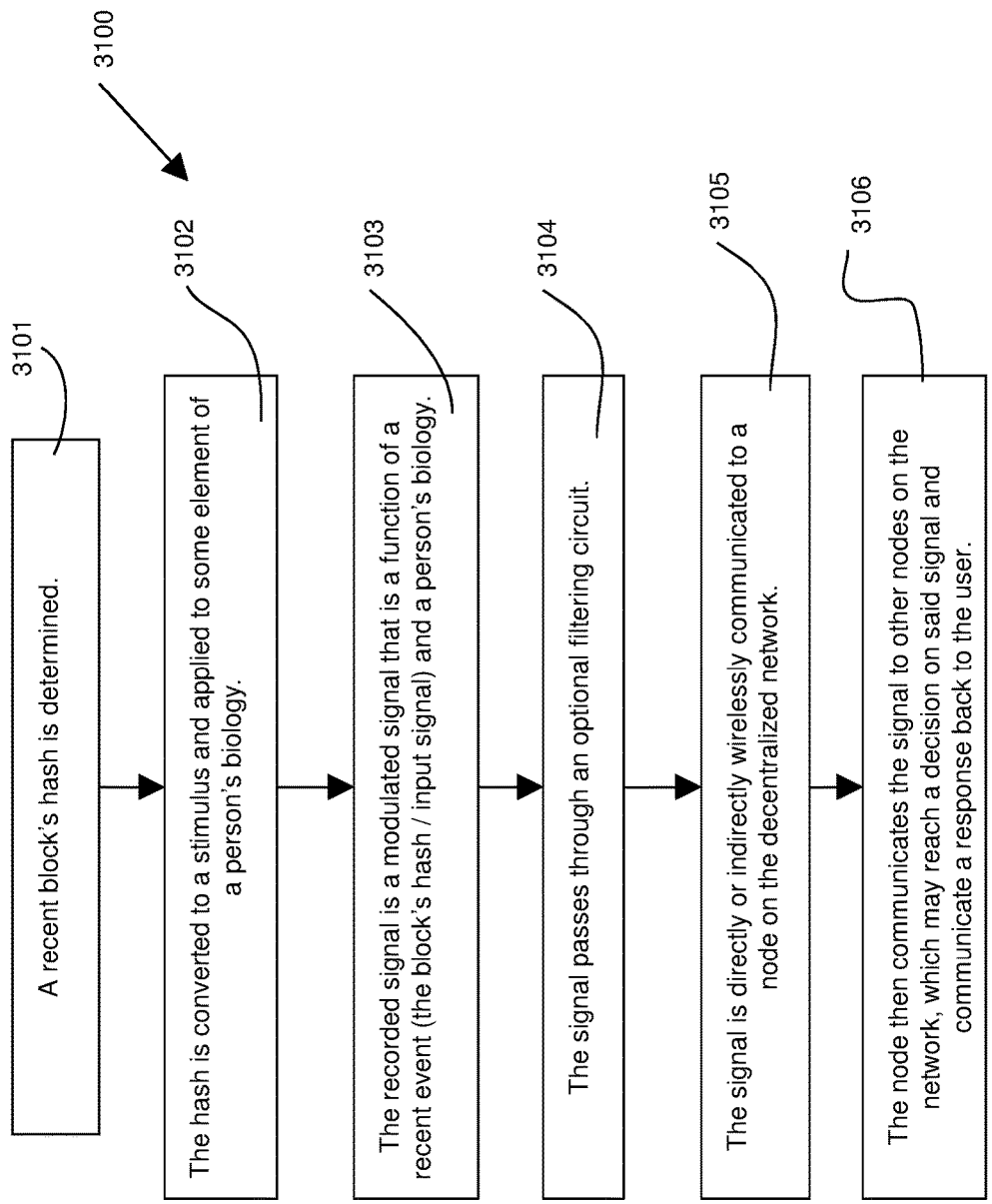
FIG. 30 illustrates an exemplary method for sending information from a blockchain to a user and back to the blockchain as a mechanism for decentralized liveness or human detection.

FIG. 30 illustrates an exemplary method 3100 for sending information from a blockchain to a user and back to the blockchain. As explained above, such a method may be used for decentralized liveness or human detection. In step 3101, a recent block's hash may be determined. The block's hash may be an effectively random number from a very large potential space. In some embodiments, this random number could be manipulated by a node that submits the block. In some embodiments, however, nodes have an incentive to propagate a random hash as a competing node is more likely to submit a correct block hash in the time it takes to manipulate this random value. In some embodiments, each block includes a timestamp.

In step 3102, the hash may be converted to a stimulus (which may be, e.g., audio, visual, vibratory, electromagnetic, or some other input) that may be applied to a user. In step 3103, the user's biological response to the stimulus is recorded. This response and recorded signal may be a function of the block's hash and/or input signal, meaning that the response cannot have been generated any earlier than the timestamp of the block upon which the input signal is based. The recorded signal may also be a function of biological properties of the user. In this manner, the recorded signal may be both identifiable and the time of its origination may be constrained within a known period of time, which could be less than a second in some embodiments. This provides a high degree of reliability as an attacker would have had to simulate the signal in the amount of time between said block hash and the moment the recorded signal was submitted, which may be as little as less than a second. In optional step 3104, the recorded signal may be filtered to provide information on other valuable features. In the case of brainwaves, this may be a subconscious response to an advertisement or other media.

In step 3105, the recorded signal (or data derived therefrom) may be transmitted to a network node. The initial receipt of the recorded may be timestamped. In some embodiments, the timestamp of receipt may be compared to the timestamp of the blockhash. In this manner, the amount of time between origination of the blockhash and origination of the recorded signal may be determined. This may offer an additional security check, as unusually long delays or timestamps prior to generation of the hash with which they are associated may indicate fraudulent data. In step 3106, the signal may be transmitted to a plurality of nodes within a decentralized network. The nodes may then analyze the signal and reach a consensus on the identity of the user using any of the processes discussed above.

Figure 31:
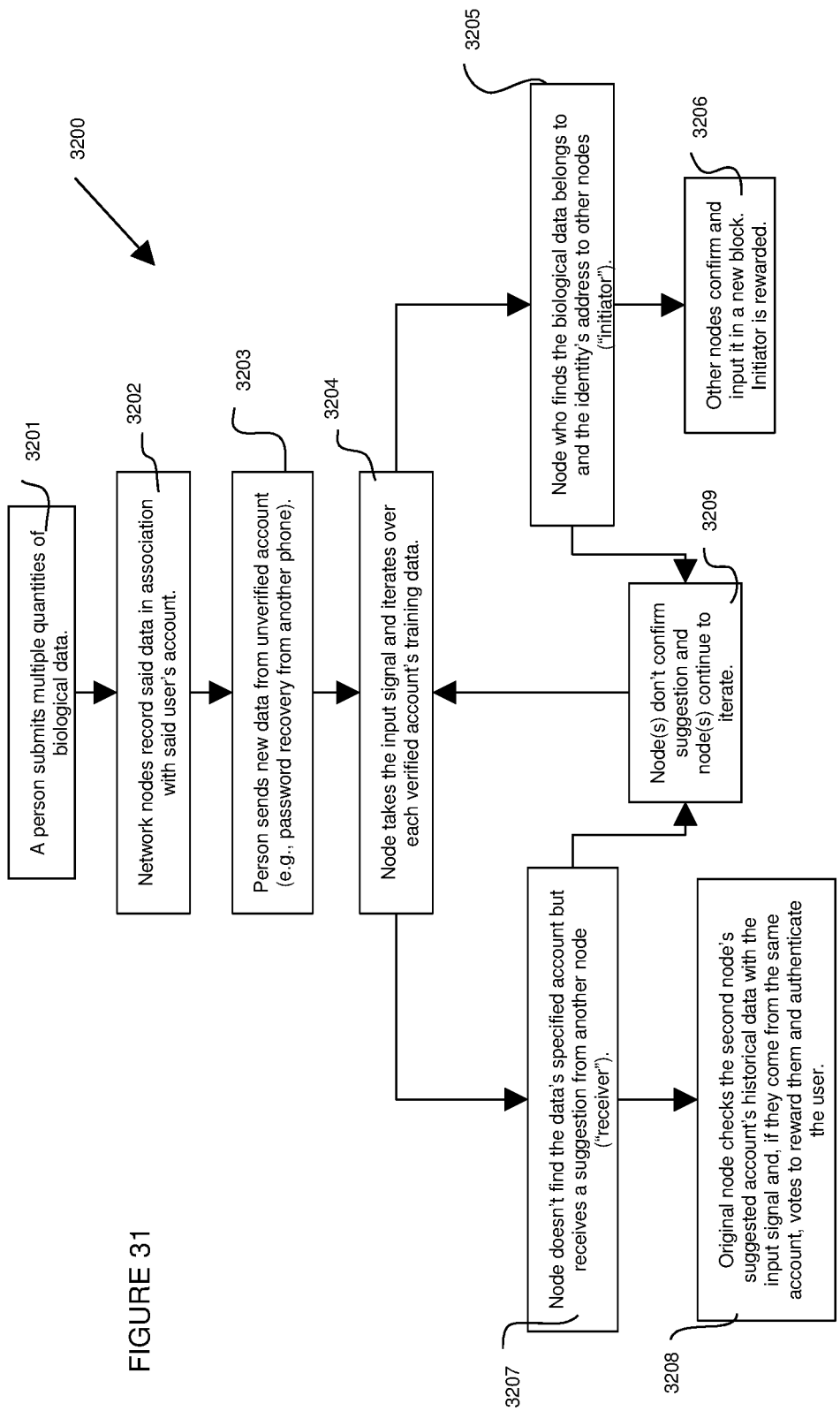
FIG. 31 illustrates an exemplary method 3200 for submitting and processing biological data.

FIG. 31 illustrates an exemplary method 3200 for submitting and processing biological data. In step 3201, a user may submit biological data. In embodiments where the user submits a large quantity of biological data, optionally over a prolonged period of time, the data may be used to establish and verify the user's account in a reward system. The account may have additional security checks, such as verified online accounts and phone number. In some embodiments, the biological data alone or in combination with the other checks may ensure that the user does not have more than one account. In step 3202, one or more nodes in a network may record the received biological data in association with the user's account. The nodes may begin to train their algorithms on this data as well as data received from other users. In optional step 3203, a user who temporarily or permanently lacks access to alternative methods of verification (e.g., encryption keys associated with a previously used wireless device), the user may submit biological data to the network in order to prove that they are truly the owner of their account. Upon verifying the user's identity using the biological data, the network may optionally associate new alternative verification information (such as an encryption key on a new wireless device) with the user's account.

In step 3204, a given node may analyze the biological data to determine an identity of the user. In some embodiments, step 3204 may be performed in accordance with the process described with respect to FIG. 27. In step 3205, an initiator node finds a match with high verification probability, and transmits the match to other nodes in the network. In step 3206, other nodes in the network confirm the submitted match. Optionally, the initiator node may be rewarded. In step 3207, a node may receive a suggested match from another node within the network and attempt to verify the suggested match. If the match is confirmed, the node may continue to step 3208, and may vote to reward the initiator node from which the suggested match is received. If the match is not confirmed, the method may continue to step 3209, in which the node may vote that the suggested match is invalid. Optionally, the node may also vote to punish the initiator node for submitting a false match. In the event that consensus is reached that the suggested match is invalid, the method may return to step 3204, in which one or more nodes continue iterating through a database of candidate users to identify the user from whom the biological data was received.

Figure 32:
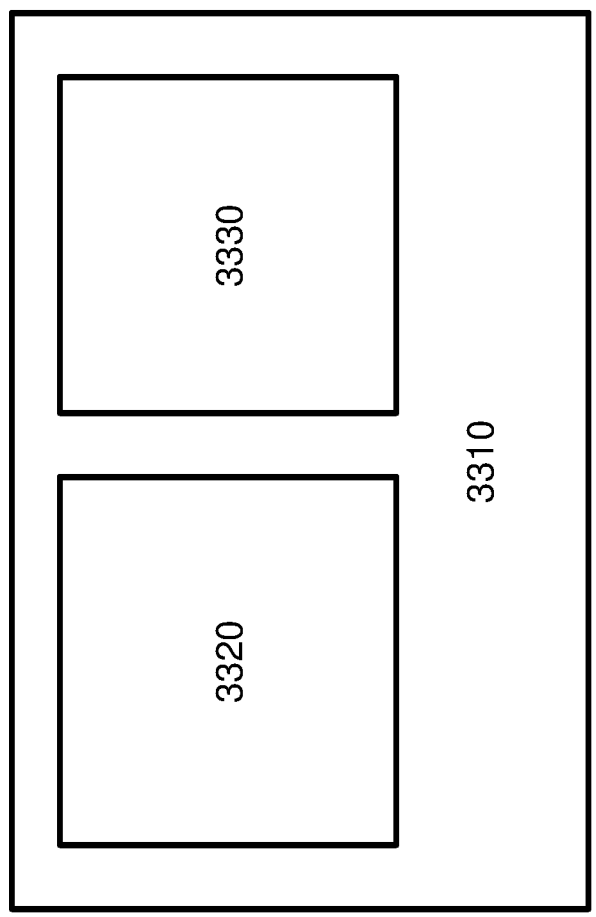
FIG. 32 illustrates an exemplary computing device.

FIG. 32 illustrates an exemplary computing device 3310. The computing device may include a memory 3320, which may store instructions configured to be executed by a processor 3330. In some embodiments, the computing device 3310 may be configured to use remote processors and/or to access remotely stored data, such as by using cloud computing and/or cloud storage. The user devices, wireless devices, and nodes described herein may optionally incorporate some or all of the features of this exemplary computing device.

EXEMPLARY EMBODIMENTS

Embodiment 1

A system for applying and/or receiving an electrical signal, the system comprising:
a body;
a conductor configured to be electrically coupled to at least one of a power source and a detector;
a first filament, the first filament comprising a base portion and a first tip end, the base portion being electrically coupled to the conductor, the first filament being electrically conductive such that the first filament is configured to carry an electrical signal between the base portion and the first tip end;
wherein at least a portion of the first filament is arranged to contact a biological tissue portion.

Embodiment 2

The system of embodiment 1, wherein the first tip end of the first filament extends outwardly relative to the body such that the first tip end is arranged to contact the biological tissue portion.

Embodiment 3

The system of any of embodiments 1 and 2, wherein the first tip end has a width of less than 50 microns.

Embodiment 4

The system of any of embodiments 1-3, wherein the first filament further comprises a second tip end, the second tip end extending outwardly relative to the body such that the second tip end is arranged to contact a biological tissue portion; wherein the base portion electrically contacts the conductor at a position on the filament between the first tip end and the second tip end.

Embodiment 5

The system of any of embodiments 1-4, wherein the body encloses at least a portion of the conductor, the body further comprising a first surface, wherein first filament extends outwardly relative to the first surface such that the first surface is configured to abut the biological tissue portion when the first filament contacts the biological tissue portion.

Embodiment 6

The system of embodiment 5, further comprising an anchor, the first filament being coupled to the anchor.

Embodiment 7

The system of embodiment 6, wherein the body comprises a cavity shaped to receive the anchor;
wherein the body, anchor, and filament are arranged such that when the anchor is disposed within the cavity, the first tip end of the filament extends outwardly relative to the body such that the first tip end is arranged to contact the biological tissue portion.

Embodiment 8

The system of embodiment 7, wherein one of the cavity and the anchor comprises a projection and the other of the cavity and the anchor comprises a complementary recess, wherein the anchor is configured to be snap-fit into the cavity such that the projection is retained within the recess.

Embodiment 9

The system of any of embodiments 7 and 8, further comprising a second anchor and a second filament being coupled to the second anchor;
wherein the body comprises a second cavity shaped to receive the second anchor, the body, second anchor, and second filament being arranged such that when the second anchor is disposed within the second cavity, a tip end of the second filament extends outwardly relative to the body such that the tip end of the second filament is arranged to contact the biological tissue portion.

Embodiment 10

The system of any of embodiments 1-9, wherein the body comprises a substantially arcuate portion configured to fit around a portion of a user's ear.

Embodiment 11

The system of any of embodiments 1-10, wherein the body has a deformation characteristic such that when a proximal end of the body is fixed and a torque is applied to a distal end of the body such that the body exhibits 30 degrees of flexion relative to an original state, the body retains at least 10 degrees of deformation after the torque is removed.

Embodiment 12

The system of any of embodiments 1-11, wherein the body has a flexibility characteristic such that a torque less than or equal to 1.3 Newton-meters applied to a distal end of the body when a proximal end of the body is fixed produces at least 30 degrees of flexion.

Embodiment 13

The system of any of embodiments 1-12, further comprising a plurality of filaments, the first filament being among the plurality of filaments, each filament of the plurality of filaments comprising a tip end arranged to contact the biological tissue portion.

Embodiment 14

The system of embodiment 13, wherein each tip end extends outwardly relative to the body in substantially the same direction such that each tip end may contact a substantially flat tissue portion without changing an orientation of the body.

Embodiment 15

The system of any of embodiments 1-14, further comprising a magnetic element, the magnetic element being selected from a group consisting of: a magnet, a toroid, a conductive coil, a magnetic powder, vibratory magnetic element, and a magnetic fluid.

Embodiment 16

The system of embodiment 15, wherein the magnetic element is disposed within the anchor.

Embodiment 17

The system of embodiment 16, wherein the magnetic element is disposed within the body.

Embodiment 18

The system of any of embodiments 1-17, wherein the body comprises an outer surface that approximates a portion of a sphere or cone, the outer surface being sized to fit within a user's ear.

Embodiment 19

The system of embodiment 18, further comprising a speaker, the body comprising a hollow interior that intersects the outer surface, the speaker being arranged to transmit sound waves through the hollow interior.

Embodiment 20

A method of applying and/or receiving an electrical signal via a biological tissue portion, the method comprising:
positioning a system proximate a biological tissue portion, wherein the system comprises:
a body;
a conductor configured to be electrically coupled to at least one of a power source and a detector;
a first filament, the first filament comprising a base portion and a first tip end, the base portion being electrically coupled to the conductor, the first filament being electrically conductive such that the first filament is configured to carry an electrical signal between the base portion and the first tip end;
advancing the first filament toward the biological tissue portion such that the first tip end contacts the biological tissue portion;
using the first filament to apply and/or receive an electrical signal via the biological tissue portion.

Embodiment 21

The method of embodiment 20, wherein the biological tissue portion is skin and the step of advancing the first filament toward the biological tissue portion comprises disposing at least a portion of the first tip end within a pore of said skin.

Embodiment 22

The method of embodiment 21, wherein the first tip end has a width less than or equal to 50 microns, and the pore has a width less than or equal to 50 microns.

Embodiment 23

The method of any of embodiments 20-22, wherein the first tip end of the first filament extends outwardly relative to the body such that the first tip end is arranged to contact the biological tissue portion.

Embodiment 24

The method of any of embodiments 20-23, wherein the body encloses at least a portion of the conductor, the body further comprising a first surface, wherein first filament extends outwardly relative to the first surface such that the first surface is configured to abut the biological tissue portion when the first filament contacts the biological tissue portion.

Embodiment 25

The method of any of embodiments 20-24, further comprising: disposing a substantially arcuate portion of the body around a portion of a user's ear such that the biological tissue portion with which the first tip end is in contact is a portion of skin behind the user's ear.

Embodiment 26

The method of any of embodiments 20-25, wherein the body has a deformation characteristic such that when a proximal end of the body is fixed and a torque is applied to a distal end of the body such that a body of the body exhibits 30 degrees of flexion relative to an original state, the body retains at least 10 degrees of deformation after the torque is removed.

Embodiment 27

The method of any of embodiments 20-26, wherein the body has a flexibility characteristic such that a torque less than or equal to 2.5 Newton-meters produces at least 30 degrees of flexion when a proximal end of the body is fixed and said torque is applied to a distal end of the body.

Embodiment 28

The method of any of embodiments 20-27, further comprising applying a force to the body such that the body plastically deforms to adapt to a shape of the biological tissue portion.

Embodiment 29

The method of embodiment 28, wherein the body comprises a first configuration that is substantially straight and a second configuration that is substantially bent, and applying the force results in the body transitioning from the first configuration to the second configuration.

Embodiment 30

The method of any of embodiments 28 and 29, wherein applying the force comprises at least partially wrapping the body around a portion of the user's body.

Embodiment 31

The method of embodiment 30, wherein the portion of the user's body is selected from a group consisting of: an ear, an arm, a hand, a finger, a leg, a foot, a toe, a head, a neck, a back, a pelvic floor, and a penis.

Embodiment 32

The method of any of embodiments 20-31, wherein the system comprises a plurality of filaments, the plurality of filaments comprising the first filament and a second filament, the second filament comprising a second base portion and a second tip end, the second base portion being electrically coupled to the conductor, the second filament being electrically conductive such that the second filament is configured to carry an electrical signal between the second base portion and the second tip end;
wherein the step of advancing the first filament toward the biological tissue portion results in the second tip end being placed in contact with the biological tissue portion.

Embodiment 33

The method of embodiment 32, wherein the biological tissue portion is skin and the step of advancing the first filament toward the biological tissue portion results in:
at least a portion of the first tip end being disposed within a first pore of said skin; and
at least a portion of the second tip end being disposed within a second pore of said skin.

Embodiment 34

The method of any of embodiments 32 and 33, wherein the biological tissue portion contacted by the plurality of filaments is substantially flat, and each filament of the plurality of filaments extends in substantially the same direction, the method further comprising:
placing each tip end of the plurality of filaments in contact with the portion of the biological tissue portion without changing an orientation of the body.

Embodiment 35

The method of any of embodiments 20-34, wherein the system further comprises an anchor, the first filament being coupled to the anchor;
wherein the body comprises a cavity shaped to receive the anchor;
further wherein the body, anchor, and filament are arranged such that when the anchor is disposed within the cavity, the first tip end of the filament extends outwardly relative to the body such that the first tip end is arranged to contact the biological tissue portion.

Embodiment 36

The method of embodiment 35, wherein one of the cavity and the anchor comprises a projection and the other of the cavity and the anchor comprises a complementary recess, wherein the anchor is configured to be snap-fit into the cavity such that the projection is retained within the recess.

Embodiment 37

The method of any of embodiments 20-36, wherein the system further comprises a first magnetic element, the first magnetic element being selected from a group consisting of: a magnet, a toroid, a conductive coil, a magnetic powder, and a magnetic fluid;
wherein the method further comprises placing the first magnetic element proximate the biological tissue portion such that an energy field applied by the first filament is distributed in a different pattern than said energy field would have been distributed if the first magnetic element were not present.

Embodiment 38

The method of embodiment 37, wherein the first magnetic element is disposed within the anchor.

Embodiment 39

The method of embodiment 37, wherein the first magnetic element is disposed within the body.

Embodiment 40

The method of embodiment 37, further comprising:
positioning a second system proximate a second biological tissue portion, wherein the second system comprises a conductor, a filament, and a second magnetic element, the second magnetic element being selected from a group consisting of: a magnet, a toroid, a conductive coil, a magnetic powder, and a magnetic fluid;
advancing the second system toward the second biological tissue portion such that the filament of the second system contacts the second biological tissue portion;
placing the second magnetic element proximate the second biological tissue portion such that an energy field applied by the second system is distributed in a different pattern than said energy field applied by the second system would have been distributed if the second magnetic element were not present.

Embodiment 41

The method of embodiment 40, wherein the first magnetic element has a first pair of north-south magnetic poles, and the second magnetic element has a second pair of north-south magnetic poles, and placing the first and second magnetic elements proximate the respective biological tissue portions results in a configuration wherein like poles of the respective magnetic elements are directed substantially toward one another.

Embodiment 42

The method of embodiment 40, wherein the first magnetic element has a first pair of north-south magnetic poles, and the second magnetic element has a second pair of north-south magnetic poles, and placing the first and second magnetic elements proximate the respective biological tissue portions results in a configuration wherein opposite poles of the respective magnetic elements are directed substantially toward one another.

Embodiment 43

The method of embodiment 40, wherein the first system comprises a first plurality of magnetic elements aligned in alternating polarities along a surface of the body, and the second system comprises a second plurality of magnetic elements in alternating polarities opposite to those of the first plurality of magnetic elements, the biological tissue portion being disposed between the first system and the second system.

Embodiment 44

The method of embodiment 40, wherein the first system comprises a first plurality of magnetic elements aligned in alternating polarities along a surface of the body, and the second system comprises a second plurality of magnetic elements in alternating polarities identical to those of the first plurality of magnetic elements, the biological tissue portion being disposed between the first system and the second system.

Embodiment 45

The method of any of embodiments 40-44, wherein one or more magnetic elements may be a mechanically vibrating element.

Embodiment 46

The method of any of embodiments 20-45, further comprising placing at least a portion of the system within a user's ear.

Embodiment 47

The method of embodiment 46, wherein the system comprises a speaker, the method further comprising using the speaker to transmit sound waves to the user's ear.

Embodiment 48

A system for applying and/or receiving an electrical signal, the system comprising:
a conductive tip, the tip comprising a channel and an outer surface having a shape that approximates a portion of a sphere or cone, the tip being sized to fit within a user's ear;
a base configured to be coupled to the tip, the base comprising a conductor in electrical contact with the tip such that an electrical signal may pass between the base and the tip.

Embodiment 49

The system of embodiment 48, wherein the base comprises a male connector, and the tip comprises a female connector, and the tip and base are configured to engage one-another via the male and female connectors.

Embodiment 50

The system of embodiment 49, wherein the base comprises an electrical contact portion, the electrical contact portion being positioned such that when the tip and base engage one-another, a portion of the tip is resiliently biased against the electrical contact portion.

Embodiment 51

The system of any of embodiments 48-50, wherein the base further comprises a speaker, the speaker being arranged to transmit sound waves through the channel when the tip is coupled to the base.

Embodiment 52

The system of any of embodiments 48-51, wherein the tip comprises a plurality of conductive filaments, the plurality of conductive filaments comprising a first filament extending radially outwardly from the outer surface and being arranged to directly contact a portion of the user's skin when the tip is positioned within the user's ear.

Embodiment 53

The system of any of embodiments 48-52, wherein the base comprises a magnetic element, the magnetic element being selected from a group consisting of: a magnet, a toroid, a conductive coil, a magnetic powder, and a magnetic fluid;
wherein the magnetic element is configured to alter an energy field applied by the tip when an electrical is applied to the tip relative to an energy field that would have resulted had the magnetic element not been present.

Embodiment 54

The system of any of embodiments 48-53, wherein the tip consists essentially of a conductive material having a modulus of elasticity less than 4.5 GPa.

Embodiment 55

A method for applying and/or receiving an electrical signal, the method comprising:
placing a conductive tip within a user's ear such that the tip contacts a portion of the user's skin within the ear, wherein the tip comprises a channel and is coupled to a base, the base comprising a conductor in electrical contact with the tip such that an electrical signal may pass between the base and the tip;
applying and/or receiving an electrical signal via the portion of the user's skin.

Embodiment 56

The method of embodiment 55, wherein the base comprises a male connector, and the tip comprises a female connector, the method further comprising connecting the male connector to the female connector.

Embodiment 57

The method of embodiment 56, wherein connecting the male connector to the female connector results in a portion of the tip being resiliently biased against an electrical contact portion disposed on the base.

Embodiment 58

The method of any of embodiments 55-57, wherein the base further comprises a speaker, the method further comprising using the speaker to transmit sound waves through the channel.

Embodiment 59

The method of any of embodiments 55-58, wherein the tip comprises a plurality of conductive filaments, the plurality of conductive filaments comprising a first filament extending radially outwardly from an outer surface of the tip,
wherein placing the tip within the user's ear results in the first filament directly contacting the portion of the user's skin.

Embodiment 60

The method of any of embodiments 55-59, wherein the base comprises a magnetic element, the magnetic element being selected from a group consisting of: a magnet, a toroid, a conductive coil, a magnetic powder, and a magnetic fluid;
wherein the method further comprises placing the magnetic element proximate the user's ear such that an energy field applied by the tip is distributed in a different pattern than said energy field would have been distributed if the magnetic element were not present.

Embodiment 61

The method of any of embodiments 55-60, wherein the tip consists essentially of a conductive material having a modulus of elasticity less than 3.5 GPa.

Embodiment 62

A method for applying and/or receiving an electrical signal, the method comprising:
placing a system comprising a body and an electrode in contact with a biological tissue portion, wherein the body has:
a deformation characteristic such that when a proximal end of the body is fixed and a first torque is applied to a distal end of the body such that the body exhibits 30 degrees of flexion relative to an original state, the body retains at least 10 degrees of deformation after the first torque is removed
a flexibility characteristic such that a second torque less than or equal to 2.5 Newton-meters produces at least 30 degrees of flexion when the second torque is applied to a distal end of the body while a proximal end of the body is fixed;
applying a force to the body such that the body plastically deforms to adapt to a shape of the biological tissue portion;
using the electrode to apply and/or receive an electrical signal via the biological tissue portion.

Embodiment 63

The method of embodiment 62, wherein the body comprises a first configuration that is substantially straight and a second configuration that is substantially bent, and applying the force results in the body transitioning from the first configuration to the second configuration.

Embodiment 64

The method of any of embodiments 62 and 63, wherein applying the force comprises at least partially wrapping the body around a portion of a user's body.

Embodiment 65

The method of any of embodiments 64, wherein the portion of the user's body is selected from a group consisting of: an ear, an arm, a hand, a finger, a leg, a foot, a toe, a head, a neck, and a penis.

Embodiment 66

The method of any of embodiments 62-65, wherein the electrode comprises a plurality of conductive filaments, the plurality of conductive filaments comprising a first filament extending radially outwardly from an outer surface of the body, wherein placing the system in contact with the biological tissue portion results in the first filament directly contacting the biological tissue portion.

Embodiment 67

The method of any of embodiments 62-66, wherein the system comprises a magnetic element, the magnetic element being selected from a group consisting of: a magnet, a toroid, a conductive coil, a magnetic powder, and a magnetic fluid;
wherein the method further comprises placing the magnetic element proximate the biological tissue portion such that an energy field applied by the electrode is distributed in a different pattern than said energy field would have been distributed if the magnetic element were not present.

Embodiment 68

The method of any of embodiments 62-65 and 67, wherein the electrode is a surface of the body.

Embodiment 69

The method of any of embodiments 62-68, wherein the body is disposed in one or more coils around a user's thigh, and the electrode is arranged along the user's pelvic floor and a second is electrode arranged around skin near the user's distal hip.

Embodiment 70

The method of any of embodiments 62-68, wherein the body is disposed around a penis, and the biological tissue portion is on the penis.

Embodiment 71

The method of any of embodiments 62-68, wherein the body is disposed in a ring around a bicep, and the biological tissue portion is on a shoulder and/or a proximal portion of bicep region, wherein a second electrode is placed in contact with a distal portion of the bicep.

Embodiment 72

The method of any of embodiments 62-68, wherein the body is disposed around a knee.

Embodiment 73

The method of any of embodiments 62-68, wherein the electrode is arranged along a path of a vagus nerve.

Embodiment 74

The method of any of embodiments 62-68, wherein the body may be arranged proximal to an ankle, wherein the electrode is disposed near a location with visceral or nervous entities.

Embodiment 75

The method of any of embodiments 62-74, wherein the body is intertwined with itself.

Embodiment 76

The method of any of embodiments 62-75, wherein the body is coiled multiple times.

Embodiment 77

The method of any of embodiments 62-76, wherein the body is intertwined with itself after it has been coiled.

Embodiment 78

The method of embodiment any of embodiments 62-68, wherein the body is disposed around the lower spine substantially between T-8 and S-3.

Embodiment 79

The method of embodiment any of embodiments 62-68, wherein the body is disposed around the lower spine substantially between T-1 and L-2.

Embodiment 80

The method of embodiment any of embodiments 62-68, in which the body is disposed around T11.

Embodiment 81

A system for applying and/or receiving an electrical signal, the system comprising:
a body;
a conductor configured to be electrically coupled to at least one of a power source and a detector;
an electrode, the electrode comprising a surface configured to contact a biological tissue portion and apply and/or receive an electrical signal to and/or from the biological tissue portion; and
a magnetic element, the magnetic element being selected from a group consisting of: a magnet, a toroid, a conductive coil, a magnetic powder, and a magnetic fluid.

Embodiment 82

The system of embodiment 81, wherein the body encloses at least a portion of the conductor, the electrode being supported on a portion of the body.

Embodiment 83

The system of any of embodiments 81 and 82, further comprising an anchor, the electrode being coupled to the anchor;
wherein the body comprises a cavity shaped to receive the anchor;
wherein the body, anchor, and electrode are arranged such that when the anchor is disposed within the cavity, the electrode is arranged to contact the biological tissue portion.

Embodiment 84

The system of embodiment 83, wherein one of the cavity and the anchor comprises a projection and the other of the cavity and the anchor comprises a complementary recess, wherein the anchor is configured to be snap-fit into the cavity such that the projection is retained within the recess.

Embodiment 85

The system of any of embodiments 83 and 84, wherein the magnetic element is disposed within the anchor.

Embodiment 86

The system of any of embodiments 83 and 84, wherein the magnetic element is disposed within the body proximate the cavity.

Embodiment 87

A method of applying and/or receiving an electrical signal via a biological tissue portion, the method comprising:
positioning a first system proximate a biological tissue portion, wherein the system comprises: a first body;
a first conductor configured to be electrically coupled to at least one of a power source and a detector;
a first electrode, the first electrode comprising a surface configured to contact a first biological tissue portion and apply and/or receive an electrical signal to and/or from the first biological tissue portion; and
a first magnetic element, the first magnetic element being selected from a group consisting of: a magnet, a toroid, a conductive coil, a magnetic powder, and a magnetic fluid.
placing the first magnetic element proximate the first biological tissue portion;
using the first electrode to apply and/or receive an electrical signal via the first biological tissue portion, wherein a first energy field applied by the first electrode is distributed in a different pattern than said first energy field would have been distributed if the first magnetic element were not present.

Embodiment 88

The method of embodiment 87, further comprising:
positioning a second system proximate a second biological tissue portion, wherein the second system comprises a second body, a second conductor, a second electrode, and a second magnetic element, the second magnetic element being selected from a group consisting of: a magnet, a toroid, a conductive coil, a magnetic powder, and a magnetic fluid;

placing the second magnetic element proximate the second biological tissue portion;

using the second electrode to apply and/or receive an electrical signal via the second biological tissue portion, wherein a second energy field applied by the second electrode is distributed in a different pattern than said second energy field would have been distributed if the second magnetic element were not present.

Embodiment 89

The method of embodiment 88, wherein the first magnetic element has a first pair of north-south magnetic poles, and the second magnetic element has a second pair of north-south magnetic poles, and placing the first and second magnetic elements proximate the respective biological tissue portions results in a configuration wherein like poles of the respective magnetic elements are directed substantially toward one another.

Embodiment 90

The method of embodiment 88, wherein the first magnetic element has a first pair of north-south magnetic poles, and the second magnetic element has a second pair of north-south magnetic poles, and placing the first and second magnetic elements proximate the respective biological tissue portions results in a configuration wherein opposite poles of the respective magnetic elements are directed substantially toward one another.

Embodiment 91

The method of any of embodiments 87-90, wherein the first electrode comprises a plurality of filaments.

Embodiment 92

The method of any of embodiments 87-91, further comprising a first anchor, the electrode being coupled to the first anchor;

wherein the first body comprises a first cavity shaped to receive the first anchor;

wherein the first body, first anchor, and first electrode are arranged such that when the first anchor is disposed within the first cavity, the first electrode is arranged to contact the biological tissue portion.

Embodiment 93

The method of embodiment 92, wherein one of the first cavity and the first anchor comprises a projection and the other of the first cavity and the first anchor comprises a complementary recess, wherein the first anchor is configured to be snap-fit into the first cavity such that the projection is retained within the recess.

Embodiment 94

The method of any of embodiments 92 and 93, wherein the first magnetic element is disposed within the first anchor.

Embodiment 95

The method of any of embodiments 92 and 93, wherein the first magnetic element is disposed within the first body proximate the first cavity.

Embodiment 96

A method for obtaining biological data, the method being performed by a local user system comprising a user device that is associated with a user, the method comprising:
receiving a first message comprising an indication of a stimulus to be applied to the user;
in response to receiving the first message, applying the stimulus to the user, the stimulus being applied based on the indication in the first message;
detecting a biological response to the stimulus;
generating first data comprising an indication of the detected biological response; and
transmitting a second message comprising the first data.

Embodiment 97

The method of embodiment 96, wherein the user device comprises a first electrode, and the step of detecting a biological response to the stimulus comprises using the first electrode to record the user's brainwaves.

Embodiment 98

The method of embodiment 97, wherein the user device further comprises a second electrode, and the step of applying the stimulus to the user comprises applying an electrical signal to a portion of the user's head.

Embodiment 99

The method of any of embodiments 96-98, wherein the indication of the stimulus to be applied to the user is based on an at least partially randomly generated number having a publicly verifiable timestamp.

Embodiment 100

The method of any of embodiments 96-99, wherein the first message is received by the user device from a wireless device associated with the user, and the second message is transmitted to the wireless device.

Embodiment 101

The method of any of embodiments 96-99, wherein the first message is received from a network node, and the second message is transmitted to the network node.

Embodiment 102

The method of any of embodiments 96-101, wherein the local user system determines the stimulus to be applied to the user by inputting the indication into a function, wherein

39 the function generates a single output for any given indication within a range of possible values.

Embodiment 103

The method of any of embodiments 96-99, 101, and 102, wherein the local user system further comprises a wireless device, and the step of applying the stimulus to the user is performed by the wireless device.

Embodiment 104

The method of embodiment 103, wherein the step of detecting a biological response comprises using a microphone and/or a camera located on the wireless device to record voice and/or facial data.

Embodiment 105

The method of any of embodiments 96-102, wherein the user device comprises a speaker and the step of applying the stimulus to the user comprises using the speaker to apply an audio stimulus.

Embodiment 106

A system for obtaining biological data, the system comprising:
a memory;
and a processor configured to execute instructions stored on the memory, wherein the system is configured to:
receive a first message comprising an indication of a stimulus to be applied to the user;
in response to receiving the first message, apply the stimulus to the user, the stimulus being applied based on the indication in the first message;
detect a biological response to the stimulus;
generate first data comprising an indication of the detected biological response; and
transmit a second message comprising the first data.

Embodiment 107

The system of embodiment 106, wherein the system comprises a first electrode, and the system is configured to detect a biological response to the stimulus by using the first electrode to record the user's brainwaves.

Embodiment 108

The system of embodiment 107, wherein the system further comprises a second electrode, and the system is configured to apply the stimulus to the user by applying an electrical signal to a portion of the user's head.

Embodiment 109

The system of any of embodiments 106-108, wherein the indication of the stimulus to be applied to the user is based on an at least partially randomly generated number having a publicly verifiable timestamp.

Embodiment 110

The system of any of embodiments 106-109, wherein the first message is received by the user device from a wireless device associated with the user, and the second message is transmitted to the wireless device.

Embodiment 111

The system of any of embodiments 106-109, wherein the first message is received from a network node, and the second message is transmitted to the network node.

Embodiment 112

The system of any of embodiments 106-111, wherein the system is further configured to determine the stimulus to be applied to the user by inputting the indication into a function, wherein the function generates a single output for any given indication within a range of possible values.

Embodiment 113

The system of any of embodiments 106-109, 111, and 112, wherein the system comprises a wireless device, and the step of applying the stimulus to the user is performed by the wireless device.

Embodiment 114

The system of embodiment 113, wherein the system is configured to detect a biological response using a microphone and/or a camera located on the wireless device to record voice and/or facial data.

Embodiment 115

The system of any of embodiments 106-107, wherein the user device comprises a speaker and the step of applying the stimulus to the user comprises using the speaker to apply an audio stimulus.

Embodiment 116

A method for analyzing biological data, the method being performed by a first node in a network, the method comprising:
receiving a first message comprising first data comprising indication of a user's biological response to an applied stimulus;
selecting a candidate user from among a plurality of candidate users for whom biological data is stored in a database accessible by the first node;
retrieving from the database second data associated with the candidate user;
comparing the first data to the second data;
determining, based on the comparison of the first data to the second data, that the user is likely the candidate user;
transmitting a second message to a second node within the network, the second message comprising an indication that the user is likely the candidate user.

Embodiment 117

The method of embodiment 116, further comprising:
receiving a third message comprising third data comprising an indication that a second user is likely a second candidate user;
retrieving from the database fourth data associated with the second candidate user;
comparing the third data to the fourth data;

determining, based on the third data and the fourth data, that the second user is likely the second candidate user;
transmitting a fourth message comprising an indication that the second user is likely the second candidate user.

Embodiment 118

The method of any of embodiments 116 and 117, wherein the database is updated to include the first data and an indication that the first data is associated with the user.

Embodiment 119

The method of any of embodiments 116-118, wherein the first data comprises brainwave data.

Embodiment 120

The method of any of embodiments 116-119, wherein the stimulus is based on an at least partially randomly generated number having a publicly verifiable timestamp.

Embodiment 121

A first node for analyzing biological data, the first node comprising:
a memory;
and a processor configured to execute instructions stored on the memory, wherein the first node is configured to:
receive a first message comprising first data comprising indication of a user's biological response to an applied stimulus;
select a candidate user from among a plurality of candidate users for whom biological data is stored in a database accessible by the first node;
retrieve from the database second data associated with the candidate user;
compare the first data to the second data;
determine, based on the comparison of the first data to the second data, that the user is likely the candidate user;
transmit a second message to a second node within a network, the second message comprising an indication that the user is likely the candidate user.

Embodiment 122

The first node of embodiment 121, wherein the first node is further configured to:
receive a third message comprising third data comprising an indication that a second user is likely a second candidate user;
retrieve from the database fourth data associated with the second candidate user;
compare the third data to the fourth data;
determine, based on the third data and the fourth data, that the second user is likely the second candidate user;
transmit a fourth message comprising an indication that the second user is likely the second candidate user.

Embodiment 123

The first node of any of embodiments 121 and 122, wherein the database is updated to include the first data and an indication that the first data is associated with the user.

Embodiment 124

The first node of any of embodiments 121-123, wherein the first data comprises brainwave data.

Embodiment 125

The first node of any of embodiments 121-124, wherein the stimulus is based on an at least partially randomly generated number having a publicly verifiable timestamp.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A system for applying and/or receiving an electrical signal, the system comprising:
a first earpiece comprising:
a first conductive tip, the first tip comprising a first channel and a first outer surface having a shape that approximates a portion of a sphere or cone, the first tip being sized to fit within a user's first ear;
a first base configured to be coupled to the first tip, the first base comprising a first conductor in electrical contact with the first tip such that an electrical signal may pass between the first base and the first tip;
a second earpiece comprising:
a second conductive tip, the second tip comprising a second channel and a second outer surface, the second tip being sized to fit within a user's second ear;
a second base configured to be coupled to the second tip, the second base comprising a second conductor in electrical contact with the second tip such that an electrical signal may pass between the second base and the second tip;
a power source, the power source being connected to the first earpiece to apply a first electrical signal within the user's first ear via the first earpiece;
a detector, the detector being connected to the second earpiece to receive a second electrical signal from the user's second ear via the second earpiece;
wherein the system, using the power source and the detector, is configured to apply the first electrical signal to the first ear and receive the second signal from the user's second ear simultaneously; and
wherein the system, using a processor, is configured to generate data based on the second electrical signal, the second electrical signal being related to the first electrical signal such that the data generated based on the second electrical signal is configured to be analyzed to assess whether the second electrical signal was received after the first electrical signal was applied.

2. The system of claim 1, wherein the first base comprises a male connector, and the first tip comprises a female connector, and the first tip and first base are configured to engage one-another via the male and female connectors.

3. The system of claim 2, wherein the first base comprises an electrical contact portion, the electrical contact portion being positioned such that when the first tip and first base engage one-another, a portion of the first tip is resiliently biased against the electrical contact portion.

4. The system of claim 1, wherein the first base further comprises a speaker, the speaker being arranged to transmit sound waves through the channel when the first tip is coupled to the first base.

5. The system of claim 1, wherein the first tip comprises a plurality of conductive filaments, the plurality of conductive filaments comprising a first filament extending radially outwardly from the outer surface and being arranged to directly contact a portion of the user's skin when the tip is positioned within the user's ear.

6. The system of claim 1, wherein the first base comprises a magnetic element, the magnetic element being selected from a group consisting of: a magnet, a toroid, a conductive coil, a magnetic powder, and a magnetic fluid;
   wherein the magnetic element is configured to alter an energy field applied by the first tip when the first electrical signal is applied relative to an energy field that would have resulted had the magnetic element not been present.

7. The system of claim 1, wherein the first tip consists essentially of a conductive material having a modulus of elasticity less than 4.5 GPa.

8. The system of claim 1, wherein the system is configured to apply the first signal based on a timestamped message received from a network node, and the system is further configured to transmit the data generated based on the second electrical to the network node.

9. A method for applying and/or receiving an electrical signal, the method comprising:
   placing a first earpiece within a user's first ear, the first earpiece comprising:
      a first conductive tip, the first tip comprising a first channel and a first outer surface having a shape that approximates a portion of a sphere or cone, the first tip being sized to fit within a user's first ear;
      a first base configured to be coupled to the first tip, the first base comprising a first conductor in electrical contact with the first tip such that an electrical signal may pass between the first base and the first tip;
   placing a second earpiece within the user's second ear, the second earpiece comprising:
      a second conductive tip, the second tip comprising a second channel and a second outer surface, the second tip being sized to fit within a user's second ear;
      a second base configured to be coupled to the second tip, the second base comprising a second conductor in electrical contact with the second tip such that an electrical signal may pass between the second base and the second tip;
   applying, using the first earpiece, a first electrical signal within the user's first ear;
   detecting, using the second earpiece, a second electrical signal from the user's second ear;
   generating data based on the second electrical signal, the second electrical signal being related to the first electrical signal such that the data generated based on the second electrical signal is configured to be analyzed to assess whether the second electrical signal was received after the first electrical signal was applied;
   wherein the system is configured to apply the first electrical signal to the first ear and receive the second signal from the user's second ear simultaneously.

10. The method of claim 9, wherein the first base comprises a male connector, and the first tip comprises a female connector, the method further comprising connecting the male connector to the female connector.

11. The method of claim 10, wherein connecting the male connector to the female connector results in a portion of the first tip being resiliently biased against an electrical contact portion disposed on the first base.

12. The method of claim 9, wherein the first base further comprises a speaker, the method further comprising using the speaker to transmit sound waves through the channel.

13. The method of any of claim 9, wherein the first tip comprises a plurality of conductive filaments, the plurality of conductive filaments comprising a first filament extending radially outwardly from an outer surface of the tip,
   wherein placing the first earpiece within the user's ear results in the first filament directly contacting the portion of the user's skin.

14. The method of claim 9, wherein the first base comprises a magnetic element, the magnetic element being selected from a group consisting of: a magnet, a toroid, a conductive coil, a magnetic powder, and a magnetic fluid;
   wherein the method further comprises placing the magnetic element proximate the user's first ear such that an energy field applied by the first tip is distributed in a different pattern than said energy field would have been distributed if the magnetic element were not present.

15. The method of claim 9, wherein the first tip consists essentially of a conductive material having a modulus of elasticity less than 3.5 GPa.

* * * * *